US007091245B2

(12) United States Patent
Jeppesen et al.

(10) Patent No.: US 7,091,245 B2
(45) Date of Patent: Aug. 15, 2006

(54) COMPOUNDS, THEIR PREPARATION AND USE

(75) Inventors: Lone Jeppesen, Virum (DK); John Patrick Mogensen, Herlev (DK); Ingrid Pettersson, Frederiksberg (DK); Per Sauerberg, Farum (DK)

(73) Assignee: Novo Novdisk A/S, Bagsvaerd (DK)

( * ) Notice: Subject to any disclaimer, the term of this patent is extended or adjusted under 35 U.S.C. 154(b) by 50 days.

(21) Appl. No.: 10/654,699

(22) Filed: Sep. 4, 2003

(65) Prior Publication Data

US 2004/0143006 A1  Jul. 22, 2004

Related U.S. Application Data

(60) Provisional application No. 60/409,814, filed on Sep. 11, 2002.

(30) Foreign Application Priority Data

Sep. 5, 2002  (DK)  .................. PA 2002 01301
May 23, 2003  (DK)  .................. PA 2003 00784

(51) Int. Cl.
*A61K 31/19*  (2006.01)
*C07C 315/00*  (2006.01)

(52) U.S. Cl. ..................... 514/571; 562/427
(58) Field of Classification Search ............. 514/571; 562/427
See application file for complete search history.

(56) References Cited

U.S. PATENT DOCUMENTS

| 3,449,325 A | 6/1969 | Nahm et al. ............. 260/239.1 |
| 2005/0070583 A1 | 3/2005 | Jeppesen et al. ............ 514/357 |
| 2005/0080115 A1 | 4/2005 | Jeppesen et al. ............ 514/357 |

FOREIGN PATENT DOCUMENTS

| WO | WO 97/27847 A1 | 8/1997 |
| WO | WO 97/27857 A1 | 8/1997 |
| WO | WO 97/28115 A1 | 8/1997 |
| WO | WO 97/28137 A1 | 8/1997 |
| WO | WO 97/28149 A1 | 8/1997 |
| WO | WO 97/48674 A1 | 12/1997 |
| WO | WO 98/27974 A1 | 7/1998 |
| WO | WO 99/04815 A1 | 2/1999 |
| WO | WO 00/63153 A1 | 10/2000 |
| WO | WO 01/00603 A1 | 1/2001 |
| WO | WO 01/025181 A1 | 4/2001 |
| WO | WO 01/55085 A1 | 8/2001 |
| WO | WO 01/55086 A1 | 8/2001 |
| WO | WO 01/79197 A1 | 10/2001 |
| WO | WO 02/14291 A1 | 2/2002 |
| WO | WO 02/059098 A1 | 8/2002 |
| WO | WO 03/011807 A1 | 2/2003 |
| WO | WO 03/033453 A1 | 4/2003 |

OTHER PUBLICATIONS

Berger et al., The Journal of Biological Chemistry, vol. 274, No. 10, pp. 6718-6725 (1999).
Leibowitz et al., FEBS Letters 473, pp. 333-336 (2000).
Muoio et al., The Journal of Biological Chemistry, vol. 277, pp. 26089-26097 (2002).
Oliver et al., PNAS, vol. 98, No. 9, pp. 5306-5311 (2001).

*Primary Examiner*—Deborah C. Lambkin
(74) *Attorney, Agent, or Firm*—Rosemarie R. Wilk-Oresscan; Reza Green; Richard W. Bork

(57) ABSTRACT

Novel compounds of the general formula (I), the use of these compounds as pharmaceutical compositions, pharmaceutical compositions comprising the compounds and methods of treatment employing these compounds and compositions. The present compounds may be useful in the treatment and/or prevention of conditions mediated by Peroxisome Proliferator-Activated Receptors (PPAR), in particular the PPARδ suptype.

57 Claims, No Drawings

US 7,091,245 B2

COMPOUNDS, THEIR PREPARATION AND USE

CROSS-REFERENCE TO RELATED APPLICATIONS

This application claims priority under 35 U.S.C. 119 of Danish application no. PA 2002 01301 filed Sep. 5, 2002, Danish application no. PA 2003 00784 filed May 23, 2003 and U.S. application Ser. No. 60/409,814 filed Sep. 11, 2002, the contents of which are fully incorporated herein by reference.

FIELD OF THE INVENTION

The present invention relates to novel compounds, to the use of these compounds as pharmaceutical compositions, to pharmaceutical compositions comprising the compounds and to a method of treatment employing these compounds and compositions. More specifically, the compounds of the invention can be utilised in the treatment and/or prevention of conditions mediated by the Peroxisome Proliferator-Activated Receptors (PPAR), in particular the PPARδ subtype.

BACKGROUND OF THE INVENTION

Coronary artery disease (CAD) is the major cause of death in Type 2 diabetic and metabolic syndrome patients (i.e. patients that fall within the 'deadly quartet' category of impaired glucose tolerance, insulin resistance, hypertriglyceridaemia and/or obesity).

The hypolipidaemic fibrates and antidiabetic thiazolidinediones separately display moderately effective triglyceride-lowering activities although they are neither potent nor efficacious enough to be a single therapy of choice for the dyslipidaemia often observed in Type 2 diabetic or metabolic syndrome patients. The thiazolidinediones also potently lower circulating glucose levels of Type 2 diabetic animal models and humans. However, the fibrate class of compounds are without beneficial effects on glycaemia. Studies on the molecular actions of these compounds indicate that thiazolidinediones and fibrates exert their action by activating distinct transcription factors of the peroxisome proliferator activated receptor (PPAR) family, resulting in increased and decreased expression of specific enzymes and apolipoproteins respectively, both key-players in regulation of plasma triglyceride content. Fibrates, on the one hand, are PPARα activators, acting primarily in the liver. Thiazolidinediones, on the other hand, are high affinity ligands for PPARγ acting primarily on adipose tissue.

Adipose tissue plays a central role in lipid homeostasis and the maintenance of energy balance in vertebrates. Adipocytes store energy in the form of triglycerides during periods of nutritional affluence and release it in the form of free fatty acids at times of nutritional deprivation. The development of white adipose tissue is the result of a continuous differentiation process throughout life. Much evidence points to the central role of PPARγ activation in initiating and regulating this cell differentiation. Several highly specialised proteins are induced during adipocyte differentiation, most of them being involved in lipid storage and metabolism. The exact link from activation of PPARγ to changes in glucose metabolism, most notably a decrease in insulin resistance in muscle, has not yet been clarified. A possible link is via free fatty acids such that activation of PPARγ induces Lipoprotein Lipase (LPL), Fatty Acid Transport Protein (FATP) and Acyl-CoA Synthetase (ACS) in adipose tissue but not in muscle tissue. This, in turn, reduces the concentration of free fatty acids in plasma dramatically, and due to substrate competition at the cellular level, skeletal muscle and other tissues with high metabolic rates eventually switch from fatty acid oxidation to glucose oxidation with decreased insulin resistance as a consequence.

PPARα is involved in stimulating β-oxidation of fatty acids. In rodents, a PPARα-mediated change in the expression of genes involved in fatty acid metabolism lies at the basis of the phenomenon of peroxisome proliferation, a pleiotropic cellular response, mainly limited to liver and kidney and which can lead to hepatocarcinogenesis in rodents. The phenomenon of peroxisome proliferation is not seen in man. In addition to its role in peroxisome proliferation in rodents, PPARα is also involved in the control of HDL cholesterol levels in rodents and humans. This effect is, at least partially, based on a PPARα-mediated transcriptional regulation of the major HDL apolipoproteins, apo A-I and apo A-II. The hypotriglyceridemic action of fibrates and fatty acids also involves PPARα and can be summarised as follows: (I) an increased lipolysis and clearance of remnant particles, due to changes in lipoprotein lipase and apo C-III levels, (II) a stimulation of cellular fatty acid uptake and their subsequent conversion to acyl-CoA derivatives by the induction of fatty acid binding protein and acyl-CoA synthase, (III) an induction of fatty acid β-oxidation pathways, (IV) a reduction in fatty acid and triglyceride synthesis, and finally (V) a decrease in VLDL production. Hence, both enhanced catabolism of triglyceride-rich particles as well as reduced secretion of VLDL particles constitutes mechanisms that contribute to the hypolipidemic effect of fibrates.

PPARδ activation was initially reported not to be involved in modulation of glucose or triglyceride levels. (Berger et al., j. Biol. Chem., 1999, Vol 274, pp. 6718–6725). Later it has been shown that PPARδ activation leads to increased levels of HDL cholesterol in dbldb mice (Leibowitz et al. FEBS letters 2000, 473, 333–336). Further, a PPARδ agonist when dosed to insulin-resistant middle-aged obese rhesus monkeys caused a dramitic dose-dependent rise in serum HDL cholesterol while lowering the levels of small dense LDL, fasting triglycerides and fasting insulin (Oliver et al. PNAS 2001, 98, 5306–5311). The same paper also showed that PPARδ activation increased the reverse cholesterol transporter ATP-binding cassette A1 and induced apolipoprotein A1-specific cholesterol efflux. The involvement of PPARδ in fatty acid oxidation in muscles was further substantiated in PPARα knock-out mice. Muoio et al. (J. Biol. Chem. 2002, 277, 26089–26097) showed that the high levels of PPARδ in skeletal muscle can compensate for deficiency in PPARα. Taken together these observations suggest that PPARδ activation is useful in the treatment and prevention of cardiovascular diseases and conditions including atherosclerosis, hypertriglyceridemia, and mixed dyslipidaemia (WO 01/00603).

A number of PPARδ compounds have been reported to be useful in the treatment of hyperglycemia, hyperlipidemia and hypercholesterolemia (WO 02/59098, WO 01/603, WO 01/25181, WO 02/14291, WO 01/79197, WO 99/4815, WO 97/28149, WO 98/27974, WO 97/28115, WO 97/27857, WO 97/28137, WO 97/27847).

Glucose lowering as a single approach does not overcome the macrovascular complications associated with Type 2 diabetes and metabolic syndrome. Novel treatments of Type 2 diabetes and metabolic syndrome must therefore aim at lowering both the overt hypertriglyceridaemia associated with these syndromes as well as alleviation of hyperglycaemia.

This indicate that research for compounds displaying various degree of PPARα, PPARγ and PPARδ activation should lead to the discovery of efficacious triglyceride and/or cholesterol and/or glucose lowering drugs that have great potential in the treatment of diseases such as type 2 diabetes, dyslipidemia, syndrome X (including the metabolic syndrome, i.e. impaired glucose tolerance, insulin resistance, hypertrigyceridaemia and/or obesity), cardiovascular diseases (including atherosclerosis) and hypercholesteremia.

In WO 97/48674, various antimicrobial diaryls has been described as anti-infective agents. The invention comprises compounds of the formula:

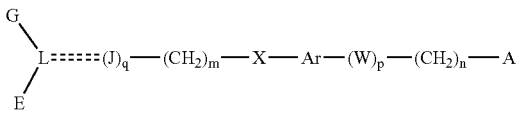

wherein

L may be selected from the group consisting of N, CH and C;

G, E may independently be selected from phenyl, substituted phenyl, phenyl$C_{1-4}$-alkyl, substituted phenyl$C_{1-4}$-alkyl, 2-pyridyl, 3-pyridyl, 4-pyridyl, 2-thienyl and 3-thienyl;

J may be CH or O;

X may be selected from the group consisting of is O, S, NR, and C(O)NR;

Ar may be aryl or substituted aryl;

W may be O or S;

A may be selected from the group consisting of i.a. NRR, amidino, COOH; CHRCOOH, CH=CHR, CH=C(COOH)$_2$;

q, p may independently be are 0 or 1; and m, n may indenpendently be 0–6.

Definitions

In the structural formulas given herein and throughout the present specification the following terms have the indicated meaning:

The term "$C_{1-6}$-alkyl" as used herein, alone or in combination, represent a linear or branched, saturated hydrocarbon chain having the indicated number of carbon atoms. Representative examples include, but are not limited to methyl, ethyl, n-propyl, isopropyl, butyl, isobutyl, sec-butyl, tert-butyl, pentyl, isopentyl, hexyl, isohexyl and the like.

The term "$C_{1-6}$-alkylcarbonyl as used herein, represents a "$C_{1-6}$-alkyl" group as defined above having the indicated number of carbon atoms linked through a carbonyl group. Representative examples include, but are not limited to, methylcarbonyl, ethylcarbonyl, n-propylcarbonyl, isopropylcarbonyl, butylcarbonyl, isobutylcarbonyl, sec-butylcarbonyl, tert-butylcarbonyl, n-pentylcarbonyl, isopentylcarbonyl, neopentylcarbonyl, tert-pentylcarbonyl, n-hexylcarbonyl, isohexylcarbonyl and the like.

The term "$C_{1-6}$-alkylsulfonyl" as used herein refers to a monovalent substituent comprising a "$C_{1-6}$-alkyl" group as defined above linked through a sulfonyl group. Representative examples include, but are not limited to, methylsulfonyl, ethylsulfonyl, n-propylsulfonyl, iso-propylsulfonyl, n-butylsulfonyl, isobutylsulfonyl, sec-butylsulfonyl, tert-butylsulfonyl, n-pentylsulfonyl, isopentylsulfonyl, neopentylsulfonyl, tert-pentylsulfonyl, n-hexylsulfonyl, iso-hexylsulfonyl and the like.

The term "$C_{1-6}$-alkylamido" as used herein, refers to an acyl group linked through an amino group; Representative examples include, but are not limited to acetylamino, propionyl-amino, butyrylamino, isobutyrylamino, pivaloylamino, valerylamino and the like.

The term "$C_{3-6}$-cycloalkyl" as used herein, alone or in combination, represent a saturated monocyclic hydrocarbon group having the indicated number of carbon atoms. Representative examples include, but are not limited to cyclopropyl, cyclobutyl, cyclopentyl, cyclohexyl and the like.

The term "$C_{2-6}$-alkenyl" as used herein, represent an olefinically unsaturated branched or straight hydrocarbon group having from 2 to the specified number of carbon atoms and at least one double bond. Representative examples include, but are not limited to, vinyl, 1-propenyl, 2-propenyl, allyl, iso-propenyl, 1,3-butadienyl, 1-butenyl, hexenyl, pentenyl and the like.

The term "$C_{2-6}$-alkynyl" as used herein, represent an unsaturated branched or straight hydrocarbon group having from 2 to the specified number of carbon atoms and at least one triple bond. Representative examples include, but are not limited to, 1-propynyl, 2-propynyl, 1-butynyl, 2-butynyl, 1-pentynyl, 2-pentynyl and the like.

The term "$C_{4-6}$-alkenynyl" as used herein, represent an unsaturated branched or straight hydrocarbon group having from 4 to the specified number of carbon atoms and both at least one double bond and at least one triple bond. Representative examples include, but are not limited to, 1-penten-4-ynyl, 3-penten-1-ynyl, 1,3-hexadiene-5-ynyl and the like.

The term "$C_{1-6}$-alkoxy" as used herein, alone or in combination, refers to a straight or branched configuration linked through an ether oxygen having its free valence bond from the ether oxygen. Examples of linear alkoxy groups are methoxy, ethoxy, propoxy, butoxy, pentoxy, hexoxy and the like. Examples of branched alkoxy are isopropoxy, sec-butoxy, tert-butoxy, isopentyloxy, isohexyloxy and the like.

The term "$C_{3-6}$-cycloalkoxy" as used herein, alone or in combination, represent a saturated monocyclic hydrocarbon group having the indicated number of carbon atoms linked through an ether oxygen having its free valence bond from the ether oxygen. Examples of cycloalkoxy groups are cyclopropyloxy, cyclobutyloxy, cyclopentyloxy, cyclohexyloxy and the like.

The term "$C_{1-6}$-alkylthio" as used herein, alone or in combination, refers to a straight or branched monovalent substituent comprising a "$C_{1-6}$-alkyl" group as defined above linked through a divalent sulfur atom having its free valence bond from the sulfur atom and having 1 to 6 carbon atoms. Representative examples include, but are not limited to, methylthio, ethylthio, propylthio, butylthio, pentylthio and the like.

The term "$C_{3-6}$-cycloalkylthio" as used herein, alone or in combination, represent a saturated monocyclic hydrocarbon group having the indicated number of carbon atoms linked through a divalent sulfur atom having its free valence bond from the sulfur atom. Examples of cycloalkoxy groups are cyclopropylthio, cyclobutylthio, cyclopentylthio, cyclohexylthio and the like.

The term "$C_{1-6}$-alkylamino" as used herein, alone or in combination, refers to a straight or branched monovalent substituent comprising a "$C_{1-6}$-alkyl" group as defined above linked through amino having a free valence bond from the nitrogen atom. Representative examples include, but are not limited to, methylamino, ethylamino, propylamino, butylamino, pentylamino and the like.

The term "$C_{1-6}$-alkylaminocarbonyl" as used herein refers to a monovalent substituent comprising a $C_1$-monoalkylamino group linked through a carbonyl group such as e.g. methylaminocarbonyl, ethylaminocarbonyl, n-propylaminocarbonyl, isopropylaminocarbonyl, n-butylaminocarbonyl, sec-butylaminocarbonyl, isobutylaminocarbonyl, tert-butylaminocarbonyl, n-pentylaminocarbonyl, 2-methylbutylaminocarbonyl, 3-methylbutylaminocarbonyl, n-hexylaminocarbonyl, 4-methylpentylaminocarbonyl, neopentylaminocarbonyl, n-hexylaminocarbonyl and 2-2-dimethylpropylaminocarbonyl and the like.

The term "$C_{3-6}$-cycloalkylamino" as used herein, alone or in combination, represent a saturated monocyclic hydrocarbon group having the indicated number of carbon atoms linked through amino having a free valence bond from the nitrogen atom. Representative examples include, but are not limited to, cyclopropylamino, cyclobutylamino, cyclopentylamino, cyclohexylamino and the like.

The term "$C_{1-6}$-alkoxy$C_{1-6}$-alkyl" as used herein, alone or in combination, refers to a "$C_{1-6}$-alkyl" group as defined above whereto is attached a "$C_{1-6}$-alkoxy" group as defined above. Representative examples include, but are not limited to, methoxymethyl, ethoxymethyl, methoxyethyl, ethoxyethyl and the like.

The term "aryl" as used herein refers to an aromatic monocyclic or an aromatic fused bi- or tricyclic hydrocarbon group. Representative examples include, but are not limited to, phenyl, naphthyl, anthracenyl, phenanthrenyl, azulenyl and the like.

The term "arylene" as used herein refers to divalent aromatic monocyclic or a divalent aromatic fused bi- or tricyclic hydrocarbon group. Representative examples include, but are not limited to, phenylene, naphthylene and the like.

The term "arylcarbonyl" as used herein represents an "aryl" group as defined above linked through a carbonyl group. Representative examples include, but are not limited to, phenylcarbonyl, naphthylcarbonyl, anthracenylcarbonyl, phenanthrenylcarbonyl, azulenylcarbonyl and the like The term "arylsulfonyl" as used herein refers to an "aryl" group as defined above linked through a sulfonyl group. Representative examples include, but are not limited to, phenylsulfonyl, naphthylsulfonyl, anthracenylsulfonyl, phenanthrenylsulfonyl, azulenylsulfonyl, and the like.

The term "arylamido" as used herein refers to an arylcarbonyl group linked through an amino group. Representative examples include, but are not limited to phenylcarbonylamino, naphthylcarbonylamino, anthracenylcarbonylamino, phenanthrenylcarbonylamino, azulenylcarbonylamino and the like.

The term "halogen" means fluorine, chlorine, bromine or iodine.

The term "perhalomethyl" means trifluoromethyl, trichloromethyl, tribromomethyl or triiodomethyl.

The term "perhalomethoxy" means trifluoromethoxy, trichloromethoxy, tribromomethoxy or triiodomethoxy.

The term "$C_{1-6}$-dialkylamino" as used herein refers to an amino group wherein the two hydrogen atoms independently are substituted with a straight or branched, saturated hydrocarbon chain having the indicated number of carbon atoms. Representative examples include, but are not limited to, dimethylamino, N-ethyl-N-methylamino, diethylamino, dipropylamino, N-(n-butyl)-N-methylamino, di(n-pentyl) amino and the like.

The term "$C_{1-6}$-dialkylaminocarbonyl" as used herein refers to a monovalent substituent comprising a $C_{1-1}$-dialkylamino group linked through a carbonyl group such as dimethyl-aminocarbonyl, N-ethyl-N-methylaminocarbonyl, diethylaminocarbonyl, dipropylaminocarbonyl, N-(n-butyl)-N-methylaminocarbonyl, di(n-pentyl)aminocarbonyl, and the like.

The term "acyl" as used herein refers to a monovalent substituent comprising a "$C_{1-6}$-alkyl" group as defined above linked through a carbonyl group. Representative examples include, but are not limited to, acetyl, propionyl, butyryl, isobutyryl, pivaloyl, valeryl and the like.

The term "heteroaryl" as used herein, alone or in combination, refers to a monovalent substituent comprising a 5–7 membered monocyclic aromatic system or a 8–10 membered bicyclic aromatic system containing one or more heteroatoms selected from nitrogen, oxygen and sulfur, e.g. furyl, thienyl, pyrrolyl, imidazolyl, pyrazolyl, triazolyl, pyridyl, pyrazinyl, pyrimidinyl, pyridazinyl, isothiazolyl, isoxazolyl, oxazolyl, oxadiazolyl, thiadiazolyl, quinolyl, isoquinolyl, quinazolinyl, quinoxalinnyl, indolyl, benzimidazolyl, benzofuranyl, pteridinyl and purinyl and the like.

The term "heteroarylene" as used herein, alone or in combination, refers to divalent 5–7 membered monocyclic aromatic system or a 8–10 membered bicyclic aromatic system containing one or more heteroatoms selected from nitrogen, oxygen and sulfur, e.g. furylene, thienylene, pyrrolylene, imidazolylene, pyrazolylene, triazolylene, pyrazinylene, pyrimidinylene, pyridazinylene, isothiazolylene, isoxazolylene, oxazolylene, oxadiazolylene, thiadiazolylene, quinolylene, isoquinolylene, quinazolinylene, quinoxalinnylene, indolylene, benzimidazolylene, benzofuranylene, pteridinylene and purinylene and the like.

The term "heteroaryloxy" as used herein, alone or in combination, refers to a heteroaryl as defined herein linked to an oxygen atom having its free valence bond from the oxygen atom e.g. pyrrolyloxy, imidazolyloxy, pyrazolyloxy, triazolyloxy, pyrazinyloxy, pyrimidinyloxy, pyridazinyloxy, isothiazolyloxy, isoxazolyloxy, oxazolyloxy, oxadiazolyloxy, thiadiazolyloxy, quinolinyloxy, isoquinolinyloxy, quinazolinyloxy, quinoxalinyloxy, indoltloxy, benzimidazolyloxy, benzofuranyloxy, pteridinyloxy and purinyloxy and the like.

The term "aralkyl" as used herein refers to a straight or branched saturated carbon chain containing from 1 to 6 carbons substituted with an aromatic carbohydride. Representative examples include, but are not limited to, benzyl, phenethyl, 3-phenylpropyl, 1-naphthyl-methyl, 2-(1-naphthyl)ethyl and the like.

The term "aryloxy" as used herein refers to phenoxy, 1-naphthyloxy, 2-naphthyloxy and the like.

The term "aralkoxy" as used herein refers to a $C_{1-6}$-alkoxy group substituted with an aromatic carbohydride, such as benzyloxy, phenethoxy, 3-phenylpropoxy, 1-naphthyl-methoxy, 2-(1-naphtyl)ethoxy and the like.

The term "heteroaralkyl" as used herein refers to a straight or branched saturated carbon chain containing from 1 to 6 carbons substituted with a heteroaryl group; such as (2-furyl)methyl, (3-furyl)methyl, (2-thienyl)methyl, (3-thienyl)methyl, (2-pyridyl)methyl, 1-methyl-1-(2-pyrimidyl) ethyl and the like.

The term "heteroaralkoxy" as used herein refers to a heteroarylalkyl as defined herein linked to an oxygen atom having its free valence bond from the oxygen atom. Representative examples include, but are not limited to, (2-furyl) methyl, (3-furyl)methyl, (2-thienyl)methyl, (3-thienyl)methyl, (2-pyridyl)methyl, 1-methyl-1-(2-pyrimidyl)ethyl linked to oxygen, and the like.

The term "arylthio" as used herein, alone or in combination, refers to an aryl group linked through a divalent sulfur atom having its free valence bond from the sulfur atom, the aryl group optionally being mono- or polysubstituted with $C_{1-6}$-alkyl, halogen, hydroxy or $C_{1-6}$-alkoxy. Representative examples include, but are not limited to, phenylthio, (4-methylphenyl)-thio, (2-chlorophenyl)thio and the like.

Certain of the above defined terms may occur more than once in the structural formulae, and upon such occurrence each term shall be defined independently of the other.

The term "optionally substituted" as used herein means that the groups in question are either unsubstituted or substituted with one or more of the substituents specified. When the groups in question are substituted with more than one substituent the substituents may be the same or different.

DESCRIPTION OF THE INVENTION

The present invention relates to compounds of the general formula (1):

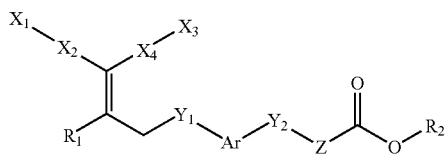

(I)

wherein $X_1$ is aryl or heteroaryl each of which is optionally substituted with one or more substituents selected from
    halogen, hydroxy, cyano, amino or carboxy; or
    $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; and $X_2$ is arylene or heteroarylene each of which is optionally substituted with one or more substituents selected from
    halogen, hydroxy, cyano, amino or carboxy; or
    $C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, $C_{3-6}$-cycloalkylthio, $C_{1-6}$-alkylamino, $C_{1-6}$-dialkylamino or $C_{3-6}$-cycloalkylamino each of which is optionally substituted with one or more halogens; and $X_3$ is aryl or heteroaryl each of which is optionally substituted with one or more substituents selected from
    halogen, hydroxy, cyano, amino or carboxy; or
    $C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-alkylamino, $C_{1-6}$-dialkylamino or $C_{3-6}$-cycloalkylamino each of which is optionally substituted with one or more halogens; and $X_4$ is arylene or heteroarylene each of which is optionally substituted with one or more substituents selected from
    halogen, hydroxy, cyano, amino or carboxy; or
    $C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, $C_{3-6}$-cycloalkylthio, $C_{1-6}$-alkylamino, $C_{1-6}$-dialkylamino or $C_{3-6}$-cycloalkylamino each of which is optionally substituted with one or more halogens; and Ar is arylene which is optionally substituted with one or more substituents selected from
    halogen, hydroxy or cyano; or
    $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; and $Y_1$ is O or S; and $Y_2$ is O or S; and Z is —$(CH_2)_n$— wherein n is 1, 2 or 3; and $R_1$ is hydrogen, halogen or a substituent selected from
    $C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-1}$-alkylthio, arylthio or $C_{3-6}$-cycloalkylthio each of which is optionally substituted with one or more halogens; and $R_2$ is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or a pharmaceutically acceptable salt thereof, or a pharmaceutically acceptable solvate thereof, or any tautomeric forms, stereoisomers, mixture of stereoisomers including a racemic mixture, or polymorphs.

In one embodiment, the present invention is concerned with compounds of formula (I) wherein $X_1$ is aryl optionally substituted with one or more substituents selected from
halogen; or
$C_{1-6}$-alkyl, aryl, $C_{1-6}$-alkoxy or $C_{1-6}$-alkylsulfonyl each of which is optionally substituted with one or more halogens.

In another embodiment, the present invention is concerned with compounds of formula (I) wherein XI is aryl optionally substituted with one or more substituents selected from
halogen; or
$C_{1-6}$-alkyl optionally substituted with one or more halogens.

In another embodiment, the present invention is concerned with compounds of formula (I) wherein $X_1$ is phenyl optionally substituted with one or more substituents selected from
halogen; or
$C_{1-6}$-alkyl, aryl, $C_{1-6}$-alkoxy or $C_{1-6}$-alkylsulfonyl each of which is optionally substituted with one or more halogens.

In another embodiment, the present invention is concerned with compounds of formula (I) wherein $X_1$ is phenyl optionally substituted with one or more substituents selected from
halogen; or
$C_{1-6}$-alkyl optionally substituted with one or more halogens.

In another embodiment, the present invention is concerned with compounds of formula (I) wherein $X_1$ is heteroaryl optionally substituted with one or more substituents selected from halogen; or $C_{1-6}$-alkyl, aryl, $C_{1-6}$-alkoxy or $C_{1-6}$-alkylsulfonyl each of which is optionally substituted with one or more halogens.

In another embodiment, the present invention is concerned with compounds of formula (I) wherein $X_1$ is heteroaryl optionally substituted with one or more substituents selected from halogen; or $C_{1-6}$-alkyl optionally substituted with one or more halogens.

In another embodiment, the present invention is concerned with compounds of formula (I) wherein $X_1$ is furyl or thienyl optionally substituted with one or more halogens.

In another embodiment, the present invention is concerned with compounds of formula (I) wherein $X_2$ is arylene optionally substituted with one or more substituents selected from halogen or $C_{1-6}$-alkyl optionally substituted with one or more halogens.

In another embodiment, the present invention is concerned with compounds of formula (I) wherein $X_2$ is phenylene optionally substituted with one or more substituents selected from halogen or $C_{1-6}$-alkyl optionally substituted with one or more halogens.

In another embodiment, the present invention is concerned with compounds of formula (I) wherein $X_2$ is phenylene.

In another embodiment, the present invention is concerned with compounds of formula (I) wherein $X_3$ is aryl optionally substituted with one or more substituents selected from halogen; or $C_{1-6}$-alkyl, aryl, $C_{1-6}$-alkoxy or $C_{1-6}$-alkylsulfonyl each of which is optionally substituted with one or more halogens.

In another embodiment, the present invention is concerned with compounds of formula (I) wherein $X_3$ is aryl optionally substituted with one or more substituents selected from halogen; or $C_{1-6}$-alkyl optionally substituted with one or more halogens.

In another embodiment, the present invention is concerned with compounds of formula (I) wherein $X_3$ is phenyl optionally substituted with one or more substituents selected from halogen; or $C_{1-6}$-alkyl, aryl, $C_{1-6}$-alkoxy or $C_{1-6}$-alkylsulfonyl each of which is optionally substituted with one or more halogens.

In another embodiment, the present invention is concerned with compounds of formula (I) wherein $X_3$ is phenyl optionally substituted with one or more substituents selected from halogen; or $C_{1-6}$-alkyl optionally substituted with one or more halogens.

In another embodiment, the present invention is concerned with compounds of formula (I) wherein $X_3$ is heteroaryl optionally substituted with one or more substituents selected from halogen; or $C_{1-6}$-alkyl, aryl, $C_{1-6}$-alkoxy or $C_{1-6}$-alkylsulfonyl each of which is optionally substituted with one or more halogens.

In another embodiment, the present invention is concerned with compounds of formula (I) wherein $X_3$ is heteroaryl optionally substituted with one or more substituents selected from halogen; or $C_{1-6}$-alkyl optionally substituted with one or more halogens.

In another embodiment, the present invention is concerned with compounds of formula (I) wherein $X_3$ is furyl or thienyl optionally substituted with one or more halogens.

In another embodiment, the present invention is concerned with compounds of formula (I) wherein $X_4$ is arylene optionally substituted with one or more substituents selected from halogen or $C_{1-6}$-alkyl optionally substituted with one or more halogens.

In another embodiment, the present invention is concerned with compounds of formula (I) wherein $X_4$ is phenylene optionally substituted with one or more substituents selected from halogen or $C_{1-6}$-alkyl optionally substituted with one or more halogens.

In another embodiment, the present invention is concerned with compounds of formula (I) wherein $X_4$ is phenylene.

In another embodiment, the present invention is concerned with compounds of formula (I) wherein Ar is phenylene which is optionally substituted with one or more substituents selected from halogen, hydroxy or cyano; or $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens.

In another embodiment, the present invention is concerned with compounds of formula (I) wherein Ar is phenylene which is optionally substituted with one or more substituents selected from halogen; or $C_{1-6}$-alkyl, $C_{1-6}$-alkoxy, aryloxy or aralkoxy each of which is optionally substituted with one or more halogens.

In another embodiment, the present invention is concerned with compounds of formula (I) wherein Ar is phenylene which is optionally substituted with methyl.

In another embodiment, the present invention is concerned with compounds of formula (I) wherein Ar is phenylene.

In another embodiment, the present invention is concerned with compounds of formula (I) wherein $Y_1$ is S.

In another embodiment, the present invention is concerned with compounds of formula (I) wherein $Y_2$ is O.

In another embodiment, the present invention is concerned with compounds of formula (I) wherein n is 1.

In another embodiment, the present invention is concerned with compounds of formula (I) wherein $R_1$ is hydrogen or a substituent selected from $C_{1-6}$-alkyl, aralkyl, $C_{1-6}$-alkoxy, aryloxy, aralkoxy each of which is optionally substituted with one or more halogens.

In another embodiment, the present invention is concerned with compounds of formula (I) wherein $R_1$ is hydrogen or a substituent selected from $C_{1-6}$-alkyl, $C_{1-6}$-alkoxy each of which is optionally substituted with one or more halogens.

In another embodiment, the present invention is concerned with compounds of formula (I) wherein $R_1$ is hydrogen.

In another embodiment, the present invention is concerned with compounds of formula (I) wherein $R_2$ is hydrogen.

In another embodiment, the present invention is concerned with compounds of formula I wherein alkyl is methyl or ethyl.

In another embodiment, the present invention is concerned with compounds of formula I wherein alkenyl is vinyl or 1-propenyl.

In another embodiment, the present invention is concerned with compounds of formula I wherein alkynyl is 1-propynyl.

In another embodiment, the present invention is concerned with compounds of formula I wherein alkenynyl is 1-pentene-4-yne.

In another embodiment, the present invention is concerned with compounds of formula I wherein alkoxy is methoxy, ethoxy, isopropoxy or cyclopropoxy.

In another embodiment, the present invention is concerned with compounds of formula I wherein aryl is phenyl.

In another embodiment, the present invention is concerned with compounds of formula I wherein arylene is phenylene.

In another embodiment, the present invention is concerned with compounds of formula I wherein halogen is fluorine or chlorine.

In another embodiment, the present invention is concerned with compounds of formula I wherein perhalomethyl is trifluoromethyl.

In another embodiment, the present invention is concerned with compounds of formula I wherein perhalomethoxy is trifluoromethoxy, In another embodiment, the present invention is concerned with compounds of formula I wherein heteroaryl is furyl or thienyl.

In another embodiment, the present invention is concerned with compounds of formula I wherein aralkyl is benzyl.

In another embodiment, the present invention is concerned with compounds of formula I wherein aryloxy is phenoxy.

In another embodiment, the present invention is concerned with compounds of formula I wherein aralkoxy is benzyloxy.

In another embodiment, the present invention is concerned with compounds of formula I wherein the substituents $R_1$ and $X_4$ are arranged in a trans-configuration.

In another embodiment, the present invention is concerned with compounds of formula I wherein the substituents $R_1$ and $X_4$ are arranged in a cis-configuration.

In another embodiment, the present invention is concerned with compounds of formula I which are PPARδ agonists.

In another embodiment, the present invention is concerned with compounds of formula I which are selective PPARδ agonists.

Examples of compounds of the invention are:

[4-(3,3-Bis-biphenyl-4-yl-allylsulfanyl)-2-methyl-phenoxy]-acetic acid

[4-(3,3-Bis-biphenyl-4-yl-allyloxy)-2-methyl-phenoxy]-acetic acid (4-{3,3-Bis-[4-(5-methyl-furan-2-yl)-phenyl]-allyloxy}-2-methyl-phenoxy)-acetic acid (4-{3,3-Bis-[4-(furan-2-yl)-phenyl]-allyloxy}-2-methyl-phenoxy)-acetic acid (4-{3,3-Bis-[4-(5-methyl-furan-2-yl)-phenyl]-allylsulfanyl}-2-methyl-phenoxy)-acetic acid (4-{3,3-Bis-[4-(furan-2-yl)-phenyl]-allylsulfanyl}-2-methyl-phenoxy)-acetic acid (4-{3,3-Bis-[4-(5-chloro-thiophen-2-yl)-phenyl]-allylsulfanyl}-2-methyl-phenoxy)-acetic acid (4-{3,3-Bis-[4-(5-chloro-thiophen-2-yl)-phenyl]-allyloxy}-2-methyl-phenoxy)-acetic acid {4-[3,3-Bis-(4-thiophen-2-yl-phenyl)-allyloxy]-2-methyl-phenoxy}-acetic acid {4-[3,3-Bis-(4-thiophen-2-yl-phenyl)-allylsulfanyl]-2-methyl-phenoxy}-acetic acid (4-{3,3-Bis-[4-(5-acetyl-thiophen-2-yl)-phenyl]-allylsulfanyl}-2-methyl-phenoxy)-acetic acid (4-{3,3-Bis-[4-(5-acetyl-thiophen-2-yl)-phenyl]-allyloxy}-2-methyl-phenoxy)-acetic acid (4-{3,3-Bis-[4-(5-acetyl-thiophen-2-yl)-phenyl]-2-ethyl-allyloxy}-2-methyl-phenoxy)-acetic acid (4-{3,3-Bis-[4-(5-acetyl-thiophen-2-yl)-phenyl]-2-ethyl-allylsulfanyl}-2-methyl-phenoxy)-acetic acid {4-[3,3-Bis-(3'-dimethylcarbamoyl-biphenyl-4-yd)-allylsulfanyl]-2-methyl-phenoxy}-acetic acid {4-[3,3-Bis-(3'-dimethylcarbamoyl-biphenyl-4-yl)-allyloxy]-2-methyl-phenoxy}-acetic acid {4-[3,3-Bis-(3'-methylsulfanyl-biphenyl-4-yl)-allylsulfanyl]-2-methyl-phenoxy}-acetic acid {4-[3,3-Bis-(3'-methylsulfanyl-biphenyl-4-yl)-allyloxy]-2-methyl-phenoxy}-acetic acid {4-[3,3-Bis-(3'-amino-biphenyl-4-yl)-allyloxy]-2-methyl-phenoxy}-acetic acid {4-[3,3-Bis-(3'-amino-biphenyl-4-yl)-allylsulfanyl]-2-methyl-phenoxy}-acetic acid {4-[3,3-Bis-(4'-amino-biphenyl-4-yl)-allylsulfanyl]-2-methyl-phenoxy}-acetic acid {4-[3,3-Bis-(4'-amino-biphenyl-4-yl)-allyloxy]-2-methyl-phenoxy}-acetic acid {4-[3,3-Bis-(4-pyridin-2-yl-phenyl)-allyloxy]-2-methyl-phenoxy}-acetic acid {4-[3,3-Bis-(4-pyridin-2-yl-phenyl)-allylsulfanyl]-2-methyl-phenoxy}-acetic acid {4-[3,3-Bis-(4'-methanesulfonyl-biphenyl-4-yl)-allylsulfanyl]-2-methyl-phenoxy}-acetic acid {4-[3,3-Bis-(4'-methanesulfonyl-biphenyl-4-yl)-allyoxy]-2-methyl-phenoxy}-acetic acid {4-[3,3-Bis-(4'-methoxy-biphenyl-4-yl)-allyloxy]-2-methyl-phenoxy}-acetic acid {4-[3,3-Bis-(4'-methoxy-biphenyl-4-yl)-allylsulfanyl]-2-methyl-phenoxy}-acetic acid {4-[3,3-Bis-(4'-trifluoromethoxy-biphenyl-4-yl)-allylsulfanyl]-2-methyl-phenoxy}-acetic acid {4-[3,3-Bis-(4'-trifluoromethoxy-biphenyl-4-yl)-allyloxy]-2-methyl-phenoxy}-acetic acid {4-[3,3-Bis-(4'-methyl-biphenyl-4-yl)-allyloxy]-2-methyl-phenoxy}-acetic acid {4-[3,3-Bis-(4'-methyl-biphenyl-4-yl)-allylsulfanyl]-2-methyl-phenoxy}-acetic acid {4-[3,3-Bis-(4'-trifluoromethyl-biphenyl-4-yl)-allylsulfanyl]-2-methyl-phenoxy}-acetic acid {4-[3,3-Bis-(4'-trifluoromethyl-biphenyl-4-yl)-allyloxy]-2-methyl-phenoxy}-acetic acid {4-[3,3-Bis-(4'-chloro-biphenyl-4-yl)-allyloxy]-2-methyl-phenoxy}-acetic acid {4-[3,3-Bis-(4'-chloro-biphenyl-4-yl)-allylsulfanyl]-2-methyl-phenoxy}-acetic acid
{4-[3,3-Bis-(4'-chloro-biphenyl-4-yl)-allyloxy]-2-methyl-phenoxy}-acetic acid
{4-[3,3-Bis-(4'-tert-butyl-biphenyl-4-yl)-allyloxy]-2-methyl-phenoxy}-acetic acid
[4-(3,3-Bis-[1,1';4',1"]terphenyl-4-yl-allylsulfanyl)-2-methyl-phenoxy]-acetic acid
[4-(3,3-Bis-[1,1';4',1"]terphenyl-4-yl-allylsulfanyl)-2-methyl-phenoxy]-acetic acid
{4-[3,3-Bis-(4'-acetyl-biphenyl-4-yl)-allylsulfanyl]-2-methyl-phenoxy}-acetic acid
{4-[3,3-Bis-(4'-acetyl-biphenyl-4-yl)-allyloxy]-2-methyl-phenoxy}-acetic acid
{4-[3,3-Bis-(4'-phenoxy-biphenyl-4-yl)-allyloxy]-2-methyl-phenoxy}-acetic acid
{4-[3,3-Bis-(4'-phenoxy-biphenyl-4-yl)-allylsulfanyl]-2-methyl-phenoxy}-acetic acid
{4-[3,3-Bis-(4'-isopropyl-biphenyl-4-yl)-allylsulfanyl]-2-methyl-phenoxy}-acetic acid
{4-[3,3-Bis-(4'-isopropyl-biphenyl-4-yl)-allyloxy]-2-methyl-phenoxy}-acetic acid
{4-[3,3-Bis-(3',4'-difluoro-biphenyl-4-yl)-allyloxy]-2-methyl-phenoxy}-acetic acid
{4-[3,3-Bis-(3',4'-difluoro-biphenyl-4-yl)-allylsulfanyl]-2-methyl-phenoxy}-acetic acid
{4-[3,3-Bis-(3',5'-dichloro-biphenyl-4-yl)-allylsulfanyl]-2-methyl-phenoxy}-acetic acid
{4-[3,3-Bis-(3',5'-dichloro-biphenyl-4-yl)-allyloxy]-2-methyl-phenoxy}-acetic acid
{4-[3,3-Bis-(3'-chloro-4'-fluoro-biphenyl-4-yl)-allyloxy]-2-methyl-phenoxy}-acetic acid
{4-[3,3-Bis-(3'-chloro-4'-fluoro-biphenyl-4-yl)-allylsulfanyl]-2-methyl-phenoxy}-acetic acid
(4-{3,3-Bis-[4-(4-methyl-furan-2-yl)-phenyl]-allyloxy}-2-methyl-phenoxy)-acetic acid
(4-{3,3-Bis-[4-(4-methyl-furan-2-yl)-phenyl]-allylsulfanyl}-2-methyl-phenoxy)-acetic acid
(4-{3,3-Bis-[4-(4-chloro-thiophen-2-yl)-phenyl]-allylsulfanyl}-2-methyl-phenoxy)-acetic acid
(4-{3,3-Bis-[4-(4-chloro-thiophen-2-yl)-phenyl]-allyloxy}-2-methyl-phenoxy)-acetic acid
(4-{3,3-Bis-[4-(4-acetyl-thiophen-2-yl)-phenyl]-allylsulfanyl}-2-methyl-phenoxy)-acetic acid
(4-{3,3-Bis-[4-(4-acetyl-thiophen-2-yl)-phenyl]-allyloxy}-2-methyl-phenoxy)-acetic acid
(4-{3,3-Bis-[4-(4-acetyl-thiophen-2-yl)-phenyl]-2-ethyl-allyloxy}-2-methyl-phenoxy)-acetic acid
(4-{3,3-Bis-[4-(4-acetyl-thiophen-2-yl)-phenyl]-2-ethyl-allylsulfanyl}-2-methyl-phenoxy)-acetic acid
{4-[3,3-Bis-(4-pyridin-3-yl-phenyl)-allyloxy]-2-methyl-phenoxy}-acetic acid
{4-[3,3-Bis-(4-pyridin-3-yl-phenyl)-allylsulfanyl]-2-methyl-phenoxy}-acetic acid {4-[3,3-Bis-(4-pyridin-3-yl-phenyl)-allylsulfanyl]-2-trifluoromethyl-phenoxy}-acetic acid
{4-[3,3-Bis-(3'-dimethylcarbamoyl-biphenyl-4-yl)-allylsulfanyl]-phenoxy}-acetic acid
{4-[3,3-Bis-(3'-dimethylcarbamoyl-biphenyl-4-yl)-allyloxy]-2-methyl-phenoxy}-acetic acid
{4-[3,3-Bis-(3'-methoxy-biphenyl-4-yl)-allyloxy]-2-methyl-phenoxy}-acetic acid
{4-[3,3-Bis-(3'-methoxy-biphenyl-4-yl)-allylsulfanyl]-2-methyl-phenoxy}-acetic acid
{4-[3,3-Bis-(3'-trifluoromethoxy-biphenyl-4-yl)-allylsulfanyl]-2-methyl-phenoxy}-acetic acid
{4-[3,3-Bis-(3'-trifluoromethoxy-biphenyl-4-yl)-allyloxy]-2-methyl-phenoxy}-acetic acid
{4-[3,3-Bis-(3'-methyl-biphenyl-4-yl)-allyloxy]-2-methyl-phenoxy}-acetic acid
{4-[3,3-Bis-(3'-methyl-biphenyl-4-yd)-allylsulfanyl]-2-methyl-phenoxy}-acetic acid
{4-[3,3-Bis-(3'-trifluoromethyl-biphenyl-4-yl)-allylsulfanyl]-2-methyl-phenoxy}-acetic acid
{4-[3,3-Bis-(3'-trifluoromethyl-biphenyl-4-yd)-allyloxy]-2-methyl-phenoxy}-acetic acid
{4-[3,3-Bis-(3'-chloro-biphenyl-4-yl)-allyloxy]-2-methyl-phenoxy}-acetic acid
{4-[3,3-Bis-(3'-chloro-biphenyl-4-yl)-allylsulfanyl]-2-methyl-phenoxy}-acetic acid
{4-[3,3-Bis-(3'-chloro-biphenyl-4-yl)-allyloxy]-2-methyl-phenoxy}-acetic acid
{4-[3,3-Bis-(3'-tert-butyl-biphenyl-4-yl)-allyloxy]-2-methyl-phenoxy}-acetic acid
{4-[3,3-Bis-(3'-acetyl-biphenyl-4-yl)-allylsulfanyl]-2-methyl-phenoxy}-acetic acid
{4-[3,3-Bis-(3'-acetyl-biphenyl-4-yl)-allyloxy]-2-methyl-phenoxy}-acetic acid
{4-[3,3-Bis-(3'-phenoxy-biphenyl-4-yl)-allyloxy]-2-methyl-phenoxy}-acetic acid
{4-[3,3-Bis-(3'-phenoxy-biphenyl-4-yl)-allylsulfanyl]-2-methyl-phenoxy}-acetic acid
{4-[3,3-Bis-(3'-isopropyl-biphenyl-4-yl)-allylsulfanyl]-2-methyl-phenoxy}-acetic acid
{4-[3,3-Bis-(3'-isopropyl-biphenyl-4-yl)-allyloxy]-2-methyl-phenoxy}-acetic acid
{4-[3,3-Bis-(2',4'-difluoro-biphenyl-4-yl)-allyloxy]-2-methyl-phenoxy}-acetic acid
{4-[3,3-Bis-(2',4'-difluoro-biphenyl-4-yl)-allylsulfanyl]-2-methyl-phenoxy}-acetic acid
{4-[3,3-Bis-(2',5'-dichloro-biphenyl-4-yl)-allylsulfanyl]-2-methyl-phenoxy}-acetic acid
{4-[3,3-Bis-(2',5'-dichloro-biphenyl-4-yd)-allyloxy]-2-methyl-phenoxy}-acetic acid
{4-[3,3-Bis-(2'-chloro-4'-fluoro-biphenyl-4-yl)-allyloxy]-2-methyl-phenoxy}-acetic acid
{4-[3,3-Bis-(2'-chloro-4'-fluoro-biphenyl-4-yl)-allysulfanyl]-2-methyl-phenoxy}-acetic acid
[4-(3,3-Bis-biphenyl-4-yl-allylsulfanyl)-phenoxy]-acetic acid
[4-(3,3-Bis-biphenyl-4-yl-allyloxy)-phenoxy]-acetic acid
(4-{3,3-Bis-[4-(5-methyl-furan-2-yl)-phenyl]-allyloxy}-phenoxy)-acetic acid
(4-{3,3-Bis-[4-(furan-2-yl)-phenyl]-allyloxy}-phenoxy)-acetic acid
(4-{3,3-Bis-[4-(5-methyl-furan-2-yl)-phenyl]-allylsulfanyl}-phenoxy)-acetic acid
(4-{3,3-Bis-[4-(furan-2-yl)-phenyl]-allylsulfanyl}-phenoxy)-acetic acid
(4-{3,3-Bis-[4-(5-chloro-thiophen-2-yl)-phenyl]-allylsulfanyl}-phenoxy)-acetic acid
(4-{3,3-Bis-[4-(5-chloro-thiophen-2-yl)-phenyl]-allyloxy}-phenoxy)-acetic acid
{4-[3,3-Bis-(4-thiophen-2-yl-phenyl)-allyloxy]-phenoxy}-acetic acid
{4-[3,3-Bis-(4-thiophen-2-yl-phenyl)-allylsulfanyl]-phenoxy}-acetic acid
(4-{3,3-Bis-[4-(5-acetyl-thiophen-2-yl)-phenyl]-allylsulfanyl}-phenoxy)-acetic acid
(4-{3,3-Bis-[4-(5-acetyl-thiophen-2-yl)-phenyl]-allyloxy}-phenoxy)-acetic acid
(4-{3,3-Bis-[4-(5-acetyl-thiophen-2-yl)-phenyl]-2-ethyl-allyloxy}-phenoxy)-acetic acid (4-{3,3-Bis-[4-(5-acetyl-thiophen-2-yl)-phenyl]-2-ethyl-allylsulfanyl}-phenoxy)-acetic acid
{4-[3,3-Bis-(3'-methylsulfanyl-biphenyl-4-yl)-allylsulfanyl]-phenoxy}-acetic acid
{4-[3,3-Bis-(3'-methylsulfanyl-biphenyl-4-yl)-allyloxy]-phenoxy}-acetic acid
{4-[3,3-Bis-(3'-amino-biphenyl-4-yl)-allyloxy]-phenoxy}-acetic acid
{4-[3,3-Bis-(3'-amino-biphenyl-4-yl)-allylsulfanyl]-phenoxy}-acetic acid
{4-[3,3-Bis-(4'-amino-biphenyl-4-yl)-allylsulfanyl]-phenoxy}-acetic acid
{4-[3,3-Bis-(4'-amino-biphenyl-4-yl)-allyloxy]-phenoxy}-acetic acid
{4-[3,3-Bis-(4-pyridin-2-yl-phenyl)-allyloxy]-phenoxy}-acetic acid
{4-[3,3-Bis-(4-pyridin-2-yl-phenyl)-allylsulfanyl]-phenoxy}-acetic acid
{4-[3,3-Bis-(4'-methanesulfonyl-biphenyl-4-yl)-allylsulfanyl]-phenoxy}-acetic acid
{4-[3,3-Bis-(4'-methanesulfonyl-biphenyl-4-yl)-allyloxy]-phenoxy}-acetic acid
{4-[3,3-Bis-(4'-methoxy-biphenyl-4-yl)-allyloxy]-phenoxy}-acetic acid
{4-[3,3-Bis-(4'-methoxy-biphenyl-4-yl)-allylsulfanyl]-phenoxy}-acetic acid
{4-[3,3-Bis-(4'-trifluoromethoxy-biphenyl-4-yl)-allylsulfanyl]-phenoxy}-acetic acid
{4-[3,3-Bis-(4'-trifluoromethoxy-biphenyl-4-yl)-allyloxy]-phenoxy}-acetic acid
{4-[3,3-Bis-(4'-methyl-biphenyl-4-yl)-allyloxy]-phenoxy}-acetic acid
{4-[3,3-Bis-(4'-methyl-biphenyl-4-yl)-allylsulfanyl]-phenoxy}-acetic acid
{4-[3,3-Bis-(4'-trifluoromethyl-biphenyl-4-yl)-allylsulfanyl]-phenoxy}-acetic acid
{4-[3,3-Bis-(4'-trifluoromethyl-biphenyl-4-yl)-allyloxy]-phenoxy}-acetic acid
{4-[3,3-Bis-(4'-chloro-biphenyl-4-yl)-allyloxy]-phenoxy}-acetic acid
{4-[3,3-Bis-(4'-chloro-biphenyl-4-yl)-allylsulfanyl]-phenoxy}-acetic acid
{4-[3,3-Bis-(4'-chloro-biphenyl-4-yl)-allyloxy]-phenoxy}-acetic acid
{4-[3,3-Bis-(4'-tert-butyl-biphenyl-4-yl)-allyloxy]-phenoxy}-acetic acid
[4-(3,3-Bis-[1,1';4',1"]terphenyl-4-yl-allylsulfanyl)-phenoxy]-acetic acid
[4-(3,3-Bis-[1,1';4',1"]terphenyl-4-yl-allylsulfanyl)-phenoxy]-acetic acid
{4-[3,3-Bis-(4'-acetyl-biphenyl-4-yl)-allylsulfanyl]-phenoxy}-acetic acid
{4-[3,3-Bis-(4'-acetyl-biphenyl-4-yl)-allyloxy]-phenoxy}-acetic acid
{4-[3,3-Bis-(4'-phenoxy-biphenyl-4-yl)-allyloxy]-phenoxy}-acetic acid
{4-[3,3-Bis-(4'-phenoxy-biphenyl-4-yl)-allylsulfanyl]-phenoxy}-acetic acid
{4-[3,3-Bis-(4'-isopropyl-biphenyl-4-yl)-allylsulfanyl]-phenoxy}-acetic acid
{4-[3,3-Bis-(4'-isopropyl-biphenyl-4-yl)-allyloxy]-phenoxy}-acetic acid
{4-[3,3-Bis-(3',4'-difluoro-biphenyl-4-yl)-allyloxy]-phenoxy}-acetic acid
{4-[3,3-Bis-(3',4'-difluoro-biphenyl-4-yl)-allylsulfanyl]-phenoxy}-acetic acid
{4-[3,3-Bis-(3',5'-dichloro-biphenyl-4-yl)-allylsulfanyl]-phenoxy}-acetic acid
{4-[3,3-Bis-(3',5'-dichloro-biphenyl-4-yl)-allyloxy]-phenoxy}-acetic acid
{4-[3,3-Bis-(3'-chloro-4'-fluoro-biphenyl-4-yl)-allyloxy]-phenoxy}-acetic acid
{4-[3,3-Bis-(3'-chloro-4'-fluoro-biphenyl-4-yl)-allylsulfanyl]-phenoxy}-acetic acid
(4-{3,3-Bis-[4-(4-methyl-furan-2-yl)-phenyl]-allyloxy}-phenoxy)-acetic acid
(4-{3,3-Bis-[4-(4-methyl-furan-2-yl)-phenyl]-allylsulfanyl}-phenoxy)-acetic acid
(4-{3,3-Bis-[4-(4-chloro-thiophen-2-yl)-phenyl]-allylsulfanyl}-phenoxy)-acetic acid
(4-{3,3-Bis-[4-(4-chloro-thiophen-2-yl)-phenyl]-allyloxy}-phenoxy)-acetic acid
(4-{3,3-Bis-[4-(4-acetyl-thiophen-2-yl)-phenyl]-allylsulfanyl}-phenoxy)-acetic acid
(4-{3,3-Bis-[4-(4-acetyl-thiophen-2-yl)-phenyl]-allyloxy}-phenoxy)-acetic acid
(4-{3,3-Bis-[4-(4-acetyl-thiophen-2-yl)-phenyl]-2-ethyl-allyloxy}-phenoxy)-acetic acid
(4-{3,3-Bis-[4-(4-acetyl-thiophen-2-yl)-phenyl]-2-ethyl-allylsulfanyl}-phenoxy)-acetic acid
{4-[3,3-Bis-(4-pyridin-3-yl-phenyl)-allyloxy]-phenoxy}-acetic acid
{4-[3,3-Bis-(4-pyridin-3-yl-phenyl)-allylsulfanyl]-phenoxy}-acetic acid
{4-[3,3-Bis-(3'-methoxy-biphenyl-4-yl)-allyloxy]-phenoxy}-acetic acid
{4-[3,3-Bis-(3'-methoxy-biphenyl-4-yl)-allylsulfanyl]-phenoxy}-acetic acid
{4-[3,3-Bis-(3'-trifluoromethoxy-biphenyl-4-yl)-allylsulfanyl]-phenoxy}-acetic acid
{4-[3,3-Bis-(3'-trifluoromethoxy-biphenyl-4-yl)-allyloxy]-phenoxy}-acetic acid
{4-[3,3-Bis-(3'-methyl-biphenyl-4-yl)-allyloxy]-phenoxy}-acetic acid
{4-[3,3-Bis-(3'-methyl-biphenyl-4-yl)-allylsulfanyl]-phenoxy}-acetic acid
{4-[3,3-Bis-(3'-trifluoromethyl-biphenyl-4-yl)-allylsulfanyl]-phenoxy}-acetic acid
{4-[3,3-Bis-(3'-trifluoromethyl-biphenyl-4-yl)-allyloxy]-phenoxy}-acetic acid
{4-[3,3-Bis-(3'-chloro-biphenyl-4-yl)-allyloxy]-phenoxy}-acetic acid
{4-[3,3-Bis-(3'-chloro-biphenyl-4-yl)-allylsulfanyl]-phenoxy}-acetic acid
{4-[3,3-Bis-(3'-chloro-biphenyl-4-yl)-allyloxy]-phenoxy}-acetic acid
{4-[3,3-Bis-(3'-tert-butyl-biphenyl-4-yl)-allyloxy]-phenoxy}-acetic acid
{4-[3,3-Bis-(3'-acetyl-biphenyl-4-yl)-allylsulfanyl]-phenoxy}-acetic acid
{4-[3,3-Bis-(3'-acetyl-biphenyl-4-yl)-allyloxy]-phenoxy}-acetic acid
{4-[3,3-Bis-(3'-phenoxy-biphenyl-4-yl)-allyloxy]-phenoxy}-acetic acid
{4-[3,3-Bis-(3'-phenoxy-biphenyl-4-yl)-allylsulfanyl]-phenoxy}-acetic acid
{4-[3,3-Bis-(3'-isopropyl-biphenyl-4-yl)-allylsulfanyl]-phenoxy}-acetic acid
{4-[3,3-Bis-(3'-isopropyl-biphenyl-4-yl)-allyloxy]-phenoxy}-acetic acid
{4-[3,3-Bis-(2',4'-difluoro-biphenyl-4-yl)-allyloxy]-phenoxy}-acetic acid {4-[3,3-Bis-(2',4'-difluoro-biphenyl-4-yl)-allylsulfanyl]-phenoxy}-acetic acid
{4-[3,3-Bis-(2',5'-dichloro-biphenyl-4-yl)-allylsulfanyl]-phenoxy}-acetic acid
{4-[3,3-Bis-(2',5'-dichloro-biphenyl-4-yl)-allyloxy]-phenoxy}-acetic acid
{4-[3,3-Bis-(2'-chloro-4'-fluoro-biphenyl-4-yl)-allyloxy]-phenoxy}-acetic acid
{4-[3,3-Bis-(2'-chloro-4'-fluoro-biphenyl-4-yl)-allylsulfanyl]-phenoxy}-acetic acid
[4-(3,3-Bis-biphenyl-4-yl-2-ethyl-allysulfanyl)-2-methyl-phenoxy]-acetic acid
[4-(3,3-Bis-biphenyl-4-yl-2-ethyl-allyloxy)-2-methyl-phenoxy]-acetic acid
(4-{3,3-Bis-[4-(5-methyl-furan-2-yl)-phenyl]-2-ethyl-allyloxy}-2-methyl-phenoxy)-acetic acid
(4-{3,3-Bis-[4-(furan-2-yl)-phenyl]-2-ethyl-allyloxy}-2-methyl-phenoxy)-acetic acid
(4-{3,3-Bis-[4-(5-methyl-furan-2-yl)-phenyl]-2-ethyl-allylsulfanyl}-2-methyl-phenoxy)-acetic acid
(4-{3,3-Bis-[4-(furan-2-yl)-phenyl]-2-ethyl-allylsulfanyl}-2-methyl-phenoxy)-acetic acid
(4-{3,3-Bis-[4-(5-chloro-thiophen-2-yl)-phenyl]-2-ethyl-allylsulfanyl}-2-methyl-phenoxy)-acetic acid
(4-{3,3-Bis-[4-(5-chloro-thiophen-2-yl)-phenyl]-2-ethyl-allyloxy}-2-methyl-phenoxy)-acetic acid
{4-[3,3-Bis-(4-thiophen-2-yl-phenyl)-2-ethyl-allyloxy]-2-methyl-phenoxy}-acetic acid
{4-[3,3-Bis-(4-thiophen-2-yl-phenyl)-2-ethyl-allylsulfanyl]-2-methyl-phenoxy}-acetic acid
(4-{3,3-Bis-[4-(5-acetyl-thiophen-2-yl)-phenyl]-2-ethyl-allylsulfanyl}-2-methyl-phenoxy)-acetic acid
(4-{3,3-Bis-[4-(5-acetyl-thiophen-2-yl)-phenyl]-2-ethyl-allyloxy}-2-methyl-phenoxy)-acetic acid
(4-{3,3-Bis-[4-(5-acetyl-thiophen-2-yl)-phenyl]-2-ethyl-allyloxy}-2-methyl-phenoxy)-acetic acid
(4-{3,3-Bis-[4-(5-acetyl-thiophen-2-yl)-phenyl]-2-ethyl-allylsulfanyl}-2-methyl-phenoxy)-acetic acid
{4-[3,3-Bis-(3'-dimethylcarbamoyl-biphenyl-4-yl)-2-ethyl-allylsulfanyl]-2-methyl-phenoxy}-acetic acid
{4-[3,3-Bis-(3'-dimethylcarbamoyl-biphenyl-4-yl)-2-ethyl-allyloxy]-2-methyl-phenoxy}-acetic acid
{4-[3,3-Bis-(3'-methylsulfanyl-biphenyl-4-yl)-2-ethyl-allylsulfanyl]-2-methyl-phenoxy}-acetic acid
{4-[3,3-Bis-(3'-methylsulfanyl-biphenyl-4-yl)-2-ethyl-allyloxy]-2-methyl-phenoxy}-acetic acid
{4-[3,3-Bis-(3'-amino-biphenyl-4-yl)-2-ethyl-allyloxy]-2-methyl-phenoxy}-acetic acid
{4-[3,3-Bis-(3'-amino-biphenyl-4-yl)-2-ethyl-allylsulfanyl]-2-methyl-phenoxy}-acetic acid
{4-[3,3-Bis-(4'-amino-biphenyl-4-yl)-2-ethyl-allylsulfanyl]-2-methyl-phenoxy}-acetic acid
{4-[3,3-Bis-(4'-amino-biphenyl-4-yl)-2-ethyl-allyloxy]-2-methyl-phenoxy}-acetic acid
{4-[3,3-Bis-(4-pyridin-2-yl-phenyl)-2-ethyl-allyloxy]-2-methyl-phenoxy}-acetic acid
{4-[3,3-Bis-(4-pyridin-2-yl-phenyl)-2-ethyl-allylsulfanyl]-2-methyl-phenoxy}-acetic acid
{4-[3,3-Bis-(4'-methanesulfonyl-biphenyl-4-yl)-2-ethyl-allylsulfanyl]-2-methyl-phenoxy}-acetic acid
{4-[3,3-Bis-(4'-methanesulfonyl-biphenyl-4-yl)-2-ethyl-allyloxy]-2-methyl-phenoxy}-acetic acid
{4-[3,3-Bis-(4'-methoxy-biphenyl-4-yl)-2-ethyl-allyloxy]-2-methyl-phenoxy}-acetic acid
{4-[3,3-Bis-(4'-methoxy-biphenyl-4-yl)-2-ethyl-allylsulfanyl]-2-methyl-phenoxy}-acetic acid
{4-[3,3-Bis-(4'-trifluoromethoxy-biphenyl-4-yl)-2-ethyl-allylsulfanyl]-2-methyl-phenoxy}-acetic acid
{4-[3,3-Bis-(4'-trifluoromethoxy-biphenyl-4-yl)-2-ethyl-allyloxy]-2-methyl-phenoxy}-acetic acid
{4-[3,3-Bis-(4'-methyl-biphenyl-4-yl)-2-ethyl-allyloxy]-2-methyl-phenoxy}-acetic acid
{4-[3,3-Bis-(4'-methyl-biphenyl-4-yl)-2-ethyl-allylsulfanyl]-2-methyl-phenoxy}-acetic acid
{4-[3,3-Bis-(4'-trifluoromethyl-biphenyl-4-yl)-2-ethyl-allylsulfanyl]-2-methyl-phenoxy}-acetic acid
{4-[3,3-Bis-(4'-trifluoromethyl-biphenyl-4-yl)-2-ethyl-allyloxy]-2-methyl-phenoxy}-acetic acid
{4-[3,3-Bis-(4'-chloro-biphenyl-4-yl)-2-ethyl-allyloxy]-2-methyl-phenoxy}-acetic acid
{4-[3,3-Bis-(4'-chloro-biphenyl-4-yl)-2-ethyl-allylsulfanyl]-2-methyl-phenoxy}-acetic acid
{4-[3,3-Bis-(4'-chloro-biphenyl-4-yl)-2-ethyl-allyloxy]-2-methyl-phenoxy}-acetic acid
{4-[3,3-Bis-(4'-tert-butyl-biphenyl-4-yl)-2-ethyl-allyloxy]-2-methyl-phenoxy}-acetic acid
[4-(3,3-Bis-[1,1';4',1"]terphenyl-4-yl-2-ethyl-allylsulfanyl)-2-methyl-phenoxy]-acetic acid
[4-(3,3-Bis-[1,1';4',1"]terphenyl-4-yl-2-ethyl-allylsulfanyl)-2-methyl-phenoxy]-acetic acid
{4-[3,3-Bis-(4'-acetyl-biphenyl-4-yl)-2-ethyl-allylsulfanyl]-2-methyl-phenoxy}-acetic acid
{4-[3,3-Bis-(4'-acetyl-biphenyl-4-yl)-2-ethyl-allyloxy]-2-methyl-phenoxy}-acetic acid
{4-[3,3-Bis-(4'-phenoxy-biphenyl-4-yl)-2-ethyl-allyloxy]-2-methyl-phenoxy}-acetic acid
{4-[3,3-Bis-(4'-phenoxy-biphenyl-4-yl)-2-ethyl-allylsulfanyl]-2-methyl-phenoxy}-acetic acid
{4-[3,3-Bis-(4'-isopropyl-biphenyl-4-yl)-2-ethyl-allylsulfanyl]-2-methyl-phenoxy}-acetic acid
{4-[3,3-Bis-(4'-isopropyl-biphenyl-4-yl)-2-ethyl-allyloxy]-2-methyl-phenoxy}-acetic acid
{4-[3,3-Bis-(3',4'-difluoro-biphenyl-4-yl)-2-ethyl-allyloxy]-2-methyl-phenoxy}-acetic acid
{4-[3,3-Bis-(3',4'-difluoro-biphenyl-4-yl)-2-ethyl-allylsulfanyl]-2-methyl-phenoxy}-acetic acid
{4-[3,3-Bis-(3',5'-dichloro-biphenyl-4-yl)-2-ethyl-allylsulfanyl]-2-methyl-phenoxy}-acetic acid
{4-[3,3-Bis-(3',5'-dichloro-biphenyl-4-yl)-2-ethyl-allyloxy]-2-methyl-phenoxy}-acetic acid
{4-[3,3-Bis-(3'-chloro-4'-fluoro-biphenyl-4-yl)-2-ethyl-allyloxy]-2-methyl-phenoxy}-acetic acid
{4-[3,3-Bis-(3'-chloro-4'-fluoro-biphenyl-4-yl)-2-ethyl-allylsulfanyl]-2-methyl-phenoxy}-acetic acid
(4-{3,3-Bis-[4-(4-methyl-furan-2-yl)-phenyl]-2-ethyl-allyloxy}-2-methyl-phenoxy)-acetic acid
(4-{3,3-Bis-[4-(4-methyl-furan-2-yl)-phenyl]-2-ethyl-allylsulfanyl}-2-methyl-phenoxy)-acetic acid
(4-{3,3-Bis-[4-(4-chloro-thiophen-2-yl)-phenyl]-2-ethyl-allylsulfanyl}-2-methyl-phenoxy)-acetic acid
(4-{3,3-Bis-[4-(4-chloro-thiophen-2-yl)-phenyl]-2-ethyl-allyloxy}-2-methyl-phenoxy)-acetic acid
(4-{3,3-Bis-[4-(4-acetyl-thiophen-2-yl)-phenyl]-2-ethyl-allylsulfanyl}-2-methyl-phenoxy)-acetic acid
(4-{3,3-Bis-[4-(4-acetyl-thiophen-2-yl)-phenyl]-2-ethyl-allyloxy}-2-methyl-phenoxy)-acetic acid
{4-[3,3-Bis-(4-pyridin-3-yl-phenyl)-2-ethyl-allyloxy]-2-methyl-phenoxy}-acetic acid
{4-[3,3-Bis-(4-pyridin-3-yl-phenyl)-2-ethyl-allylsulfanyl]-2-methyl-phenoxy}-acetic acid
{4-[3,3-Bis-(3'-methoxy-biphenyl-4-yl)-2-ethyl-allyloxy]-2-methyl-phenoxy}-acetic acid {4-[3,3-Bis-(3'-methoxy-biphenyl-4-yl)-2-ethyl-allylsulfanyl]-2-methyl-phenoxy}-acetic acid
{4-[3,3-Bis-(3'-trifluoromethoxy-biphenyl-4-yl)-2-ethyl-allylsulfanyl]-2-methyl-phenoxy}-acetic acid
{4-[3,3-Bis-(3'-trifluoromethoxy-biphenyl-4-yl)-2-ethyl-allyloxy]-2-methyl-phenoxy}-acetic acid
{4-[3,3-Bis-(3'-methyl-biphenyl-4-yl)-2-ethyl-allyloxy]-2-methyl-phenoxy}-acetic acid
{4-[3,3-Bis-(3'-methyl-biphenyl-4-yl)-2-ethyl-allylsulfanyl]-2-methyl-phenoxy}-acetic acid
{4-[3,3-Bis-(3'-trifluoromethyl-biphenyl-4-yl)-2-ethyl-allylsulfanyl]-2-methyl-phenoxy}-acetic acid
{4-[3,3-Bis-(3'-trifluoromethyl-biphenyl-4-yl)-2-ethyl-allyloxy]-2-methyl-phenoxy}-acetic acid
{4-[3,3-Bis-(3'-chloro-biphenyl-4-yl)-2-ethyl-allyloxy]-2-methyl-phenoxy}-acetic acid
{4-[3,3-Bis-(3'-chloro-biphenyl-4-yl)-2-ethyl-allylsulfanyl]-2-methyl-phenoxy}-acetic acid
{4-[3,3-Bis-(3'-chloro-biphenyl-4-yl)-2-ethyl-allyloxy]-2-methyl-phenoxy}-acetic acid
{4-[3,3-Bis-(3'-tert-butyl-biphenyl-4-yl)-2-ethyl-allyloxy]-2-methyl-phenoxy}-acetic acid
{4-[3,3-Bis-(3'-acetyl-biphenyl-4-yl)-2-ethyl-allylsulfanyl]-2-methyl-phenoxy}-acetic acid
{4-[3,3-Bis-(3'-acetyl-biphenyl-4-yl)-2-ethyl-allyloxy]-2-methyl-phenoxy}-acetic acid
{4-[3,3-Bis-(3'-phenoxy-biphenyl-4-yl)-2-ethyl-allyloxy]-2-methyl-phenoxy}-acetic acid
{4-[3,3-Bis-(3'-phenoxy-biphenyl-4-yl)-2-ethyl-allylsulfanyl]-2-methyl-phenoxy}-acetic acid
{4-[3,3-Bis-(3'-isopropyl-biphenyl-4-yl)-2-ethyl-allylsulfanyl]-2-methyl-phenoxy}-acetic acid
{4-[3,3-Bis-(3'-isopropyl-biphenyl-4-yl)-2-ethyl-allyloxy]-2-methyl-phenoxy}-acetic acid
{4-[3,3-Bis-(2',4'-difluoro-biphenyl-4-yl)-2-ethyl-allyloxy]-2-methyl-phenoxy}-acetic acid
{4-[3,3-Bis-(2',4'-difluoro-biphenyl-4-yl)-2-ethyl-allylsulfanyl]-2-methyl-phenoxy}-acetic acid
{4-[3,3-Bis-(2',5'-dichloro-biphenyl-4-yl)-2-ethyl-allylsulfanyl]-2-methyl-phenoxy}-acetic acid
{4-[3,3-Bis-(2',5'-dichloro-biphenyl-4-yl)-2-ethyl-allyloxy]-2-methyl-phenoxy}-acetic acid
{4-[3,3-Bis-(2'-chloro-4'-fluoro-biphenyl-4-yl)-2-ethyl-allyloxy]-2-methyl-phenoxy}-acetic acid
{4-[3,3-Bis-(2'-chloro-4'-fluoro-biphenyl-4-yl)-2-ethyl-allylsulfanyl]-2-methyl-phenoxy}-acetic acid
[4-(3,3-Bis-biphenyl-4-yl-2-ethoxy-allylsulfanyl)-2-methyl-phenoxy]-acetic acid
[4-(3,3-Bis-biphenyl-4-yl-2-ethoxy-allyloxy)-2-methyl-phenoxy]-acetic acid
(4-{3,3-Bis-[4-(5-methyl-furan-2-yl)-phenyl]-2-ethoxy-allyloxy}-2-methyl-phenoxy)-acetic acid
(4-{3,3-Bis-[4-(furan-2-yl)-phenyl]-2-ethoxy-allyloxy}-2-methyl-phenoxy)-acetic acid
(4-{3,3-Bis-[4-(5-methyl-furan-2-yl)-phenyl]-2-ethoxy-allylsulfanyl}-2-methyl-phenoxy)-acetic acid
(4-{3,3-Bis-[4-(furan-2-yl)-phenyl]-2-ethoxy-allylsulfanyl}-2-methyl-phenoxy)-acetic acid(4-{3,3-Bis-[4-(5-chloro-thiophen-2-yl)-phenyl]-2-ethoxy-allylsulfanyl}-2-methyl-phenoxy)-acetic acid
(4-{3,3-Bis-[4-(5-chloro-thiophen-2-yl)-phenyl]-2-ethoxy-allyloxy}-2-methyl-phenoxy)-acetic acid
{4-[3,3-Bis-(4-thiophen-2-yl-phenyl)-2-ethoxy-allyloxy]-2-methyl-phenoxy}-acetic acid
{4-[3,3-Bis-(4-thiophen-2-yl-phenyl)-2-ethoxy-allylsulfanyl]-2-methyl-phenoxy}-acetic acid
(4-{3,3-Bis-[4-(5-acetyl-thiophen-2-yl)-phenyl]-2-ethoxy-allylsulfanyl}-2-methyl-phenoxy)-acetic acid
(4-{3,3-Bis-[4-(5-acetyl-thiophen-2-yl)-phenyl]-2-ethoxy-allyloxy}-2-methyl-phenoxy)-acetic acid
(4-{3,3-Bis-[4-(5-acetyl-thiophen-2-yl)-phenyl]-2-ethoxy-allyloxy}-2-methyl-phenoxy)-acetic acid
(4-{3,3-Bis-[4-(5-acetyl-thiophen-2-yl)-phenyl]-2-ethoxy-allylsulfanyl}-2-methyl-phenoxy)-acetic acid
{4-[3,3-Bis-(3'-methylsulfanyl-biphenyl-4-yl)-2-ethoxy-allylsulfanyl]-2-methyl-phenoxy}-acetic acid
{4-[3,3-Bis-(3'-methylsulfanyl-biphenyl-4-yl)-2-ethoxy-allyloxy]-2-methyl-phenoxy}-acetic acid
{4-[3,3-Bis-(3'-amino-biphenyl-4-yl)-2-ethoxy-allyloxy]-2-methyl-phenoxy}-acetic acid
{4-[3,3-Bis-(3'-amino-biphenyl-4-yl)-2-ethoxy-allylsulfanyl]-2-methyl-phenoxy}-acetic acid
{4-[3,3-Bis-(4'-amino-biphenyl-4-yl)-2-ethoxy-allylsulfanyl]-2-methyl-phenoxy}-acetic acid
{4-[3,3-Bis-(4'-amino-biphenyl-4-yl)-2-ethoxy-allyloxy]-2-methyl-phenoxy}-acetic acid
{4-[3,3-Bis-(4-pyridin-2-yl-phenyl)-2-ethoxy-allyloxy]-2-methyl-phenoxy}-acetic acid
{4-[3,3-Bis-(4-pyridin-2-yl-phenyl)-2-ethoxy-allylsulfanyl]-2-methyl-phenoxy}-acetic acid
{4-[3,3-Bis-(4'-methanesulfonyl-biphenyl-4-yl)-2-ethoxy-allylsulfanyl]-2-methyl-phenoxy}-acetic acid
{4-[3,3-Bis-(4'-methanesulfonyl-biphenyl-4-yl)-2-ethoxy-allyloxy]-2-methyl-phenoxy}-acetic acid
{4-[3,3-Bis-(3'-dimethylcarbamoyl-biphenyl-4-yl)-2-ethoxy-allylsulfanyl]-2-methyl-phenoxy}-acetic acid
{4-[3,3-Bis-(3'-dimethylcarbamoyl-biphenyl-4-yl)-2-ethoxy-allyloxy]-2-methyl-phenoxy}-acetic acid
{4-[3,3-Bis-(4'-methoxy-biphenyl-4-yl)-2-ethoxy-allyloxy]-2-methyl-phenoxy}-acetic acid
{4-[3,3-Bis-(4'-methoxy-biphenyl-4-yl)-2-ethoxy-allylsulfanyl]-2-methyl-phenoxy}-acetic acid
{4-[3,3-Bis-(4'-trifluoromethoxy-biphenyl-4-yl)-2-ethoxy-allylsulfanyl]-2-methyl-phenoxy}-acetic acid
{4-[3,3-Bis-(4'-trifluoromethoxy-biphenyl-4-yl)-2-ethoxy-allyloxy]-2-methyl-phenoxy}-acetic acid
{4-[3,3-Bis-(4'-methyl-biphenyl-4-yl)-2-ethoxy-allyloxy]-2-methyl-phenoxy}-acetic acid
{4-[3,3-Bis-(4'-methyl-biphenyl-4-yl)-2-ethoxy-allylsulfanyl]-2-methyl-phenoxy}-acetic acid
{4-[3,3-Bis-(4'-trifluoromethyl-biphenyl-4-yl)-2-ethoxy-allylsulfanyl]-2-methyl-phenoxy}-acetic acid
{4-[3,3-Bis-(4'-trifluoromethyl-biphenyl-4-yl)-2-ethoxy-allyloxy]-2-methyl-phenoxy}-acetic acid
{4-[3,3-Bis-(4'-chloro-biphenyl-4-yl)-2-ethoxy-allyloxy]-2-methyl-phenoxy}-acetic acid
{4-[3,3-Bis-(4'-chloro-biphenyl-4-yl)-2-ethoxy-allylsulfanyl]-2-methyl-phenoxy}-acetic acid
{4-[3,3-Bis-(4'-chloro-biphenyl-4-yl)-2-ethoxy-allyloxy]-2-methyl-phenoxy}-acetic acid
{4-[3,3-Bis-(4'-tert-butyl-biphenyl-4-yl)-2-ethoxy-allyloxy]-2-methyl-phenoxy}-acetic acid
[4-(3,3-Bis-[1,1';4',1"]terphenyl-4-yl-2-ethoxy-allylsulfanyl)-2-methyl-phenoxy]-acetic acid
[4-(3,3-Bis-[1,1';4',1"]terphenyl-4-yl-2-ethoxy-allylsulfanyl)-2-methyl-phenoxy]-acetic acid
{4-[3,3-Bis-(4'-acetyl-biphenyl-4-yl)-2-ethoxy-allylsulfanyl]-2-methyl-phenoxy}-acetic acid
{4-[3,3-Bis-(4'-acetyl-biphenyl-4-yl)-2-ethoxy-allyloxy]-2-methyl-phenoxy}-acetic acid
{4-[3,3-Bis-(4'-phenoxy-biphenyl-4-yl)-2-ethoxy-allyloxy]-2-methyl-phenoxy}-acetic acid {4-[3,3-Bis-(4'-phenoxy-biphenyl-4-yl)-2-ethoxy-allylsulfanyl]-2-methyl-phenoxy}-acetic acid
{4-[3,3-Bis-(4'-isopropyl-biphenyl-4-yl)-2-ethoxy-allylsulfanyl]-2-methyl-phenoxy}-acetic acid
{4-[3,3-Bis-(4'-isopropyl-biphenyl-4-yl)-2-ethoxy-allyloxy]-2-methyl-phenoxy}-acetic acid
{4-[3,3-Bis-(3',4'-difluoro-biphenyl-4-yl)-2-ethoxy-allyloxy]-2-methyl-phenoxy}-acetic acid
{4-[3,3-Bis-(3',4'-difluoro-biphenyl-4-yl)-2-ethoxy-allylsulfanyl]-2-methyl-phenoxy}-acetic acid
{4-[3,3-Bis-(3',5'-dichloro-biphenyl-4-yl)-2-ethoxy-allylsulfanyl]-2-methyl-phenoxy}-acetic acid
{4-[3,3-Bis-(3',5'-dichloro-biphenyl-4-yl)-2-ethoxy-allyloxy]-2-methyl-phenoxy}-acetic acid
{4-[3,3-Bis-(3'-chloro-4'-fluoro-biphenyl-4-yl)-2-ethoxy-allyloxy]-2-methyl-phenoxy}-acetic acid
{4-[3,3-Bis-(3'-chloro-4'-fluoro-biphenyl-4-yl)-2-ethoxy-allylsulfanyl]-2-methyl-phenoxy}-acetic acid
(4-{3,3-Bis-[4-(4-methyl-furan-2-yl)-phenyl]-2-ethoxy-allyloxy}-2-methyl-phenoxy)-acetic acid
(4-{3,3-Bis-[4-(4-methyl-furan-2-yl)-phenyl]-2-ethoxy-allylsulfanyl}-2-methyl-phenoxy)-acetic acid
(4-{3,3-Bis-[4-(4-chloro-thiophen-2-yl)-phenyl]-2-ethoxy-allylsulfanyl}-2-methyl-phenoxy)-acetic acid
(4-{3,3-Bis-[4-(4-chloro-thiophen-2-yl)-phenyl]-2-ethoxy-allyloxy}-2-methyl-phenoxy)-acetic acid
(4-{3,3-Bis-[4-(4-acetyl-thiophen-2-yl)-phenyl]-2-ethoxy-allylsulfanyl}-2-methyl-phenoxy)-acetic acid
(4-{3,3-Bis-[4-(4-acetyl-thiophen-2-yl)-phenyl]-2-ethoxy-allyloxy}-2-methyl-phenoxy)-acetic acid
(4-{3,3-Bis-[4-(4-acetyl-thiophen-2-yl)-phenyl] 2-ethoxy-allyloxy}-2-methyl-phenoxy)-acetic acid
(4-{3,3-Bis-[4-(4-acetyl-thiophen-2-yl)-phenyl]-2-ethoxy-allylsulfanyl}-2-methyl-phenoxy)-acetic acid
{4-[3,3-Bis-(4-pyridin-3-yl-phenyl)-2-ethoxy-allyloxy]-2-methyl-phenoxy}-acetic acid
{4-[3,3-Bis-(4-pyridin-3-yl-phenyl)-2-ethoxy-allylsulfanyl]-2-methyl-phenoxy}-acetic acid
{4-[3,3-Bis-(3'-methoxy-biphenyl-4-yl)-2-ethoxy-allyloxy]-2-methyl-phenoxy}-acetic acid
{4-[3,3-Bis-(3'-methoxy-biphenyl-4-yl)-2-ethoxy-allylsulfanyl]-2-methyl-phenoxy}-acetic acid
{4-[3,3-Bis-(3'-trifluoromethoxy-biphenyl-4-yl)-2-ethoxy-allylsulfanyl]-2-methyl-phenoxy}-acetic acid
{4-[3,3-Bis-(3'-trifluoromethoxy-biphenyl-4-yl)-2-ethoxy-allyloxy]-2-methyl-phenoxy}-acetic acid
{4-[3,3-Bis-(3'-methyl-biphenyl-4-yl)-2-ethoxy-allyloxy]-2-methyl-phenoxy}-acetic acid
{4-[3,3-Bis-(3'-methyl-biphenyl-4-yl)-2-ethoxy-allylsulfanyl]-2-methyl-phenoxy}-acetic acid
{4-[3,3-Bis-(3'-trifluoromethyl-biphenyl-4-yl)-2-ethoxy-allylsulfanyl]-2-methyl-phenoxy}-acetic acid
{4-[3,3-Bis-(3'-trifluoromethyl-biphenyl-4-yl)-2-ethoxy-allyloxy]-2-methyl-phenoxy}-acetic acid
{4-[3,3-Bis-(3'-chloro-biphenyl-4-yl)-2-ethoxy-allyloxy]-2-methyl-phenoxy}-acetic acid
{4-[3,3-Bis-(3'-chloro-biphenyl-4-yl)-2-ethoxy-allylsulfanyl]-2-methyl-phenoxy}-acetic acid
{4-[3,3-Bis-(3'-chloro-biphenyl-4-yl)-2-ethoxy-allyloxy]-2-methyl-phenoxy}-acetic acid
{4-[3,3-Bis-(3'-tert-butyl-biphenyl-4-yl)-2-ethoxy-allyloxy]-2-methyl-phenoxy}-acetic acid
{4-[3,3-Bis-(3'-acetyl-biphenyl-4-yl)-2-ethoxy-allylsulfanyl]-2-methyl-phenoxy}-acetic acid
{4-[3,3-Bis-(3'-acetyl-biphenyl-4-yl)-2-ethoxy-allyloxy]-2-methyl-phenoxy}-acetic acid
{4-[3,3-Bis-(3'-phenoxy-biphenyl-4-yl)-2-ethoxy-allyloxy]-2-methyl-phenoxy}-acetic acid
{4-[3,3-Bis-(3'-phenoxy-biphenyl-4-yl)-2-ethoxy-allylsulfanyl]-2-methyl-phenoxy}-acetic acid
{4-[3,3-Bis-(3'-isopropyl-biphenyl-4-yl)-2-ethoxy-allylsulfanyl]-2-methyl-phenoxy}-acetic acid
{4-[3,3-Bis-(3'-isopropyl-biphenyl-4-yl)-2-ethoxy-allyloxy]-2-methyl-phenoxy}-acetic acid
{4-[3,3-Bis-(2',4'-difluoro-biphenyl-4-yl)-2-ethoxy-allyloxy]-2-methyl-phenoxy}-acetic acid
{4-[3,3-Bis-(2',4'-difluoro-biphenyl-4-yl)-2-ethoxy-allylsulfanyl]-2-methyl-phenoxy}-acetic acid
{4-[3,3-Bis-(2',5'-dichloro-biphenyl-4-yl)-2-ethoxy-allylsulfanyl]-2-methyl-phenoxy}-acetic acid
{4-[3,3-Bis-(2',5'-dichloro-biphenyl-4-yl)-2-ethoxy-allyloxy]-2-methyl-phenoxy}-acetic acid
{4-[3,3-Bis-(2'-chloro-4'-fluoro-biphenyl-4-yl)-2-ethoxy-allyloxy]-2-methyl-phenoxy}-acetic acid
{4-[3,3-Bis-(2'-chloro-4'-fluoro-biphenyl-4-yl)-2-ethoxy-allylsulfanyl]-2-methyl-phenoxy}-acetic acid
[4-(3,3-Bis-biphenyl-4-yl-allylsulfanyl)-2-chloro-phenoxy]-acetic acid
[4-(3,3-Bis-biphenyl-4-yl-allyloxy)-2-chloro-phenoxy]-acetic acid
(4-{3,3-Bis-[4-(5-methyl-furan-2-yl)-phenyl]-allyloxy}-2-chloro-phenoxy)-acetic acid
(4-{3,3-Bis-[4-(-furan-2-yl)-phenyl]-allyloxy}-2-chloro-phenoxy)-acetic acid
(4-{3,3-Bis-[4-(5-methyl-furan-2-yl)-phenyl]-allylsulfanyl}-2-chloro-phenoxy)-acetic acid
(4-{3,3-Bis-[4-(furan-2-yl)-phenyl]-allylsulfanyl}-2-chloro-phenoxy)-acetic acid
(4-{3,3-Bis-[4-(5-chloro-thiophen-2-yl)-phenyl]-allylsulfanyl}-2-chloro-phenoxy)-acetic acid
(4-{3,3-Bis-[4-(5-chloro-thiophen-2-yl)-phenyl]-allyloxy}-2-chloro-phenoxy)-acetic acid
{4-[3,3-Bis-(4-thiophen-2-yl-phenyl)-allyloxy]-2-chloro-phenoxy}-acetic acid
{4-[3,3-Bis-(4-thiophen-2-yl-phenyl)-allylsulfanyl]-2-chloro-phenoxy}-acetic acid
(4-{3,3-Bis-[4-(5-acetyl-thiophen-2-yl)-phenyl]-allylsulfanyl}-2-chloro-phenoxy)-acetic acid
(4-{3,3-Bis-[4-(5-acetyl-thiophen-2-yl)-phenyl]-allyloxy}-2-chloro-phenoxy)-acetic acid
(4-{3,3-Bis-[4-(5-acetyl-thiophen-2-yl)-phenyl]-2-ethyl-allyloxy}-2-chloro-phenoxy)-acetic acid
(4-{3,3-Bis-[4-(5-acetyl-thiophen-2-yl)-phenyl]-2-ethyl-allylsulfanyl}-2-chloro-phenoxy)-acetic acid
{4-[3,3-Bis-(3'-methylsulfanyl-biphenyl-4-yl)-allylsulfanyl]-2-chloro-phenoxy}-acetic acid
{4-[3,3-Bis-(3'-methylsulfanyl-biphenyl-4-yl)-allyloxy]-2-chloro-phenoxy}-acetic acid
{4-[3,3-Bis-(3'-amino-biphenyl-4-yl)-allyloxy]-2-chloro-phenoxy}-acetic acid
{4-[3,3-Bis-(3'-amino-biphenyl-4-yl)-allylsulfanyl]-2-chloro-phenoxy}-acetic acid
{4-[3,3-Bis-(4'-amino-biphenyl-4-yl)-allylsulfanyl]-2-chloro-phenoxy}-acetic acid
{4-[3,3-Bis-(4'-amino-biphenyl-4-yl)-allyloxy]-2-chloro-phenoxy}-acetic acid
{4-[3,3-Bis-(4-pyridin-2-yl-phenyl)-allyloxy]-2-chloro-phenoxy}-acetic acid
{4-[3,3-Bis-(4-pyridin-2-yl-phenyl)-allylsulfanyl]-2-chloro-phenoxy}-acetic acid
{4-[3,3-Bis-(4'-methanesulfonyl-biphenyl-4-yl)-allylsulfanyl]-2-chloro-phenoxy}-acetic acid {4-[3,3-Bis-(4'-methanesulfonyl-biphenyl-4-yl)-allyloxy]-2-chloro-phenoxy}-acetic acid {4-[3,3-Bis-(4'-methoxy-biphenyl-4-yl)-allyloxy]-2-chloro-phenoxy}-acetic acid {4-[3,3-Bis-(4'-methoxy-biphenyl-4-yl)-allylsulfanyl]-2-chloro-phenoxy}-acetic acid {4-[3,3-Bis-(4'-trifluoromethoxy-biphenyl-4-yl)-allylsulfanyl]-2-chloro-phenoxy}-acetic acid {4-[3,3-Bis-(4'-trifluoromethoxy-biphenyl-4-yl)-allyloxy]-2-chloro-phenoxy}-acetic acid {4-[3,3-Bis-(4'-methyl-biphenyl-4-yl)-allyloxy]-2-methyl-phenoxy}-acetic acid {4-[3,3-Bis-(4'-methyl-biphenyl-4-yl)-allylsulfanyl]-2-chloro-phenoxy}-acetic acid {4-[3,3-Bis-(4'-trifluoromethyl-biphenyl-4-yl)-allylsulfanyl]-2-chloro-phenoxy}-acetic acid {4-[3,3-Bis-(4'-trifluoromethyl-biphenyl-4-yl)-allyloxy]-2-chloro-phenoxy}-acetic acid {4-[3,3-Bis-(4'-chloro-biphenyl-4-yl)-allyloxy]-2-chloro-phenoxy}-acetic acid {4-[3,3-Bis-(4'-chloro-biphenyl-4-yl)-allylsulfanyl]-2-chloro-phenoxy}-acetic acid {4-[3,3-Bis-(4'-chloro-biphenyl-4-yl)-allyloxy]-2-chloro-phenoxy}-acetic acid {4-[3,3-Bis-(4'-tert-butyl-biphenyl-4-yl)-allyloxy]-2-chloro-phenoxy}-acetic acid

[4-(3,3-Bis-[1,1';4',1"]terphenyl-4-yl-allylsulfanyl)-2-chloro-phenoxy]-acetic acid

[4-(3,3-Bis-[1,1';4',1"]terphenyl-4-yl-allylsulfanyl)-2-chloro-phenoxy]-acetic acid {4-[3,3-Bis-(4'-acetyl-biphenyl-4-yl)-allylsulfanyl]-2-chloro-phenoxy}-acetic acid {4-[3,3-Bis-(4'-acetyl-biphenyl-4-yl)-allyloxy]-2-methyl-phenoxy}-acetic acid {4-[3,3-Bis-(4'-phenoxy-biphenyl-4-yl)-allyloxy]-2-chloro-phenoxy}-acetic acid {4-[3,3-Bis-(4'-phenoxy-biphenyl-4-yl)-allylsulfanyl]-2-chloro-phenoxy}-acetic acid {4-[3,3-Bis-(4'-isopropyl-biphenyl-4-yl)-allylsulfanyl]-2-chloro-phenoxy}-acetic acid {4-[3,3-Bis-(4'-isopropyl-biphenyl-4-yl)-allyloxy]-2-chloro-phenoxy}-acetic acid {4-[3,3-Bis-(3',4'-difluoro-biphenyl-4-yl)-allyloxy]-2-chloro-phenoxy}-acetic acid {4-[3,3-Bis-(3',4'-difluoro-biphenyl-4-yl)-allylsulfanyl]-2-chloro-phenoxy}-acetic acid {4-[3,3-Bis-(3',5'-dichloro-biphenyl-4-yl)-allylsulfanyl]-2-chloro-phenoxy}-acetic acid {4-[3,3-Bis-(3',5'-dichloro-biphenyl-4-yl)-allyloxy]-2-chloro-phenoxy}-acetic acid {4-[3,3-Bis-(3'-chloro-4'-fluoro-biphenyl-4-yl)-allyloxy]-2-chloro-phenoxy}-acetic acid {4-[3,3-Bis-(3'-chloro-4'-fluoro-biphenyl-4-yl)-allylsulfanyl]-2-chloro-phenoxy}-acetic acid or a salt thereof with a pharmaceutically acceptable acid or base, or any optical isomer or mixture of optical isomers, including a racemic mixture, or any tautomeric forms.

The present invention also encompasses pharmaceutically acceptable salts of the present compounds. Such salts include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium, zinc, calcium salts and the like. Examples of amines and organic amines include ammonium, methylamine, dimethylamine, trimethylamine, ethylamine, diethylamine, propylamine, butylamine, tetramethylamine, ethanolamine, diethanolamine, triethanolamine, meglumine, ethylenediamine, choline, N,N'-dibenzylethylenediamine, N-benzylphenylethylamine, N-methyl-D-glucamine, guanidine and the like. Examples of cationic amino acids include lysine, arginine, histidine and the like.

The pharmaceutically acceptable salts are prepared by reacting the compound of formula I with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixture of solvents may be used. Organic bases like lysine, arginine, diethanolamine, choline, guandine and their derivatives etc. may also be used. Alternatively, acid addition salts wherever applicable are prepared by treatment with acids such as hydrochloric acid, hydrobromic acid, nitric acid, sulfuric acid, phosphoric acid, p-toluenesulphonic acid, methanesulfonic acid, acetic acid, citric acid, maleic acid salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane etc. Mixture of solvents may also be used.

The stereoisomers of the compounds forming part of this invention may be prepared by using reactants in their single enantiomeric form in the process wherever possible or by conducting the reaction in the presence of reagents or catalysts in their single enantiomer form or by resolving the mixture of stereoisomers by conventional methods. Some of the preferred methods include use of microbial resolution, enzymatic resolution, resolving the diastereomeric salts formed with chiral acids such as mandelic acid, camphorsulfonic acid, tartaric acid, lactic acid, and the like wherever applicable or chiral bases such as brucine, (R)- or (S)-phenylethylamine, cinchona alkaloids and their derivatives and the like. Commonly used methods are compiled by Jaques et al in "Enantiomers, Racemates and Resolution" (Wiley Interscience, 1981). More specifically the compound of formula I may be converted to a 1:1 mixture of diastereomeric amides by treating with chiral amines, aminoacids, aminoalcohols derived from aminoacids; conventional reaction conditions may be employed to convert acid into an amide; the dia-stereomers may be separated either by fractional crystallization or chromatography and the stereoisomers of compound of formula I may be prepared by hydrolysing the pure diastereomeric amide.

Various polymorphs of compound of general formula I forming part of this invention may be prepared by crystallization of compound of formula I under different conditions. For example, using different solvents commonly used or their mixtures for recrystallization; crystallizations at different temperatures; various modes of cooling, ranging from very fast to very slow cooling during crystallizations. Polymorphs may also be obtained by heating or melting the compound followed by gradual or fast cooling. The presence of polymorphs may be determined by solid probe nmr spectroscopy, ir spectroscopy, differential scanning calorimetry, powder X-ray diffraction or such other techniques.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of compounds of the general formula I or their tautomeric forms, their stereoisomers, their polymorphs, their pharmaceutically acceptable salts or pharmaceutically acceptable solvates thereof for the preparation of a pharmaceutical composition for the treatment and/or prevention of conditions mediated by nuclear receptors, in particular the Peroxisome Proliferator-Activated Receptors (PPAR) such as the conditions mentioned above.

In another aspect, the present invention relates to a method of treating and/or preventing Type I or Type II diabetes.

In a still further aspect, the present invention relates to the use of one or more compounds of the general formula I or pharmaceutically acceptable salts thereof for the preparation of a pharmaceutical composition for the treatment and/or prevention of Type I or Type II diabetes.

In a still further aspect, the present compounds are useful for the treatment and/or prevention of IGT.

In a still further aspect, the present compounds are useful for the treatment and/or prevention of Type 2 diabetes.

In a still further aspect, the present compounds are useful for the delaying or prevention of the progression from IGT to Type 2 diabetes.

In a still further aspect, the present compounds are useful for the delaying or prevention of the progression from non-insulin requiring Type 2 diabetes to insulin requiring Type 2 diabetes.

In another aspect, the present compounds reduce blood glucose and triglyceride levels and are accordingly useful for the treatment and/or prevention of ailments and disorders such as diabetes and/or obesity.

In still another aspect, the present compounds are useful for the treatment and/or prophylaxis of insulin resistance (Type 2 diabetes), impaired glucose tolerance, dyslipidemia, disorders related to Syndrome X such as hypertension, obesity, insulin resistance, hyperglycaemia, atherosclerosis, hyperlipidemia, coronary artery disease, myocardial ischemia and other cardiovascular disorders.

In still another aspect, the present compounds are effective in decreasing apoptosis in mammalian cells such as beta cells of Islets of Langerhans.

In still another aspect, the present compounds are useful for the treatment of certain renal diseases including glomerulonephritis, glomerulosclerosis, nephrotic syndrome, hypertensive nephrosclerosis.

In still another aspect, the present compounds may also be useful for improving cognitive functions in dementia, treating diabetic complications, psoriasis, polycystic ovarian syndrome (PCOS) and prevention and treatment of bone loss, e.g. osteoporosis.

The present compounds may also be administered in combination with one or more further pharmacologically active substances eg., selected from antiobesity agents, antidiabetics, antihypertensive agents, agents for the treatment and/or prevention of complications resulting from or associated with diabetes and agents for the treatment and/or prevention of complications and disorders resulting from or associated with obesity.

Thus, in a further aspect of the invention the present compounds may be administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline re-uptake inhibitors, mixed serotonin and noradrenergic compounds, 5HT (serotonin) agonists, bombesin agonists, galanin antagonists, growth hormone, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, RXR (retinoid X receptor) modulators or TR β agonists.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

Suitable antidiabetics comprise insulin, GLP-1 (glucagon like peptide-1) derivatives such as those disclosed in WO 98/08871 to Novo Nordisk A/S, which is incorporated herein by reference as well as orally active hypoglycaemic agents.

The orally active hypoglycaemic agents preferably comprise sulphonylureas, biguanides, meglitinides, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, DPP-IV (dipeptidyl peptidase-IV) inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents as HMG CoA inhibitors (statins), compounds lowering food intake, RXR agonists and agents acting on the ATP-dependent potassium channel of the β-cells.

In one embodiment of the invention the present compounds are administered in combination with insulin.

In a further embodiment the present compounds are administered in combination with a sulphonylurea eg. tolbutamide, glibenclamide, glipizide or glicazide.

In another embodiment the present compounds are administered in combination with a biguanide eg. metformin.

In yet another embodiment the present compounds are administered in combination with a meglitinide eg. repaglinide or senaglinide.

In a further embodiment the present compounds are administered in combination with an α-glucosidase inhibitor eg. miglitol or acarbose.

In another embodiment the present compounds are administered in combination with an agent acting on the ATP-dependent potassium channel of the β-cells eg. tolbutamide, glibenclamide, glipizide, glicazide or repaglinide.

Furthermore, the present compounds may be administered in combination with nateglinide.

In still another embodiment the present compounds are administered in combination with an antihyperlipidemic agent or antilipidemic agent eg. cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds eg. in combination with a sulphonylurea and metformin, a sulphonylurea and acarbose, repaglinide and metformin, insulin and a sulphonylurea, insulin and metformin, insulin, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

The present invention also relates to a process for the preparation of the above said novel compounds, their derivatives, their analogs, their tautomeric forms, their stereoisomers, their polymorphs, their pharmaceutically acceptable salts or pharmaceutically acceptable solvates.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995. The compositions may appear in conventional forms, for example capsules, tablets, aerosols, solutions, suspensions or topical applications.

Typical compositions include a compound of formula I or a pharmaceutically acceptable acid addition salt thereof, associated with a pharmaceutically acceptable excipient which may be a carrier or a diluent or be diluted by a carrier, or enclosed within a carrier which can be in the form of a capsule, sachet, paper or other container. In making the compositions, conventional techniques for the preparation of pharmaceutical compositions may be used. For example, the active compound will usually be mixed with a carrier, or diluted by a carrier, or enclosed within a carrier which may be in the form of a ampoule, capsule, sachet, paper, or other container. When the carrier serves as a diluent, it may be solid, semi-solid, or liquid material which acts as a vehicle, excipient, or medium for the active compound. The active compound can be adsorbed on a granular solid container for example in a sachet. Some examples of suitable carriers are water, salt solutions, alcohols, polyethylene glycols, polyhydroxyethoxylated castor oil, peanut oil, olive oil, gelatine, lactose, terra alba, sucrose, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone. Similarly, the carrier or diluent may include any sustained release material known in the art, such as glyceryl monostearate or glyceryl distearate, alone or mixed with a wax. The formulations may also include wetting agents, emulsifying and suspending agents, preserving agents, sweetening agents or flavouring agents. The formulations of the invention may be formulated so as to provide quick, sustained, or delayed release of the active ingredient after administration to the patient by employing procedures well known in the art.

The pharmaceutical compositions can be sterilized and mixed, if desired, with auxiliary agents, emulsifiers, salt for influencing osmotic pressure, buffers and/or colouring substances and the like, which do not deleteriously react with the active compounds.

The route of administration may be any route, which effectively transports the active compound to the appropriate or desired site of action, such as oral, nasal, pulmonary, transdermal or parenteral e.g. rectal, depot, subcutaneous, intravenous, intraurethral, intramuscular, intranasal, ophthalmic solution or an ointment, the oral route being preferred.

If a solid carrier is used for oral administration, the preparation may be tabletted, placed in a hard gelatin capsule in powder or pellet form or it can be in the form of a troche or lozenge. If a liquid carrier is used, the preparation may be in the form of a syrup, emulsion, soft gelatin capsule or sterile injectable liquid such as an aqueous or non-aqueous liquid suspension or solution.

For nasal administration, the preparation may contain a compound of formula I dissolved or suspended in a liquid carrier, in particular an aqueous carrier, for aerosol application. The carrier may contain additives such as solubilizing agents, e.g. propylene glycol, surfactants, absorption enhancers such as lecithin (phosphatidylcholine) or cyclodextrin, or preservatives such as parabenes.

For parenteral application, particularly suitable are injectable solutions or suspensions, preferably aqueous solutions with the active compound dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

A typical tablet which may be prepared by conventional tabletting techniques may contain:

| Core: | |
| --- | --- |
| Active compound (as free compound or salt thereof) | 5 mg |
| Colloidal silicon dioxide (Aerosil) | 1.5 mg |
| Cellulose, microcryst. (Avicel) | 70 mg |
| Modified cellulose gum (Ac-Di-Sol) | 7.5 mg |
| Magnesium stearate | Ad. |
| Coating: | |
| HPMC approx. | 9 mg |
| *Mywacett 9–40 T approx. | 0.9 mg |

*Acylated monoglyceride used as plasticizer for film coating.

If desired, the pharmaceutical composition of the invention may comprise the compound of formula (I) in combination with further pharmacologically active substances such as those described in the foregoing.

The compounds of the invention may be administered to a mammal, especially a human in need of such treatment, prevention, elimination, alleviation or amelioration of diseases related to the regulation of blood sugar.

Such mammals include also animals, both domestic animals, e.g. household pets, and non-domestic animals such as wildlife.

The compounds of the invention are effective over a wide dosage range. A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

Any novel feature or combination of features described herein is considered essential to this invention.

The invention also relate to methods of preparing the above mentioned compounds, comprising:

General Procedure (A)

Step A:

Reacting a compound of formula II

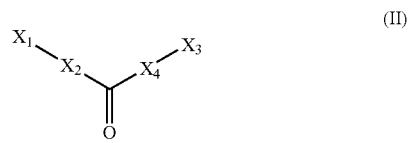

wherein $X_1$, $X_2$, $X_3$ and $X_4$ are defined as above, through a Wittig-like process with for example $(EtO)_2PO(CHR_1)COOR_6$ (wherein $R_6$ is an alkyl group), in the presence of a base such as sodium hydride, EtONa and the like to give a compound of formula III

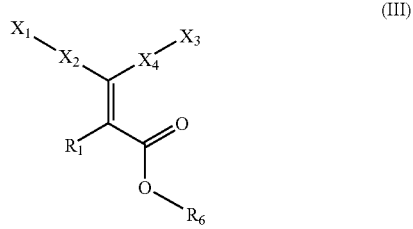

wherein $X_1$, $X_2$, $X_3$, $X_4$, $R_1$ and $R_6$ are defined as above

Step B:

Reducing the compound of formula III, wherein $X_1$, $X_2$, $X_3$, $X_4$, $R_1$ and $R_6$ are defined as above with a suitable reagent such as diisobutylaluminium hydride, to give a compound of formula IV

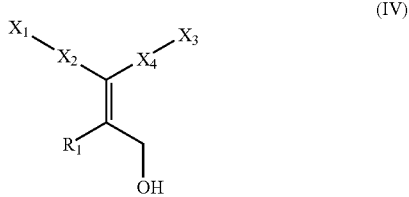

wherein $X_1$, $X_2$, $X_3$, $X_4$ and $R_1$ are defined as above, and

Step C:

Reacting the compound of formula IV, wherein $X_1$, $X_2$, $X_3$, $X_4$, and $R_1$ are defined as above, (except that when $X_1$, $X_2$, $X_3$ or $X_4$, are substituted with hydroxy, this functionality has to be protected) with a compound of formula V

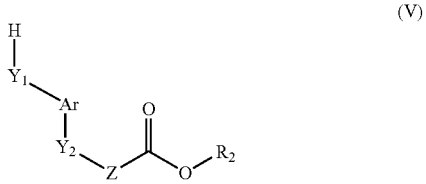

wherein $Y_1$, Ar, $Y_2$, Z and $R_2$ are defined as above, except that $R_2$ is not hydrogen under Mitsunobu conditions, using a reagent such as triphenylphosphine/diethylazodicarboxylate and the like to obtain a compound of formula I, wherein $X_1$, $X_2$, $X_3$, $X_4$, $Y_1$, $Y_2$, Ar, Z, $R_1$ and $R_2$ are defined as above, except that $R_2$ is not hydrogen.

General Procedure (B)

Step A:

Converting the —OH functionality in the compound of formula IV, wherein $X_1$, $X_2$, $X_3$, $X_4$, and $R_1$ are defined as above, to an appropriate leaving group (L) such as p-toluenesulfonate, methanesulfonate, halogen (for example by methods according to: Houben-Weyl, Methoden der organischen Chemie, Alkohole III, 6/1 b, Thieme-Verlag 1984, 4th Ed., pp. 927–939; Comprehensive Organic Transformations. A guide to functional group preparations, VCH Publishers 1989, 1$^{st}$ Ed., pp. 353–363 and *J. Org. Chem.*, Vol. 36 (20), 3044–3045, 1971), triflate and the like, to give a compound of formula VI

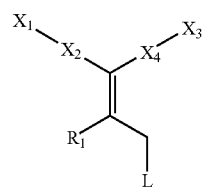

wherein, $X_1$, $X_2$, $X_3$, $X_4$, $R_1$ and L are defined as above.

Step B:

Reacting the compound of formula VI wherein L is a leaving group such as p-toluenesulfonate, methanesulfonate, halogen, triflate and the like and wherein $X_1$, $X_2$, $X_3$, $X_4$ and $R_1$ are defined as above with a compound of formula V wherein $Y_1$, Ar, $Y_2$, Z and $R_2$ are defined as above, except that $R_2$ is not hydrogen to give a compound of formula I wherein $X_1$, $X_2$, $X_3$, $X_4$, $Y_1$, $Y_2$, Ar, Z, $R_1$ and $R_2$ are defined as above, except that $R_2$ is not hydrogen.

General Procedure (C)

Step A:

Reacting an compound of formula VII

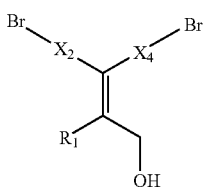

wherein $X_2$, $X_4$ and $R_1$ are defined as above, with an boronic acid derivative of $X_1$ or $X_3$ under appropriate coupling conditions as Pd2(dba)3/Pd(P(t-Bu)3)2/KF/THF, to give a compound of formula IV, wherein $X_1$, $X_2$, $X_3$, $X_4$ and $R_1$ are defined as above, and Step B:

Reacting a compound of formula IV as described inder procedure A step C, to obtain a compound of formula I, wherein $X_1$, $X_2$, $X_3$, $X_4$, $Y_1$, $Y_2$, Ar, Z, $R_1$ and $R_2$ are defined as above, except that $R_2$ is not hydrogen.

General Procedure (D)

Step A:

By chemical or enzymatic saponification of a compound of formula I wherein $X_1$, $X_2$, $X_3$, $X_4$, $Y_1$, $Y_2$, Ar, Z, $R_1$ and $R_2$ are defined as above, except that $R_2$ is not hydrogen to give a compound of formula I wherein $X_1$, $X_2$, $X_3$, $X_4$, $Y_1$, $Y_2$, Ar, Z, $R_1$ and $R_2$ are defined as above, except that $R_2$ is hydrogen.

General Procedure (E)

Step A:

Reacting a compound of formula VII, wherein $X_2$, $X_4$ and $R_1$ are defined as above, with a compound of formula V, wherein $Y_1$, Ar, $Y_2$, Z and $R_2$ are defined as above, except that $R_2$ is not hydrogen under Mitsunobu conditions, using a reagent such as triphenylphosphine/diethylazodicarboxylate and the like to obtain a compound of formula VIII

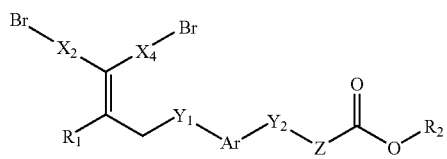

wherein $X_2$, $X_4$, $Y_1$, $Y_2$, Ar, Z, $R_1$ and $R_2$ are defined as above, except that $R_2$ is not hydrogen.

Step B:

By chemical or enzymatic saponification of a compound of formula VIII wherein $X_2$, $X_4$, $Y_1$, $Y_2$, Ar, Z, $R_1$ and $R_2$ are defined as above, except that $R_2$ is not hydrogen, to give a compound of formula VIII wherein $X_2$, $X_4$, $Y_1$, $Y_2$, Ar, Z, $R_1$ and $R_2$ are defined as above, except that $R_2$ is hydrogen.

Step C:

Reacting a compound of formula VIII, wherein $X_2$, $X_4$, $Y_1$, $Y_2$, Ar, Z, $R_1$ and $R_2$ are defined as above, with an boronic acid derivative of $X_1$ or $X_3$ under appropriate coupling conditions as Pd2(dba)3/Pd(P(t-Bu)3)2/KF/THF, to give a compound of formula I, wherein $X_1$, $X_2$, $X_3$, $X_4$, $Y_1$, $Y_2$, Ar, Z, $R_1$ and $R_2$ are defined as above.

EXAMPLE 1

General Procedure (E)

[4-(3,3-Bis-biphenyl-4-yl-allylsulfanyl)-2-methyl-phenoxy]-acetic acid

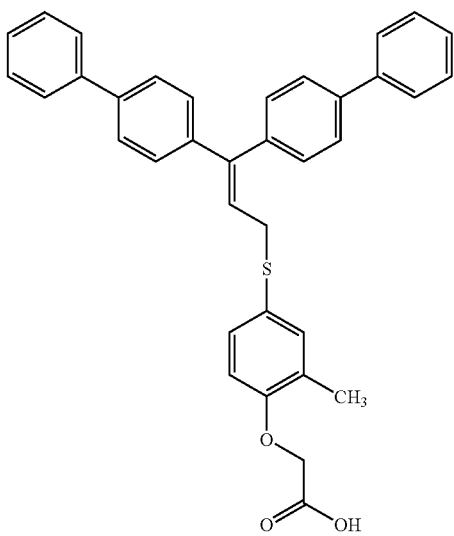

Step A:

To a solution of NaH (3.53 g, 88.2 mmol) in dry toluene (300 ml) was added dropwise at 0° C. a solution of trietylphosphonoacetate (13.2 g, 58.8 mmol) in toluene (100 ml). The reaction mixture was stirred for 30 min. after which a solution of 4,4-dibromobenzophenone (10.0 g, 29.4 mmol) in THF (100 ml) was added. The reaction mixture was stirred for 48 h. Ethanol (10 ml) and water (300 ml) were added and the mixture was extracted with ethyl acetate-methanol (2%, 2×150 ml). The combined organic phases were washed with brine, dried with MgSO$_4$, filtered and evaporated. The residue was purified by column chromatography (eluent: ether) to give ethyl 3,3-bis-(4-bromophenyl)-acrylate as a gum. Crystallization from hexanes gave white crystals in 8.77 g (73%) yield.

$^1$H NMR (CDCl$_3$, 300 MHz); δ 1.20 (3H, t), 4.05 (2H, q), 6.35 (1H, s), 7.0–7.1 (4H, dm), 7.40–7.52 (4H, dm).

Ethyl 3,3-bis-(4-bromophenyl)-acrylate (8.75 g, 21.3 mmol) was dissolved in dry THF (35 ml). DIBAL-H (1.5 M in toluene, 43 ml, 64.0 mmol) was added at −15° C. and the reaction mixture was stirred for 30 min. A solution of ammonium chloride in water was added and the mixture was extracted with ethyl acetate (3×50 ml). The combined organic phases were washed with brine, dried with MgSO$_4$, filtered and evaporated to give 3,3-bis-(4-bromophenyl)-pro-2-en-1-ol in 6.0 g (76%) yield.

$^1$H NMR (CDCl$_3$, 300 MHz); δ 1.15 (1H, br s), 4.16–4.20 (2H, dd), 6.25 (1H, t), 7.0–7.1 (4H, dm), 7.40–7.52 (4H, dm).

3,3-Bis-(4-bromophenyl)-pro-2-en-1-ol (2.98 g, 8.1 mmol) and tributylphosphine (2.4 g, 12.1 mmol) were dissolved in dry THF (150 ml) and cooled to 0° C. under an atmosphere of nitrogen. 1,1'-(Azodicarbonyl)dipiperidine (ADDP) (3.1 g, 12.1 mmol) was added and the reaction mixture was stirred for 5 min. (4-Mercapto-2-methyl-phenoxy)-acetic acid methyl ester (2.06 g, 9.7 mmol; Bioorg. Med. Chem. Lett. 2003, 13, 1517) was slowly added (5 min) and the stirring continued for 2 h at 0° C. Water (100 ml) was added and the mixture was extracted with dichloromethane (2×150 ml). The combined organic phases were dried with MgSO$_4$, filtered and evaporated. The residue was purified by column chromatography (eluent: dichloromethane) to give 4.0 g (88%) of {4-[3,3-bis-(4-bromo-phenyl)-allylsulfanyl]-2-methyl-phenoxy}-acetic acid methyl ester.

$^1$H NMR (CDCl$_3$, 300 MHz); δ 2.20 (3H, s), 3.44 (2H, d), 3.78 (3H, s), 4.64 (2H, s), 6.11 (1H, t), 6.55 (1H, d), 6.73 (2H, d), 6.98 (2H, d), 7.10 (2H, bs), 7.38 (2H, d), 7.43 (2H, d).

Step B:

A solution of {4-[3,3-bis-(4-bromo-phenyl)-allylsulfanyl]-2-methyl-phenoxy}-acetic acid methyl ester (530 mg, 0.94 mmol) in ethanol (20 ml) and 1M NaOH (2.0 ml, 2.0 mmol) was stirred at room temp. for 2 h. The reaction mixture added water (20 ml) and 1N HCl (3.0 ml). The water phase was extracted with dichloromethane (2×50 ml) and the combined organic phases were dried with MgSO$_4$, filtered and evaporated to give 482 mg (93%) of {4-[3,3-bis-(4-bromo-phenyl)-allylsulfanyl]-2-methyl-phenoxy}-acetic acid.

$^1$H NMR (CDCl$_3$, 300 MHz) δ2.20 (3H, s), 3.45 (2H, d), 4.68 (2H, s), 6.10 (1H, t), 6.58 (1H, d), 6.75 (2H, d), 6.98 (2H, d), 7.10–7.13 (2H, m), 7.38 (2H, d), 7.43 (2H, d).

Step C:

In an evaporated schlenk flask kept under nitrogen atmosphere were added {4-[3,3-bis-(4-bromo-phenyl)-allylsulfanyl]-2-methyl-phenoxy}-acetic acid (297 mg, 0.54 mmol), phenylboronic acid (152 mg, 1.2 mmol), KF (104 mg, 1.79 mmol), Pd$_2$(dba)$_3$ (30 mg, 33 mmol) and Pd(P(t-Bu)$_3$)$_2$ (33 mg, 65 mmol). THF (6 ml) was added to the solid mixture keeping the mixture under nitrogen. The reaction mixture was stirred at room temperature for 1 h, followed by 4 h at 50° C. A saturated solution of ammonium chloride (5 ml) was added, and the mixture was extracted with dichloromethane (2×20 ml). The organic phases were dried and evaporated. The residue was purified by column chromatography (eluent: dichloromethane:THF (8:3)) to give the title compound in 155 mg (53%) yield.

$^1$H NMR (CDCl$_3$, 300 MHz) δ 2.22 (3H, s), 3.61 (2H, d), 4.60 (2H, s), 6.21 (1H, t), 6.59 (1H, d), 7.00–7.77 (20H, m).

EXAMPLE 2

General Procedure (E)

{4-[3,3-Bis-(4'-methanesulfonyl-biphenyl-4-yl)-allylsulfanyl]-2-methyl-phenoxy}-acetic acid

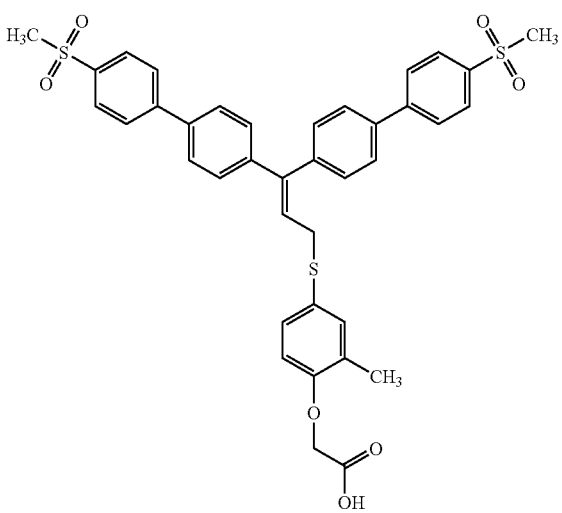

Step C:

In an evaporated schlenk flask kept under nitrogen atmosphere were added {4-[3,3-bis-(4-bromo-phenyl)-allylsulfanyl]-2-methyl-phenoxy}-acetic acid (208 mg, 0.38 mmol, example 1, step A–B), 4-(methansulfonyl)phenylboronic acid (280 mg, 1.4 mmol), KF (77 mg, 1.33 mmol), Pd$_2$(dba)$_3$ (21 mg, 23 mmol) and Pd(P(t-BU)$_3$)$_2$ (23 mg, 46 mmol). THF (5 ml) was added to the solid mixture keeping the mixture under nitrogen. The reaction mixture was stirred at room temperature for 1 h, followed by 4 h at 50° C. A saturated solution of ammonium chloride (5 ml) was added, and the mixture was extracted with dichloromethane (2×20 ml). The organic phases were dried and evaporated. The residue was purified by column chromatography (eluent: ethyl acetate:methanol (9:1)) to give the title compound in 95 mg (36%) yield.

$^1$H NMR (CDCl$_3$, 300 MHz) δ 2.18 (3H, s), 3.10 (3H, s), 3.12 (3H, s), 3.57 (2H, d), 4.62 (2H, s), 6.26 (1H, t), 6.60 (1H, d), 7.12 (4H, m), 7.31 (2H, d), 7.53 (2H, d), 7.85 (2H, d), 7.74 (2H, d), 7.81 (2H, d), 8.00 (4H, m).

EXAMPLE 3

General Procedure (E)

{4-[3,3-Bis-(3'-trifluoromethyl-biphenyl-4-yl)-allyl-sulfanyl]-2-methyl-phenoxy}-acetic acid

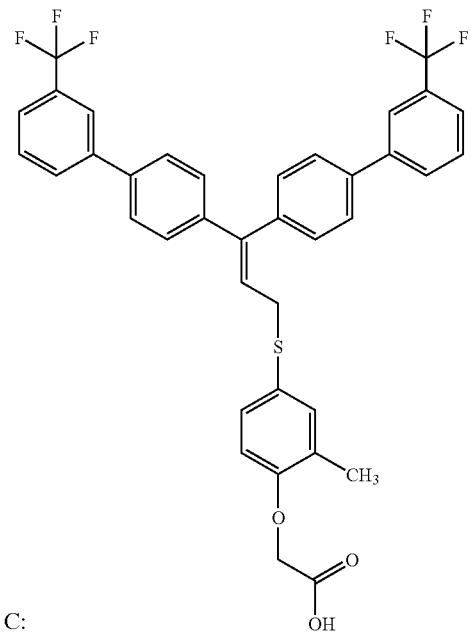

Step C:

In an evaporated schlenk flask kept under nitrogen atmosphere were added {4-[3,3-bis-(4-bromo-phenyl)-allylsulfanyl]-2-methyl-phenoxy}-acetic acid (231 mg, 0.42 mmol, example 1, step A–B), 3-(trifluoromethyl)phenylboronic acid (203 mg, 1.1 mmol), KF (81 mg, 1.39 mmol), Pd$_2$(dba)$_3$ (23 mg, 25 mmol) and Pd(P(t-Bu)$_3$)$_2$ (26 mg, 51 mmol). THF (5 ml) was added to the solid mixture keeping the mixture under nitrogen. The reaction mixture was stirred at room temperature for 1 h, followed by 10 h at 50° C. A saturated solution of ammonium chloride (5 ml) was added, and the mixture was extracted with dichloromethane (2×20 ml). The organic phases were dried and evaporated. The residue was purified by HPLC to give the title compound in 140 mg (49%) yield.

$^1$H NMR (CDCl$_3$, 300 MHz) δ 2.22 (3H, s), 3.59 (2H, d), 4.66 (2H, s), 6.24 (1H, t), 6.61 (1H, d), 7.08–7.90 (18H, m).

EXAMPLE 4

General Procedure (E)

[4-(3,3-Bis-[1,1';4',1"]terphenyl-4-yl-allylsulfanyl)-2-methyl-phenoxy]-acetic acid

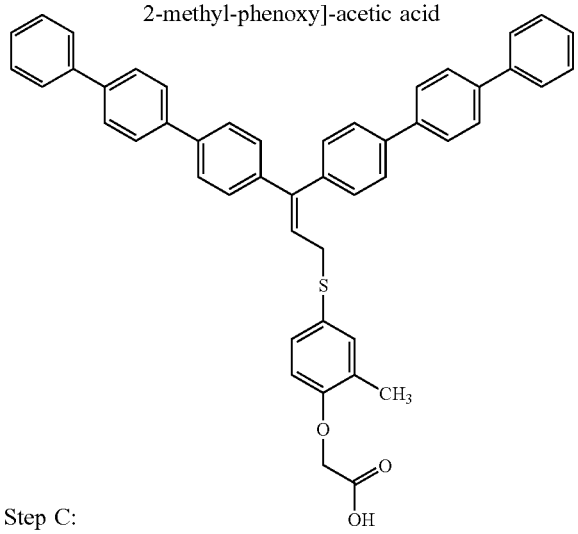

Step C:

In an evaporated schlenk flask kept under nitrogen atmosphere were added {4-[3,3-bis-(4-bromo-phenyl)-allylsulfanyl]-2-methyl-phenoxy}-acetic acid (225 mg, 0.41 mmol, example 1, step A–B, biphenylboronic acid (163 mg, 0.8 mmol), KF (79 mg, 1.35 mmol), Pd$_2$(dba)$_3$ (23 mg, 25 mmol) and Pd(P(t-Bu)$_3$)$_2$ (26 mg, 51 mmol). THF (6 ml) was added to the solid mixture keeping the mixture under nitrogen. The reaction mixture was stirred at 50° C. for 2 h, followed by 10 h at 70° C. A saturated solution of ammonium chloride (5 ml) was added, and the mixture was extracted with dichloromethane (2×20 ml). The organic phases were dried and evaporated. The residue was purified by HPLC to give the title compound in 55 mg (19%) yield.

$^1$H NMR (DMSO, 300 MHz) δ 2.12 (3H, s), 3.60 (2H, d), 4.68 (2H, s), 6.24 (1H, t), 6.77 (1H, d), 7.02–7.90 (28H, m).

EXAMPLE 5

General Procedure (E)

{4-[3,3-Bis-(3'-dimethylcarbamoyl-biphenyl-4-yl)-allylsulfanyl]-2-methyl-phenoxy}-acetic acid

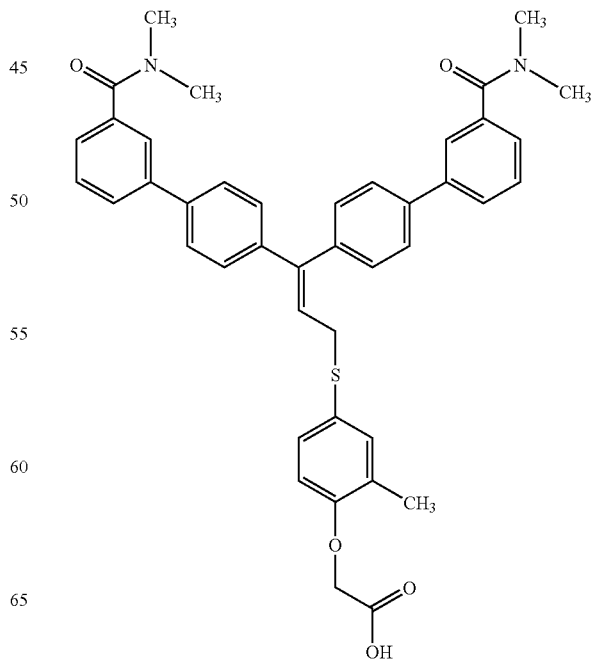

Step C:

In an evaporated schlenk flask kept under nitrogen atmosphere were added {4-[3,3-bis-(4-bromo-phenyl)-allylsulfanyl]-2-methyl-phenoxy}-acetic acid (225 mg, 0.41 mmol, example 1, step A–B), N,N-dimethylbenzamide-3-boronic acid (182 mg, 0.94 mmol), KF (79 mg, 1.35 mmol), Pd$_2$(dba)$_3$ (23 mg, 25 mmol) and Pd(P(t-Bu)$_3$)$_2$ (26 mg, 51 mmol). THF (6 ml) was added to the solid mixture keeping the mixture under nitrogen. The reaction mixture was stirred at room temperature for 1 h, followed by 1 h at 50° C. A saturated solution of ammonium chloride (5 ml) was added, and the mixture was extracted with dichloromethane (3×20 ml). The organic phases were dried and evaporated. The residue was purified by column chromatography (eluent: dichloromethane:methanol (9:1)) to give the title compound in 90 mg (32%) yield.

$^1$H NMR (CDCl$_3$, 300 MHz) δ 2.19 (3H, s), 2.99 (3H, s), 3.07 (3H, s), 3.14 (3H, s), 3.17 (3H,s), 3.48 (2H, d), 4.57 (2H, s), 6.25 (1H, t), 6.64 (1H, d), 6.74 (2H, d), 6.93 (1H, d), 7.17–8.00 (15H, m).

EXAMPLE 6

General Procedure (E)

{4-[3,3-Bis-(4-pyridin-3-yl-phenyl)-allylsulfanyl]-2-methyl-phenoxy}-acetic acid

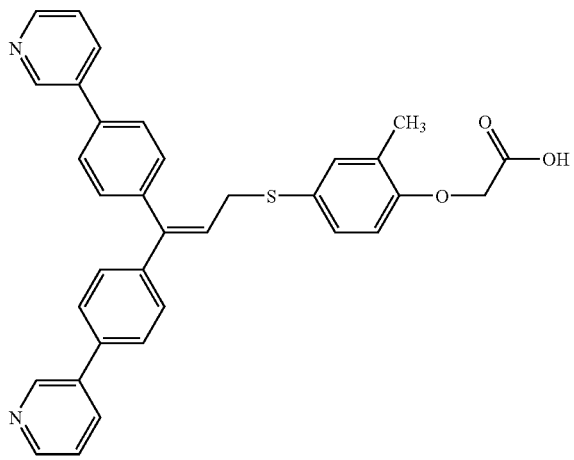

Step C:

In a vial for micro wave oven was added under nitrogen {4-[3,3-bis-(4-bromophenyl)-allylsulfanyl]-2-methyl-phenoxy}-acetic acid (175 mg, 0.34 mmol, example 1, step A–B), pyridine-3-boronic acid (91 mg, 0.74 mmol), sodium carbonate (215 mg, 2.0 mmol), Pd(PPh$_3$)$_2$Cl (15 mg, 0.02 mmol), dimethyl ether (2.9 ml), water (1.25 ml) and ethanol (99%, 0.8 ml). The reaction was run for 5 min at 140° C. in the micro wave oven. The reaction was filtered and the filtrate evaporated. The residue was purified by column chromatography (eluent: dichloromethane:methanol (4:1)) to give the title compound in 102 mg (56%) yield.

$^1$H NMR (MeOD, 400 MHz) δ 2.17 (3H, s), 3.55 (2H, d), 4.49 (2H, s), 6.36 (1H, t), 6.68 (1H, d), 7.00–7–65 (12H, m), 8.03–8.14 (2H, m), 8.51 (2H, m), 8.77 (1H, s), 8.85 (1H, s).

EXAMPLE 7

{4-[3,3-Bis-(4-pyridin-3-yl-phenyl)-allylsulfanyl]-2-trifluoromethyl-phenoxy}-acetic acid

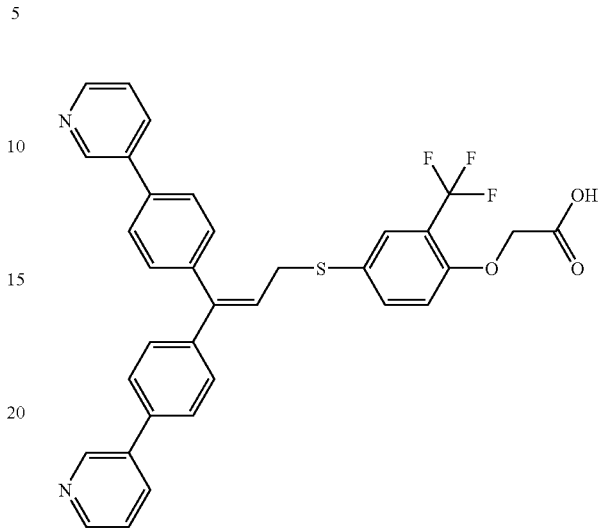

Step A:

To a 0° C. solution of triethylphosphonoacetate (11.7 g, 52.4 mmol) in THF (230 ml) was added over 5 min a solution of NaH 60% in oil (2.6 g; 109 mmol). The reaction mixture was stirred for 30 min after which 4,4-diiodobenzophenone (18.8 g, 42.4 mmol; Bull. Chem. Soc. Jpn. 1999, 72, 115–120) was added over 10 min. The reaction mixture was stirred over night at room temperature. Water (5 ml) was added followed by decalite. The mixture was evaporated and the solid residue was extracted with dichloromethane (3×200 ml). The combined organic phases were evaporated to give crude product in 17.9 g (80%) yield. Purification by column chromatography (eluent: dichloromethane) gave ethyl 3,3-bis-(4-iodophenyl)-acrylate as an oil in 9.6 g (43%) yield.

$^1$H NMR (CDCl$_3$, 300 MHz); δ 1.15 (3H, t), 4.07 (2H, q), 6.35 (1H, s), 6.90–7.02 (4H, m), 7.63–7.75 (4H, m).

Step B:

To a solution of ethyl 3,3-bis-(4-iodophenyl)-acrylate (706 mg, 1.4 mmol) in THF (1.5 ml) was added over 45 min a solution of DIBAL-H (1.5 M in toluene, 6.3 ml, 9.5 mmol) at −20° C. The reaction mixture was stirred for a further 1 h. A solution of ammonium chloride was and to the mixture was added ethyl acetate (40 ml) and decalite. The mixture was filtered and the filter washed with ethyl acetate (100 ml). The combined filtrates were evaporated and the residue was purified by column chromatography (eluent: dichloromethane:THF (8:3)) to give 3,3-bis-(4-iodophenyl)-pro-2-en-1-ol in 541 mg (84%) yield.

$^1$H NMR (CDCl$_3$, 300 MHz); δ 1.60 (1H, br s), 4.20 (2H, d), 6.23 (1H, t), 6.84–7.00 (4H, m), 7.57–7.75 (4H, m).

Step C:

In a vial for micro wave oven was added under nitrogen 3,3-bis-(4-iodophenyl)-pro-2-en-1-ol (326 mg, 0.7 mmol), pyridine-3-boronic acid (199 mg, 1.6 mmol), sodium carbonate (449 mg, 4.2 mmol), Pd(PPh$_3$)$_2$Cl (32 mg, 0.04 mmol), dimethyl ether (4.2 ml), water (1.8 ml) and ethanol (99%, 1.2 ml). The reaction was run for 7 min at 140° C. in the micro wave oven. The reaction was filtered and the filtrate evaporated. The residue was purified by column chromatography (eluent: dichloromethane:THF (1:1)) to give 3,3-bis-(4-pyridin-3-yl-phenyl)-prop-2-en-1-ol in 205 mg (72%) yield.

$^1$H NMR (MeOD, 400 MHz) δ 4.18 (2H, d), 6.36 (1H, t), 7.32 (2H, d), 7.38 (2H, d), 7.44–7.54 (2H, m), 7.59 (2H, d), 7.69 (2H, d), 8.02–8.14 (2H, m), 8.51 (2H, m), 8.75–8.85 (2H, m).

Triphenylphosphine (138 mg, 0.68 mmol) and ADDP (173 mg, 0.68 mmol) were added to a solution of 3,3-bis-(4-pyridin-3-yl-phenyl)-prop-2-en-1-ol (100 mg, 0.27 mmol) in THF (5 ml) at 0° C. The reaction mixture was stirred for 5 min under nitrogen atmosphere. (4-Mercapto-2-trifluoromethyl-phenoxy)-acetic acid ethyl ester (prepared analogous to procedure in BioOrg. Med. Chem. Lett. 2003, 13, 1517) (92 mg, 0.32 mmol) was slowly added to the reaction mixture and the reaction was stirred for further 2 h at 0° C. The reaction mixture was evaporated and the residue was triturated with ether (2×15 ml). The filtered ether phases were evaporated and purified by column chromatography (eluent: ethyl acetate) to give {4-[3,3-bis-(4-pyridin-3-yl-phenyl)-allylsulfanyl]-2-trifluoromethyl-phenoxy}-acetic acid ethyl ester in 100 mg (60%) yield.

$^1$H NMR (CDCl$_3$, 400 MHz) δ 1.24 (3H, t), 3.61 (2H, d), 4.22 (2H, q), 4.70 (2H, s), 6.23 (1H, t), 6.77 (1H, d), 7.05 (2H, d), 7.25–7.62 (10H, m), 7.74–7.95 (2H, m), 8.60 (2H, m), 8.82–8.94 (2H, m).

A solution of {4-[3,3-bis-(4-pyridin-3-yl-phenyl)-allylsulfanyl]-2-trifluoromethyl-phenoxy}-acetic acid ethyl ester (70 mg, 0.1 mmol) in ethanol (10 ml) and 1N NaOH (0.5 ml) was stirred at 75° C. for 1 h. The reaction mixture was evaporated and the residue was treated with 1N HCl (0.7 ml) and extracted with methylene chloride (2×25 ml). The organic phases were dried and evaporated to give the title compound in 23 mg (34%) yield.

$^1$H NMR (CDCl$_3$, 400 MHz) δ 3.45 (2H, d), 4.89 (2H, s), 6.27 (1H, t), 6.80 (3H, m), 7.27 (2H, d), 7.38–7.75 (8H, m), 8.06 (1H, m), 8.33 (1H, m), 8.58 (2H, m), 8.85 (1H, s), 9.27 (1H, s).

Pharmacological Methods

In Vitro PPARalpha, PPARgamma and PPARdelta Activation Activity

The PPAR transient transactivation assays are based on transient transfection into human HEK293 cells of two plasmids encoding a chimeric test protein and a reporter protein respectively. The chimeric test protein is a fusion of the DNA binding domain (DBD) from the yeast GAL4 transcription factor to the ligand binding domain (LBD) of the human PPAR proteins. The PPAR-LBD moiety harbored in addition to the ligand binding pocket also the native activation domain (activating function 2=AF2) allowing the fusion protein to function as a PPAR ligand dependent transcription factor. The GAL4 DBD will direct the chimeric protein to bind only to Gal4 enhancers (of which none existed in HEK293 cells). The reporter plasmid contained a Gal4 enhancer driving the expression of the firefly luciferase protein. After transfection, HEK293 cells expressed the GAL4-DBD-PPAR-LBD fusion protein. The fusion protein will in turn bind to the Gal4 enhancer controlling the luciferase expression, and do nothing in the absence of ligand. Upon addition to the cells of a PPAR ligand luciferase protein will be produced in amounts corresponding to the activation of the PPAR protein. The amount of luciferase protein is measured by light emission after addition of the appropriate substrate.

Cell Culture and Transfection

HEK293 cells were grown in DMEM +10% FCS. Cells were seeded in 96-well plates the day before transfection to give a confluency of 50–80% at transfection. A total of 0.8 μg DNA containing 0.64 μg pM1α/γLBD, 0.1 μg pCMVβGal, 0.08 μg pGL2(Gal4)$_5$ and 0.02 μg pADVANTAGE was transfected per well using FuGene transfection reagent according to the manufacturers instructions (Roche). Cells were allowed to express protein for 48 h followed by addition of compound.

Plasmids: Human PPAR α, γ and δ was obtained by PCR amplification using cDNA synthesized by reverse transcription of mRNA from human liver, adipose tissue and placenta respectively. Amplified cDNAs were cloned into pCR2.1 and sequenced. The ligand binding domain (LBD) of each PPAR isoform was generated by PCR (PPARα: aa 167—C-terminus; PPARγ: aa 165—C-terminus; PPARδ: aa 128—C-terminus) and fused to the DNA binding domain (DBD) of the yeast transcription factor GAL4 by subcloning fragments in frame into the vector pM1 (Sadowski et al. (1992), Gene 118, 137) generating the plasmids pM1αLBD, pM1γLBD and pM1δ. Ensuing fusions were verified by sequencing. The reporter was constructed by inserting an oligonucleotide encoding five repeats of the GAL4 recognition sequence (5×CGGAGTACTGTCCTCCG(AG)) (Webster et al. (1988), Nucleic Acids Res. 16, 8192) into the vector pGL2 promotor (Promega) generating the plasmid pGL2(GAL4)$_5$. pCMVβGal was purchased from Clontech and pADVANTAGE was purchased from Promega.

In Vitro Transactivation Assay

Compounds: All compounds were dissolved in DMSO and diluted 1:1000 upon addition to the cells. Compounds were tested in quadruple in concentrations ranging from 0.001 to 300 μM. Cells were treated with compound for 24 h followed by luciferase assay. Each compound was tested in at least two separate experiments.

Luciferase assay: Medium including test compound was aspirated and 100 μl PBS incl. 1 mM Mg++ and Ca++ was added to each well. The luciferase assay was performed using the LucLite kit according to the manufacturers instructions (Packard Instruments). Light emission was quantified by counting on a Packard LumiCounter. To measure β-galactosidase activity 25 μl supernatant from each transfection lysate was transferred to a new microplate. β-galactosidase assays were performed in the microwell plates using a kit from Promega and read in a Labsystems Ascent Multiscan reader. The β-galactosidase data were used to normalize (transfection efficiency, cell growth etc.) the luciferase data.

Statistical Methods

The activity of a compound is calculated as fold induction compared to an untreated sample. For each compound the efficacy (maximal activity) is given as a relative activity compared to Wy14,643 for PPARα, Rosiglitazone for PPARγ and Carbacyclin for PPARδ. The EC50 is the concentration giving 50% of maximal observed activity. EC50 values were calculated via non-linear regression using GraphPad PRISM 3.02 (GraphPad Software, San Diego, Calif.). The results were expressed as means ±SD.

The invention claimed is:
1. A compound of formula (I):

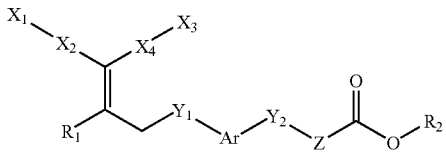

wherein X₁ is aryl or heteroaryl each of which is optionally substituted with one or more substituents selected from
halogen, hydroxy, cyano, amino or carboxy; or
$C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-dialkylaminocarbonyl, $C_{1-6}$-alkylamino, $C_{1-6}$-dialkylamino or $C_{3-6}$-cycloalkylamino each of which is optionally substituted with one or more halogens; and
X₂ is arylene or heteroarylene each of which is optionally substituted with one or more substituents selected from halogen, hydroxy, cyano, amino or carboxy; or
$C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, $C_{3-6}$-cycloalkylthio, $C_{1-6}$-alkylamino, $C_{1-6}$-dialkylamino or $C_{3-6}$-cycloalkylamino each of which is optionally substituted with one or more halogens; and
X₃ is aryl or heteroaryl each of which is optionally substituted with one or more substituents selected from halogen, hydroxy, cyano, amino or carboxy; or
$C_{1-6}$-alkyl, $C_{3-6}$-cycloalkyl, $C_{2-6}$-alkenyl, $C_{2-6}$-alkynyl, aryl, aralkyl, heteroaryl, heteroaralkyl, $C_{1-6}$-alkoxy, $C_{3-6}$-cycloalkoxy, aryloxy, aralkoxy, heteroaralkoxy, $C_{1-6}$-alkylthio, arylthio, $C_{3-6}$-cycloalkylthio, $C_{1-6}$-alkylcarbonyl, arylcarbonyl, $C_{1-6}$-alkylsulfonyl, arylsulfonyl, $C_{1-6}$-alkylamido, arylamido, $C_{1-6}$-alkylaminocarbonyl, $C_{1-6}$-dialkylaminocarbonyl, $C_{1-6}$-alkylamino, $C_{1-6}$-dialkylamino or $C_{3-6}$-cycloalkylamino each of which is optionally substituted with one or more halogens; and
X₄ is arylene or heteroarylene each of which is optionally substituted with one or more substituents selected from halogen, hydroxy, cyano, amino or carboxy; or
$C_{1-6}$-alkyl, $C_{3-6}$-cycloalkyl, $C_{2-6}$-alkenyl, $C_{2-6}$-alkynyl, $C_{1-6}$-alkoxy, $C_{3-6}$-cycloalkoxy, $C_{1-6}$-alkylthio, $C_{3-6}$-cycloalkylthio, $C_{1-6}$-alkylamino, $C_{1-6}$-dialkylamino or $C_{3-6}$-cycloalkylamino each of which is optionally substituted with one or more halogens; and
Ar is arylene which is optionally substituted with one or more substituents selected from
halogen, hydroxy or cyano; or
$C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; and
Y₁ is O or S; and
Y₂ is O or S; and
Z is —(CH₂)$_n$— wherein n is 1, 2 or 3; and
R₁ is hydrogen, halogen or a substituent selected from
$C_{1-6}$-alkyl, $C_{3-6}$-cycloalkyl, $C_{2-6}$-alkenyl, $C_{2-6}$-alkynyl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens; and
R₂ is hydrogen, $C_{1-6}$-alkyl, $C_{3-6}$-cycloalkyl, $C_{2-6}$-alkenyl, $C_{2-6}$-alkynyl, $C_{4-6}$-alkenynyl or aryl; or
a pharmaceutically acceptable salt thereof, or a pharmaceutically acceptable solvate thereof, or any tautomeric forms, stereoisomers, mixture of stereoisomers, racemic mixture, or polymorphs thereof.

2. A compound according to claim 1, wherein X₁ is aryl optionally substituted with one or more substituents selected from
halogen, hydroxy; or
$C_{1-6}$-alkyl, aryl, heteroaryl, $C_{1-6}$-alkoxy, $C_{1-6}$-alkylthio, $C_{1-6}$-alkylcarbonyl, $C_{1-6}$-alkylsulfonyl, arylamido, $C_{1-6}$-alkylaminocarbonyl or $C_{1-6}$-dialkylaminocarbonyl each of which is optionally substituted with one or more halogens.

3. A compound according to claim 2, wherein X₁ is aryl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

4. A compound according to claim 2, wherein X₁ is phenyl optionally substituted with one or more substituents selected from
halogen, hydroxy; or
$C_{1-6}$-alkyl, aryl, heteroaryl, $C_{1-6}$-alkoxy, $C_{1-6}$-alkylthio, $C_{1-6}$-alkylcarbonyl, $C_{1-6}$-alkylsulfonyl, arylamido, $C_{1-6}$-alkylaminocarbonyl or $C_{1-6}$-dialkylaminocarbonyl each of which is optionally substituted with one or more halogens.

5. A compound according to claim 4, wherein X₁ is phenyl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

6. A compound according to claim 1, wherein X₁ is heteroaryl optionally substituted with one or more substituents selected from
halogen, hydroxy; or
$C_{1-6}$-alkyl, aryl, heteroaryl, $C_{1-6}$-alkoxy, $C_{1-6}$-alkylthio, $C_{1-6}$-alkylcarbonyl, $C_{1-6}$-alkylsulfonyl, arylamido, $C_{1-6}$-alkylaminocarbonyl or $C_{1-6}$-dialkylaminocarbonyl each of which is optionally substituted with one or more halogens.

7. A compound according to claim 6, wherein X₁ is heteroaryl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

8. A compound according to claim 7, wherein X₁ is furyl, thienyl, pyrrolyl, thiazolyl, imidazolyl, oxazolyl, isoxazolyl, isothiazolyl, pyridyl or pyrimidinyl, each of which is optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

9. A compound according to claim 8, wherein X₁ is pyridyl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

10. A compound according to claim 1, wherein $X_2$ is arylene optionally substituted with one or more substituents selected from
   halogen or
   $C_{1-6}$-alkyl optionally substituted with one or more halogens.

11. A compound according to claim 10, wherein $X_2$ is phenylene optionally substituted with one or more substituents selected from
   halogen or
   $C_{1-6}$-alkyl optionally substituted with one or more halogens.

12. A compound according to claim 11, wherein $X_2$ is phenylene.

13. A compound according to claim 1, wherein $X_2$ is heteroarylene optionally substituted with one or more substituents selected from
   halogen or
   $C_{1-6}$-alkyl optionally substituted with one or more halogens.

14. A compound according to claim 13 wherein $X_2$ is furylene, thienylene, pyrrolylene, thiazolylene, imidazolylene, oxazolylene, isoxazolylene, isothiazolylene, pyridylene or pyrimidinylene, each of which is optionally substituted with one or more substituents selected from
   halogen or
   $C_{1-6}$-alkyl optionally substituted with one or more halogens.

15. A compound according to claim 1, wherein $X_3$ is aryl optionally substituted with one or more substituents selected from
   halogen, hydroxy; or
   $C_{1-6}$-alkyl, aryl, heteroaryl, $C_{1-6}$-alkoxy, $C_{1-6}$-alkylthio, $C_{1-6}$-alkylcarbonyl, $C_{1-6}$-alkylsulfonyl, arylamido, $C_{1-6}$-alkylaminocarbonyl or $C_{1-6}$-dialkylaminocarbonyl each of which is optionally substituted with one or more halogens.

16. A compound according to claim 15, wherein $X_3$ is aryl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

17. A compound according to claim 15, wherein $X_3$ is phenyl optionally substituted with one or more substituents selected from
   halogen, hydroxy; or
   $C_{1-6}$-alkyl, aryl, heteroaryl, $C_{1-6}$-alkoxy, $C_{1-6}$-alkylthio, $C_{1-6}$-alkylcarbonyl, $C_{1-6}$-alkylsulfonyl, arylamido, $C_{1-6}$-alkylaminocarbonyl or $C_{1-6}$-dialkylaminocarbonyl each of which is optionally substituted with one or more halogens.

18. A compound according to claim 17, wherein $X_3$ is phenyl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

19. A compound according to claim 1, wherein $X_3$ is heteroaryl optionally substituted with one or more substituents selected from
   halogen, hydroxy; or
   $C_{1-6}$-alkyl, aryl, heteroaryl, $C_{1-6}$-alkoxy, $C_{1-6}$-alkylthio, $C_{1-6}$-alkylcarbonyl, $C_{1-6}$-alkylsulfonyl, arylamido, $C_{1-6}$-alkylaminocarbonyl or $C_{1-6}$-dialkylaminocarbonyl each of which is optionally substituted with one or more halogens.

20. A compound according to claim 19, wherein $X_3$ is heteroaryl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

21. A compound according to claim 20, wherein $X_3$ is furyl, thienyl, pyrrolyl, thiazolyl, imidazolyl, oxazolyl, isoxazolyl, isothiazolyl, pyridyl or pyrimidinyl, each of which is optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

22. A compound according to claim 21 wherein $X_3$ is pyridyl optionally substituted with one or more substituents selected from $C_{1-6}$-alkyl, phenyl, $C_{1-6}$-alkylsulfonyl, $C_{1-6}$-alkylaminocarbonyl or $C_{1-6}$-dialkylaminocarbonyl each of which is optionally substituted with one or more halogens.

23. A compound according to claim 1, wherein $X_4$ is arylene optionally substituted with one or more substituents selected from
   halogen or
   $C_{1-6}$-alkyl optionally substituted with one or more halogens.

24. A compound according to claim 23, wherein $X_4$ is phenylene optionally substituted with one or more substituents selected from
   halogen or
   $C_{1-6}$-alkyl optionally substituted with one or more halogens.

25. A compound according to claim 24, wherein $X_4$ is phenylene.

26. A compound according to claim 1, wherein $X_4$ is heteroarylene optionally substituted with one or more substituents selected from
   halogen or
   $C_{1-6}$-alkyl optionally substituted with one or more halogens.

27. A compound according to claim 26 wherein $X_4$ is furylene, thienylene, pyrrolylene, thiazolylene, imidazolylene, oxazolylene, isoxazolylene, isothiazolylene, pyridylene or pyrimidinylene, each of which is optionally substituted with one or more substituents selected from
   halogen or
   $C_{1-6}$-alkyl optionally substituted with one or more halogens.

28. A compound according to claim 1, wherein Ar is phenylene which is optionally substituted with one or more substituents selected from
   halogen, hydroxy or cyano; or
   $C_{1-6}$-alkyl, $C_{3-6}$-cycloalkyl, $C_{2-6}$-alkenyl, $C_{2-6}$-alkynyl, aryl, heteroaryl, aralkyl, heteroaralkyl, $C_{1-6}$-alkoxy, $C_{3-6}$-cycloalkoxy, aryloxy, aralkoxy, heteroaralkoxy, $C_{1-6}$-alkylthio, arylthio or $C_{3-6}$-cycloalkylthio each of which is optionally substituted with one or more halogens.

29. A compound according to claim 28, wherein Ar is phenylene which is optionally substituted with one or more substituents selected from
   halogen; or
   $C_{1-6}$-alkyl, $C_{1-6}$-alkoxy, aryloxy, aralkoxy or phenyl, each of which is optionally substituted with one or more halogens.

30. A compound according to claim 28, wherein Ar is phenylene which is optionally substituted with methyl or trifluoromethyl.

31. A compound according to claim 30, wherein Ar is phenylene.

32. A compound according to claim 1, wherein $Y_1$ is S.

33. A compound according to claim 1, wherein $Y_1$ is O.

34. A compound according to claim 1, wherein $Y_2$ is O.

35. A compound according to claim 1, wherein $Y_2$ is S.

36. A compound according to claim 1, wherein n is 1.

37. A compound according to claim 1, wherein $R_1$ is hydrogen or a substituent selected from $C_{1-6}$-alkyl, aralkyl, $C_{1-6}$-alkoxy, aryloxy, aralkoxy each of which is optionally substituted with one or more halogens.

38. A compound according to claim 37, wherein $R_1$ is hydrogen or a substituent selected from $C_{1-6}$-alkyl, $C_{1-6}$-alkoxy each of which is optionally substituted with one or more halogens.

39. A compound according to claim 38, wherein $R_1$ is hydrogen.

40. A compound according to claim 1, wherein $R_2$ is hydrogen.

41. A compound according to claim 1, which is selected from the following:

[4-(3,3-Bis-biphenyl-4-yl-allylsulfanyl)-2-methyl-phenoxy]-acetic acid, {4-[3,3-Bis-(4'-methanesulfonyl-biphenyl-4-yl)-allylsulfanyl]-2-methyl-phenoxy}-acetic acid, {4-[3,3-Bis-(3'-trifluoromethyl-biphenyl-4-yl)-allylsulfanyl]-2-methyl-phenoxy}-acetic acid,

[4-(3,3-Bis-[1,1';4',1"]terphenyl-4-yl-allylsulfanyl)-2-methyl-phenoxy]-acetic acid, {4-[3,3-Bis-(3'-dimethylcarbamoyl-biphenyl-4-yl)-allylsulfanyl]-2-methyl-phenoxy}-acetic acid, {4-[3,3-Bis-(4-pyridin-3-yl-phenyl)-allylsulfanyl]-2-methyl-phenoxy}-acetic acid, and {4-[3,3-Bis-(4-pyridin-3-yl-phenyl)-allylsulfanyl]-2-trifluoromethyl-phenoxy}-acetic acid, or a salt thereof with a pharmaceutically acceptable acid or base, optical isomer or mixture of optical isomers, racemic mixture, or tautomeric forms thereof.

42. A compound according to claim 1, which is selected from the following:

[4-(3,3-Bis-biphenyl-4-yl-allylsulfanyl)-2-methyl-phenoxy]-acetic acid,

[4-(3,3-Bis-biphenyl-4-yl-allyloxy)-2-methyl-phenoxy]-acetic acid, (4-{3,3-Bis-[4-(5-methyl-furan-2-yl)-phenyl]-allyloxy}-2-methyl-phenoxy)-acetic acid, (4-{3,3-Bis-[4-(furan-2-yl)-phenyl]-allyloxy}-2-methyl-phenoxy)-acetic acid, (4-{3,3-Bis-[4-(5-methyl-furan-2-yl)-phenyl]-allylsulfanyl}-2-methyl-phenoxy)-acetic acid, (4-{3,3-Bis-[4-(furan-2-yl)-phenyl]-allylsulfanyl}-2-methyl-phenoxy)-acetic acid, (4-{3,3-Bis-[4-(5-chloro-thiophen-2-yl)-phenyl]-allylsulfanyl}-2-methyl-phenoxy)-acetic acid, (4-{3,3-Bis-[4-(5-chloro-thiophen-2-yl)-phenyl]-allyloxy}-2-methyl-phenoxy)-acetic acid, {4-[3,3-Bis-(4-thiophen-2-yl-phenyl)-allyloxy]-2-methyl-phenoxy}-acetic acid, {4-[3,3-Bis-(4-thiophen-2-yl-phenyl)-allylsulfanyl]-2-methyl-phenoxy}-acetic acid, (4-{3,3-Bis-[4-(5-acetyl-thiophen-2-yl)-phenyl]-allylsulfanyl}-2-methyl-phenoxy)-acetic acid, (4-{3,3-Bis-[4-(5-acetyl-thiophen-2-yl)-phenyl]-allyloxy}-2-methyl-phenoxy)-acetic acid, (4-{3,3-Bis-[4-(5-acetyl-thiophen-2-yl)-phenyl]-2-ethyl-allyloxy}-2-methyl-phenoxy)-acetic acid, (4-{3,3-Bis-[4-(5-acetyl-thiophen-2-yl)-phenyl]-2-ethyl-allylsulfanyl}-2-methyl-phenoxy)-acetic acid, {4-[3,3-Bis-(3'-dimethylcarbamoyl-biphenyl-4-yl)-allylsulfanyl]-2-methyl-phenoxy}-acetic acid, {4-[3,3-Bis-(3'-dimethylcarbamoyl-biphenyl-4-yl)-allyloxy]-2-methyl-phenoxy}-acetic acid, {4-[3,3-Bis-(3'-methylsulfanyl-biphenyl-4-yl)-allylsulfanyl]-2-methyl-phenoxy}-acetic acid, {4-[3,3-Bis-(3'-methylsulfanyl-biphenyl-4-yl)-allyloxy]-2-methyl-phenoxy}-acetic acid, {4-[3,3-Bis-(3'-amino-biphenyl-4-yl)-allyloxy]-2-methyl-phenoxy}-acetic acid, {4-[3,3-Bis-(3'-amino-biphenyl-4-yl)-allylsulfanyl]-2-methyl-phenoxy}-acetic acid, {4-[3,3-Bis-(4'-amino-biphenyl-4yl)-allylsulfanyl]-2-methyl-phenoxy}-acetic acid, {4-[3,3-Bis-(4'-amino-biphenyl-4-yl)-allyloxy]-2-methyl-phenoxy}-acetic acid, {4-[3,3-Bis-(4-pyridin-2-yl-phenyl)-allyloxy]-2-methyl-phenoxy}-acetic acid, {4-[3,3-Bis-(4-pyridin-2-yl-phenyl)-allylsulfanyl]-2-methyl-phenoxy}-acetic acid, {4-[3,3-Bis-(4'-methanesulfonyl-biphenyl-4-yl)-allylsulfanyl]-2-methyl-phenoxy}-acetic acid, {4-[3,3-Bis-(4'-methanesulfonyl-biphenyl-4-yd)-allyloxy]-2-methyl-phenoxy}-acetic acid, {4-[3,3-Bis-(4'-methoxy-biphenyl-4-yl)-allyloxy]-2-methyl-phenoxy}-acetic acid, {4-[3,3-Bis-(4'-methoxy-biphenyl-4-yl)-allylsulfanyl]-2-methyl-phenoxy}-acetic acid, {4-[3,3-Bis-(4'-trifluoromethoxy-biphenyl-4-yl)-allylsulfanyl]-2-methyl-phenoxy}-acetic acid, {4-[3,3-Bis-(4'-trifluoromethoxy-biphenyl-4-yl)-allyloxy]-2-methyl-phenoxy}-acetic acid, {4-[3,3-Bis-(4'-methyl-biphenyl-4-yl)-allyloxy]-2-methyl-phenoxy}-acetic acid, {4-[3,3-Bis-(4'-methyl-biphenyl-4-yl)-allylsulfanyl]-2-methyl-phenoxy}-acetic acid, {4-[3,3-Bis-(4'-trifluoromethyl-biphenyl-4-yl)-allylsulfanyl]-2-methyl-phenoxy}-acetic acid, {4-[3,3-Bis-(4'-trifluoromethyl-biphenyl-4-yl)-allyloxy]-2-methyl-phenoxy}-acetic acid, {4-[3,3-Bis-(4'-chloro-biphenyl-4-yl)-allyloxy]-2-methyl-phenoxy}-acetic acid, {4-[3,3-Bis-(4'-chloro-biphenyl-4-yl)-allylsulfanyl]-2-methyl-phenoxy}-acetic acid, {4-[3,3-Bis-(4'-chloro-biphenyl-4-yl)-allyloxy]-2-methyl-phenoxy}-acetic acid, {4-[3,3-Bis-(4'-tert-butyl-biphenyl-4-yl)-allyloxy]-2-methyl-phenoxy}-acetic acid,

[4-(3,3-Bis-[1,1';4',1"]terphenyl-4-yl-allylsulfanyl)-2-methyl-phenoxy]-acetic acid,

[4-(3,3-Bis-[1,1';4',1"]terphenyl-4-yl-allylsulfanyl)-2-methyl-phenoxy]-acetic acid, {4-[3,3-Bis-(4'-acetyl-biphenyl-4-yl)-allylsulfanyl]-2-methyl-phenoxy}-acetic acid, {4-[3,3-Bis-(4'-acetyl-biphenyl-4-yl)-allyloxy]-2-methyl-phenoxy}-acetic acid, {4-[3,3-Bis-(4'-phenoxy-biphenyl-4-yl)-allyloxy]-2-methyl-phenoxy}-acetic acid, {4-[3,3-Bis-(4'-phenoxy-biphenyl-4-yl)-allylsulfanyl]-2-methyl-phenoxy}-acetic acid, {4-[3,3-Bis-(4'-isopropyl-biphenyl-4-yl)-allylsulfanyl]-2-methyl-phenoxy}-acetic acid, {4-[3,3-Bis-(4'-isopropyl-biphenyl-4-yl)-allyloxy]-2-methyl-phenoxy}-acetic acid, {4-[3,3-Bis-(3',4'-difluoro-biphenyl-4-yl)-allyloxy]-2-methyl-phenoxy}-acetic acid, {4-[3,3-Bis-(3',4'-difluoro-biphenyl-4-yl)-allylsulfanyl]-2-methyl-phenoxy}-acetic acid,
{4-[3,3-Bis-(3',5'-dichloro-biphenyl-4-yl)-allylsulfanyl]-2-methyl-phenoxy}-acetic acid,
{4-[3,3-Bis-(3',5'-dichloro-biphenyl-4-yl)-allyloxy]-2-methyl-phenoxy}-acetic acid,
{4-[3,3-Bis-(3'-chloro-4'-fluoro-biphenyl-4-yl)-allyloxy]-2-methyl-phenoxy}-acetic acid,
{4-[3,3-Bis-(3'-chloro-4'-fluoro-biphenyl-4-yl)-allylsulfanyl]-2-methyl-phenoxy}-acetic acid,
(4-{3,3-Bis-[4-(4-methyl-furan-2-yl)-phenyl]-allyloxy}-2-methyl-phenoxy)-acetic acid,
(4-{3,3-Bis-[4-(4-methyl-furan-2-yl)-phenyl]-allylsulfanyl}-2-methyl-phenoxy)-acetic acid,
(4-{3,3-Bis-[4-(4-chloro-thiophen-2-yl)-phenyl]-allylsulfanyl}-2-methyl-phenoxy)-acetic acid,
(4-{3,3-Bis-[4-(4-chloro-thiophen-2-yl)-phenyl]-allyloxy}-2-methyl-phenoxy)-acetic acid,
(4-{3,3-Bis-[4-(4-acetyl-thiophen-2-yl)-phenyl]-allylsulfanyl}-2-methyl-phenoxy)-acetic acid,
(4-{3,3-Bis-[4-(4-acetyl-thiophen-2-yl)-phenyl]-allyloxy}-2-methyl-phenoxy)-acetic acid,
(4-{3,3-Bis-[4-(4-acetyl-thiophen-2-yl)-phenyl]-2-ethyl-allyloxy}-2-methyl-phenoxy)-acetic acid,
(4-{3,3-Bis-[4-(4-acetyl-thiophen-2-yl)-phenyl]-2-ethyl-allylsulfanyl}-2-methyl-phenoxy)-acetic acid,
{4-[3,3-Bis-(4-pyridin-3-yl-phenyl)-allyloxy]-2-methyl-phenoxy}-acetic acid,
{4-[3,3-Bis-(4-pyridin-3-yl-phenyl)-allylsulfanyl]-2-methyl-phenoxy}-acetic acid, {4-[3,3-Bis-(3'-dimethylcarbamoyl-biphenyl-4-yl)-allylsulfanyl]-phenoxy}-acetic acid,
{4-[3,3-Bis-(3'-dimethylcarbamoyl-biphenyl-4-yl)-allyloxy]-2-methyl-phenoxy}-acetic acid,
{4-[3,3-Bis-(3'-methoxy-biphenyl-4-yl)-allyloxy]-2-methyl-phenoxy}-acetic acid,
{4-[3,3-Bis-(3'-methoxy-biphenyl-4-yl)-allylsulfanyl]-2-methyl-phenoxy}-acetic acid,
{4-[3,3-Bis-(3'-trifluoromethoxy-biphenyl-4-yl)-allylsulfanyl]-2-methyl-phenoxy}-acetic acid,
{4-[3,3-Bis-(3'-trifluoromethoxy-biphenyl-4-yl)-allyloxy]-2-methyl-phenoxy}-acetic acid,
{4-[3,3-Bis-(3'-methyl-biphenyl-4-yl)-allyloxy]-2-methyl-phenoxy}-acetic acid,
{4-[3,3-Bis-(3'-methyl-biphenyl-4-yd)-allylsulfanyl]-2-methyl-phenoxy}-acetic acid,
{4-[3,3-Bis-(3'-trifluoromethyl-biphenyl-4-yl)-allylsulfanyl]-2-methyl-phenoxy}-acetic acid,
{4-[3,3-Bis-(3'-trifluoromethyl-biphenyl-4-yd)-allyloxy]-2-methyl-phenoxy}-acetic acid,
{4-[3,3-Bis-(3'-chloro-biphenyl-4-yl)-allyloxy]-2-methyl-phenoxy}-acetic acid,
{4-[3,3-Bis-(3'-chloro-biphenyl-4-yl)-allylsulfanyl]-2-methyl-phenoxy}-acetic acid,
{4-[3,3-Bis-(3'-chloro-biphenyl-4-yl)-allyloxy]-2-methyl-phenoxy}-acetic acid,
{4-[3,3-Bis-(3'-tert-butyl-biphenyl-4-yl)-allyloxy]-2-methyl-phenoxy}-acetic acid,
{4-[3,3-Bis-(3'-acetyl-biphenyl-4-yl)-allylsulfanyl]-2-methyl-phenoxy}-acetic acid,
{4-[3,3-Bis-(3'-acetyl-biphenyl-4-yd)-allyloxy]-2-methyl-phenoxy}-acetic acid,
{4-[3,3-Bis-(3'-phenoxy-biphenyl-4-yl)-allyloxy]-2-methyl-phenoxy}-acetic acid,
{4-[3,3-Bis-(3'-phenoxy-biphenyl-4-yl)-allylsulfanyl]-2-methyl-phenoxy}-acetic acid,
{4-[3,3-Bis-(3'-isopropyl-biphenyl-4-yl)-allylsulfanyl]-2-methyl-phenoxy}-acetic acid,
{4-[3,3-Bis-(3'-isopropyl-biphenyl-4-yl)-allyloxy]-2-methyl-phenoxy}-acetic acid,
{4-[3,3-Bis-(2',4'-difluoro-biphenyl-4-yd)-allyloxy]-2-methyl-phenoxy}-acetic acid,
{4-[3,3-Bis-(2',4'-difluoro-biphenyl-4-yl)-allylsulfanyl]-2-methyl-phenoxy}-acetic acid,
{4-[3,3-Bis-(2',5'-dichloro-biphenyl-4-yl)-allylsulfanyl]-2-methyl-phenoxy}-acetic acid,
{4-[3,3-Bis-(2',5'-dichloro-biphenyl-4-yl)-allyloxy]-2-methyl-phenoxy}-acetic acid,
{4-[3,3-Bis-(2'-chloro-4'-fluoro-biphenyl-4-yl)-allyloxy]-2-methyl-phenoxy}-acetic acid,
{4-[3,3-Bis-(2'-chloro-4'-fluoro-biphenyl-4-yl)-allylsulfanyl]-2-methyl-phenoxy}-acetic acid,
[4-(3,3-Bis-biphenyl-4-yl-allylsulfanyl)-phenoxy]-acetic acid,
[4-(3,3-Bis-biphenyl-4-yl-allyloxy)-phenoxy]-acetic acid,
(4-{3,3-Bis-[4-(5-methyl-fu ran-2-yl)-phenyl]-allyloxy}-phenoxy)-acetic acid,
(4-{3,3-Bis-[4-(-furan-2-yl)-phenyl]-allyloxy}-phenoxy)-acetic acid,
(4-{3,3-Bis-[4-(5-methyl-furan-2-yl)-phenyl]-allylsulfanyl}-phenoxy)-acetic acid,
(4-{3,3-Bis-[4-(furan-2-yl)-phenyl]-allylsulfanyl}-phenoxy)-acetic acid,
(4-{3,3-Bis-[4-(5-chloro-thiophen-2-yl)-phenyl]-allylsulfanyl}-phenoxy)-acetic acid,
(4-{3,3-Bis-[4-(5-chloro-thiophen-2-yl)-phenyl]-allyloxy}-phenoxy)-acetic acid,
{4-[3,3-Bis-(4-thiophen-2-yl-phenyl)-allyloxy]-phenoxy}-acetic acid,
{4-[3,3-Bis-(4-thiophen-2-yl-phenyl)-allylsulfanyl]-phenoxy}-acetic acid,
(4-{3,3-Bis-[4-(5-acetyl-thiophen-2-yl)-phenyl]-allylsulfanyl}-phenoxy)-acetic acid,
(4-{3,3-Bis-[4-(5-acetyl-thiophen-2-yl)-phenyl]-allyloxy}-phenoxy)-acetic acid,
(4-{3,3-Bis-[4-(5-acetyl-thiophen-2-yl)-phenyl]-2-ethyl-allyloxy}-phenoxy)-acetic acid,
(4-{3,3-Bis-[4-(5-acetyl-thiophen-2-yl)-phenyl]-2-ethyl-allylsulfanyl}-phenoxy)-acetic acid,
{4-[3,3-Bis-(3'-methylsulfanyl-biphenyl-4-yl)-allylsulfanyl]-phenoxy}-acetic acid,
{4-[3,3-Bis-(3'-methylsulfanyl-biphenyl-4-yl)-allyloxy]-phenoxy}-acetic acid,
{4-[3,3-Bis-(3'-amino-biphenyl-4-yl)-allyloxy]-phenoxy}-acetic acid,
{4-[3,3-Bis-(3'-amino-biphenyl-4-yl)-allylsulfanyl]-phenoxy}-acetic acid,
{4-[3,3-Bis-(4'-amino-biphenyl-4-yl)-allylsulfanyl]-phenoxy}-acetic acid,
{4-[3,3-Bis-(4'-amino-biphenyl-4-yl)-allyloxy]-phenoxy}-acetic acid,
{4-[3,3-Bis-(4-pyridin-2-yl-phenyl)-allyloxy]-phenoxy}-acetic acid,
{4-[3,3-Bis-(4-pyridin-2-yl-phenyl)-allylsulfanyl]-phenoxy}-acetic acid,
{4-[3,3-Bis-(4'-methanesulfonyl-biphenyl-4-yl)-allylsulfanyl]-phenoxy}-acetic acid,
{4-[3,3-Bis-(4'-methanesulfonyl-biphenyl-4-yl)-allyloxy]-phenoxy}-acetic acid,
{4-[3,3-Bis-(4'-methoxy-biphenyl-4-yl)-allyloxy]-phenoxy}-acetic acid, {4-[3,3-Bis-(4'-methoxy-biphenyl-4-yl)-allylsulfanyl]-phenoxy}-acetic acid,
{4-[3,3-Bis-(4'-trifluoromethoxy-biphenyl-4-yl)-allylsulfanyl]-phenoxy}-acetic acid,
{4-[3,3-Bis-(4'-trifluoromethoxy-biphenyl-4-yl)-allyloxy]-phenoxy}-acetic acid,
{4-[3,3-Bis-(4'-methyl-biphenyl-4-yl)-allyloxy]-phenoxy}-acetic acid,
{4-[3,3-Bis-(4'-methyl-biphenyl-4-yl)-allylsulfanyl]-phenoxy}-acetic acid,
{4-[3,3-Bis-(4'-trifluoromethyl-biphenyl-4-yl)-allylsulfanyl]-phenoxy}-acetic acid,
{4-[3,3-Bis-(4'-trifluoromethyl-biphenyl-4-yl)-allyloxy]-phenoxy}-acetic acid,
{4-[3,3-Bis-(4'-chloro-biphenyl-4-yl)-allyloxy]-phenoxy}-acetic acid,
{4-[3,3-Bis-(4'-chloro-biphenyl-4-yl)-allylsulfanyl]-phenoxy}-acetic acid,
{4-[3,3-Bis-(4'-chloro-biphenyl-4-yl)-allyloxy]-phenoxy}-acetic acid,
{4-[3,3-Bis-(4'-tert-butyl-biphenyl-4-yl)-allyloxy]-phenoxy}-acetic acid,
[4-(3,3-Bis-[1,1';4',1"]terphenyl-4-yl-allylsulfanyl)-phenoxy]-acetic acid,
[4-(3,3-Bis-[1,1';4',1"]terphenyl-4-yl-allylsulfanyl)-phenoxy]-acetic acid,
{4-[3,3-Bis-(4'-acetyl-biphenyl-4-yl)-allylsulfanyl]-phenoxy}-acetic acid,
{4-[3,3-Bis-(4'-acetyl-biphenyl-4-yl)-allyloxy]-phenoxy}-acetic acid,
{4-[3,3-Bis-(4'-phenoxy-biphenyl-4-yl)-allyloxy]-phenoxy}-acetic acid,
{4-[3,3-Bis-(4'-phenoxy-biphenyl-4-yl)-allylsulfanyl]-phenoxy}-acetic acid,
{4-[3,3-Bis-(4'-isopropyl-biphenyl-4-yl)-allylsulfanyl]-phenoxy}-acetic acid,
{4-[3,3-Bis-(4'-isopropyl-biphenyl-4-yl)-allyloxy]-phenoxy}-acetic acid,
{4-[3,3-Bis-(3',4'-difluoro-biphenyl-4-yl)-allyloxy]-phenoxy}-acetic acid,
{4-[3,3-Bis-(3',4'-difluoro-biphenyl-4-yl)-allylsulfanyl]-phenoxy}-acetic acid,
{4-[3,3-Bis-(3',5'-dichloro-biphenyl-4-yl)-allylsulfanyl]-phenoxy}-acetic acid,
{4-[3,3-Bis-(3',5'-dichloro-biphenyl-4-yl)-allyloxy]-phenoxy}-acetic acid,
{4-[3,3-Bis-(3'-chloro-4'-fluoro-biphenyl-4-yl)-allyloxy]-phenoxy}-acetic acid,
{4-[3,3-Bis-(3'-chloro-4'-fluoro-biphenyl-4-yl)-allylsulfanyl]-phenoxy}-acetic acid,
(4-{3,3-Bis-[4-(4-methyl-furan-2-yl)-phenyl]-allyloxy}-phenoxy)-acetic acid,
(4-{3,3-Bis-[4-(4-methyl-furan-2-yl)-phenyl]-allylsulfanyl}-phenoxy)-acetic acid,
(4-{3,3-Bis-[4-(4-chloro-thiophen-2-yl)-phenyl]-allylsulfanyl}-phenoxy)-acetic acid,
(4-{3,3-Bis-[4-(4-chloro-thiophen-2-yl)-phenyl]-allyloxy}-phenoxy)-acetic acid,
(4-{3,3-Bis-[4-(4-acetyl-thiophen-2-yl)-phenyl]-allylsulfanyl}-phenoxy)-acetic acid,
(4-{3,3-Bis-[4-(4-acetyl-thiophen-2-yl)-phenyl]-allyloxy}-phenoxy)-acetic acid
(4-{3,3-Bis-[4-(4-acetyl-thiophen-2-yl)-phenyl]-2-ethyl-allyloxy}-phenoxy)-acetic acid
(4-{3,3-Bis-[4-(4-acetyl-thiophen-2-yl)-phenyl]-2-ethyl-allylsulfanyl}-phenoxy)-acetic acid {4-[3,3-Bis-(4-pyridin-3-yl-phenyl)-allyloxy]-phenoxy}acetic acid
{4-[3,3-Bis-(4-pyridin-3-yl-phenyl)-allylsulfanyl]-phenoxy}-acetic acid
{4-[3,3-Bis-(3'-methoxy-biphenyl-4-yl)-allyloxy]-phenoxy}-acetic acid
{4-[3,3-Bis-(3'-methoxy-biphenyl-4-yl)-allylsulfanyl]-phenoxy}-acetic acid,
{4-[3,3-Bis-(3'-trifluoromethoxy-biphenyl-4-yl)-allylsulfanyl]-phenoxy}-acetic acid,
{4-[3,3-Bis-(3'-trifluoromethoxy-biphenyl-4-yl)-allyloxy]-phenoxy}-acetic acid,
{4-[3,3-Bis-(3'-methyl-biphenyl-4-yl)-allyloxy]-phenoxy}-acetic acid,
{4-[3,3-Bis-(3'-methyl-biphenyl-4-yl)-allylsulfanyl]-phenoxy}-acetic acid,
{4-[3,3-Bis-(3'-trifluoromethyl-biphenyl-4-yl)-allylsulfanyl]-phenoxy}-acetic acid,
{4-[3,3-Bis-(3'-trifluoromethyl-biphenyl-4-yl)-allyloxy]-phenoxy}-acetic acid,
{4-[3,3-Bis-(3'-chloro-biphenyl-4-yl)-allyloxy]-phenoxy}-acetic acid,
{4-[3,3-Bis-(3'-chloro-biphenyl-4-yl)-allylsulfanyl]-phenoxy}-acetic acid,
{4-[3,3-Bis-(3'-chloro-biphenyl-4-yl)-allyloxy]-phenoxy}-acetic acid,
{4-[3,3-Bis-(3'-tert-butyl-biphenyl-4-yl)-allyloxy]-phenoxy}-acetic acid,
{4-[3,3-Bis-(3'-acetyl-biphenyl-4-yl)-allylsulfanyl]-phenoxy}-acetic acid,
{4-[3,3-Bis-(3'-acetyl-biphenyl-4-yl)-allyloxy]-phenoxy}-acetic acid,
{4-[3,3-Bis-(3'-phenoxy-biphenyl-4-yl)-allyloxy]-phenoxy}-acetic acid,
{4-[3,3-Bis-(3'-phenoxy-biphenyl-4-yl)-allylsulfanyl]-phenoxy}-acetic acid,
{4-[3,3-Bis-(3'-isopropyl-biphenyl-4-yl)-allylsulfanyl]-phenoxy}-acetic acid,
{4-[3,3-Bis-(3'-isopropyl-biphenyl-4-yl)-allyloxy]-phenoxy}-acetic acid,
{4-[3,3-Bis-(2',4'-difluoro-biphenyl-4-yl)-allyloxy]-phenoxy}-acetic acid,
{4-[3,3-Bis-(2',4'-difluoro-biphenyl-4-yl)-allylsulfanyl]-phenoxy}-acetic acid,
{4-[3,3-Bis-(2',5'-dichloro-biphenyl-4-yl)-allylsulfanyl]-phenoxy}-acetic acid,
{4-[3,3-Bis-(2',5'-dichloro-biphenyl-4-yl)-allyloxy]-phenoxy}-acetic acid,
{4-[3,3-Bis-(2'-chloro-4'-fluoro-biphenyl-4-yl)-allyloxy]-phenoxy}-acetic acid,
{4-[3,3-Bis-(2'-chloro-4'-fluoro-biphenyl-4-yl)-allylsulfanyl]-phenoxy}-acetic acid,
[4-(3,3-Bis-biphenyl-4-yl-2-ethyl-allylsulfanyl)-2-methyl-phenoxy]-acetic acid,
[4-(3,3-Bis-biphenyl-4-yl-2-ethyl-allyloxy)-2-methyl-phenoxy]-acetic acid,
(4-{3,3-Bis-[4-(5-methyl-furan-2-yl)-phenyl]-2-ethyl-allyloxy}-2-methyl-phenoxy)-acetic acid,
(4-{3,3-Bis-[4-(furan-2-yl)-phenyl]-2-ethyl-allyloxy}-2-methyl-phenoxy)-acetic acid,
(4-{3,3-Bis-[4-(5-methyl-furan-2-yl)-phenyl]-2-ethyl-allylsulfanyl}-2-methyl-phenoxy)-acetic acid,
(4-{3,3-Bis-[4-(furan-2-yl)-phenyl]-2-ethyl-allylsulfanyl}-2-methyl-phenoxy)-acetic acid,
(4-{3,3-Bis-[4-(5-chloro-thiophen-2-yl)-phenyl]-2-ethyl-allylsulfanyl}-2-methyl-phenoxy)-acetic acid, (4-{3,3-Bis-[4-(5-chloro-thiophen-2-yl)-phenyl]-2-ethyl-allyloxy}-2-methyl-phenoxy)-acetic acid,
{4-[3,3-Bis-(4-thiophen-2-yl-phenyl)-2-ethyl-allyloxy]-2-methyl-phenoxy}-acetic acid,
{4-[3,3-Bis-(4-thiophen-2-yl-phenyl)-2-ethyl-allylsulfanyl]-2-methyl-phenoxy}-acetic acid,
(4-{3,3-Bis-[4-(5-acetyl-thiophen-2-yl)-phenyl]-2-ethyl-allylsulfanyl}-2-methyl-phenoxy)-acetic acid,
(4-{3,3-Bis-[4-(5-acetyl-thiophen-2-yl)-phenyl]-2-ethyl-allyloxy}-2-methyl-phenoxy)-acetic acid,
(4-{3,3-Bis-[4-(5-acetyl-thiophen-2-yl)-phenyl]-2-ethyl-allyloxy}-2-methyl-phenoxy)-acetic acid,
(4-{3,3-Bis-[4-(5-acetyl-thiophen-2-yl)-phenyl]-2-ethyl-allylsulfanyl}-2-methyl-phenoxy)-acetic acid,
{4-[3,3-Bis-(3'-dimethylcarbamoyl-biphenyl-4-yl)-2-ethyl-allylsulfanyl]-2-methyl-phenoxy}-acetic acid,
{4-[3,3-Bis-(3'-dimethylcarbamoyl-biphenyl-4-yl)-2-ethyl-allyloxy]-2-methyl-phenoxy}-acetic acid,
{4-[3,3-Bis-(3'-methylsulfanyl-biphenyl-4-yl)-2-ethyl-allylsulfanyl]-2-methyl-phenoxy}-acetic acid,
{4-[3,3-Bis-(3'-methylsulfanyl-biphenyl-4-yl)-2-ethyl-allyloxy]-2-methyl-phenoxy}-acetic acid,
{4-[3,3-Bis-(3'-amino-biphenyl-4-yl)-2-ethyl-allyloxy]-2-methyl-phenoxy}-acetic acid,
{4-[3,3-Bis-(3'-amino-biphenyl-4-yl)-2-ethyl-allylsulfanyl]-2-methyl-phenoxy}-acetic acid,
{4-[3,3-Bis-(4'-amino-biphenyl-4-yl)-2-ethyl-allylsulfanyl]-2-methyl-phenoxy}-acetic acid,
{4-[3,3-Bis-(4'-amino-biphenyl-4-yl)-2-ethyl-allyloxy]-2-methyl-phenoxy}-acetic acid,
{4-[3,3-Bis-(4-pyridin-2-yl-phenyl)-2-ethyl-allyloxy]-2-methyl-phenoxy}-acetic acid,
{4-[3,3-Bis-(4-pyridin-2-yl-phenyl)-2-ethyl-allylsulfanyl]-2-methyl-phenoxy}-acetic acid,
{4-[3,3-Bis-(4'-methanesulfonyl-biphenyl-4-yl)-2-ethyl-allylsulfanyl]-2-methyl-phenoxy}-acetic acid,
{4-[3,3-Bis-(4'-methanesulfonyl-biphenyl-4-yl)-2-ethyl-allyloxy]-2-methyl-phenoxy}-acetic acid,
{4-[3,3-Bis-(4'-methoxy-biphenyl-4-yl)-2-ethyl-allyloxy]-2-methyl-phenoxy}-acetic acid,
{4-[3,3-Bis-(4'-methoxy-biphenyl-4-yl)-2-ethyl-allylsulfanyl]-2-methyl-phenoxy}-acetic acid,
{4-[3,3-Bis-(4'-trifluoromethoxy-biphenyl-4-yl)-2-ethyl-allylsulfanyl]-2-methyl-phenoxy}-acetic acid,
{4-[3,3-Bis-(4'-trifluoromethoxy-biphenyl-4-yl)-2-ethyl-allyloxy]-2-methyl-phenoxy}-acetic acid,
{4-[3,3-Bis-(4'-methyl-biphenyl-4-yl)-2-ethyl-allyloxy]-2-methyl-phenoxy}-acetic acid,
{4-[3,3-Bis-(4'-methyl-biphenyl-4-yl)-2-ethyl-allylsulfanyl]-2-methyl-phenoxy}-acetic acid,
{4-[3,3-Bis-(4'-trifluoromethyl-biphenyl-4-yl)-2-ethyl-allylsulfanyl]-2-methyl-phenoxy}-acetic acid,
{4-[3,3-Bis-(4'-trifluoromethyl-biphenyl-4-yl)-2-ethyl-allyloxy]-2-methyl-phenoxy}-acetic acid,
{4-[3,3-Bis-(4'-chloro-biphenyl-4-yl)-2-ethyl-allyloxy]-2-methyl-phenoxy}-acetic acid,
{4-[3,3-Bis-(4'-chloro-biphenyl-4-yl)-2-ethyl-allylsulfanyl]-2-methyl-phenoxy}-acetic acid,
{4-[3,3-Bis-(4'-chloro-biphenyl-4-yl)-2-ethyl-allyloxy]-2-methyl-phenoxy}-acetic acid,
{4-[3,3-Bis-(4'-tert-butyl-biphenyl-4-yl)-2-ethyl-allyloxy]-2-methyl-phenoxy}-acetic acid,
[4-(3,3-Bis-[1,1';4',1"]terphenyl-4-yl-2-ethyl-allylsulfanyl)-2-methyl-phenoxy]-acetic acid,
[4-(3,3-Bis-[1,1';4',1"]terphenyl-4-yl-2-ethyl-allylsulfanyl)-2-methyl-phenoxy]-acetic acid,
{4-[3,3-Bis-(4'-acetyl-biphenyl-4-yl)-2-ethyl-allylsulfanyl]-2-methyl-phenoxy}-acetic acid,
{4-[3,3-Bis-(4'-acetyl-biphenyl-4-yl)-2-ethyl-allyloxy]-2-methyl-phenoxy}-acetic acid,
{4-[3,3-Bis-(4'-phenoxy-biphenyl-4-yl)-2-ethyl-allyloxy]-2-methyl-phenoxy}-acetic acid,
{4-[3,3-Bis-(4'-phenoxy-biphenyl-4-yl)-2-ethyl-allylsulfanyl]-2-methyl-phenoxy}-acetic acid,
{4-[3,3-Bis-(4'-isopropyl-biphenyl-4-yl)-2-ethyl-allylsulfanyl]-2-methyl-phenoxy}-acetic acid,
{4-[3,3-Bis-(4'-isopropyl-biphenyl-4-yl)-2-ethyl-allyloxy]-2-methyl-phenoxy}-acetic acid,
{4-[3,3-Bis-(3',4'-difluoro-biphenyl-4-yl)-2-ethyl-allyloxy]-2-methyl-phenoxy}-acetic acid,
{4-[3,3-Bis-(3',4'-difluoro-biphenyl-4-yl)-2-ethyl-allylsulfanyl]-2-methyl-phenoxy}-acetic acid,
{4-[3,3-Bis-(3',5'-dichloro-biphenyl-4-yl)-2-ethyl-allylsulfanyl]-2-methyl-phenoxy}-acetic acid,
{4-[3,3-Bis-(3',5'-dichloro-biphenyl-4-yl)-2-ethyl-allyloxy]-2-methyl-phenoxy}-acetic acid,
{4-[3,3-Bis-(3'-chloro-4'-fluoro-biphenyl-4-yl)-2-ethyl-allyloxy]-2-methyl-phenoxy}-acetic acid,
{4-[3,3-Bis-(3'-chloro-4'-fluoro-biphenyl-4-yl)-2-ethyl-allylsulfanyl]-2-methyl-phenoxy}-acetic acid,
(4-{3,3-Bis-[4-(4-methyl-furan-2-yl)-phenyl]-2-ethyl-allyloxy}-2-methyl-phenoxy)-acetic acid,
(4-{3,3-Bis-[4-(4-methyl-furan-2-yl)-phenyl]-2-ethyl-allylsulfanyl}-2-methyl-phenoxy)-acetic acid,
(4-{3,3-Bis-[4-(4-chloro-thiophen-2-yl)-phenyl]-2-ethyl-allylsulfanyl}-2-methyl-phenoxy)-acetic acid,
(4-{3,3-Bis-[4-(4-chloro-thiophen-2-yl)-phenyl]-2-ethyl-allyloxy}-2-methyl-phenoxy)-acetic acid,
(4-{3,3-Bis-[4-(4-acetyl-thiophen-2-yl)-phenyl]-2-ethyl-allylsulfanyl}-2-methyl-phenoxy)-acetic acid,
(4-{3,3-Bis-[4-(4-acetyl-thiophen-2-yl)-phenyl]-2-ethyl-allyloxy}-2-methyl-phenoxy)-acetic acid,
{4-[3,3-Bis-(4-pyridin-3-yl-phenyl)-2-ethyl-allyloxy]-2-methyl-phenoxy}-acetic acid,
{4-[3,3-Bis-(4-pyridin-3-yl-phenyl)-2-ethyl-allylsulfanyl]-2-methyl-phenoxy}-acetic acid,
{4-[3,3-Bis-(3'-methoxy-biphenyl-4-yl)-2-ethyl-allyloxy]-2-methyl-phenoxy}-acetic acid,
{4-[3,3-Bis-(3'-methoxy-biphenyl-4-yl)-2-ethyl-allylsulfanyl]-2-methyl-phenoxy}-acetic acid,
{4-[3,3-Bis-(3'-trifluoromethoxy-biphenyl-4-yl)-2-ethyl-allylsulfanyl]-2-methyl-phenoxy}-acetic acid,
{4-[3,3-Bis-(3'-trifluoromethoxy-biphenyl-4-yl)-2-ethyl-allyloxy]-2-methyl-phenoxy}-acetic acid,
{4-[3,3-Bis-(3'-methyl-biphenyl-4-yl)-2-ethyl-allyloxy]-2-methyl-phenoxy}-acetic acid,
{4-[3,3-Bis-(3'-methyl-biphenyl-4-yl)-2-ethyl-allylsulfanyl]-2-methyl-phenoxy}-acetic acid,
{4-[3,3-Bis-(3'-trifluoromethyl-biphenyl-4-yl)-2-ethyl-allylsulfanyl]-2-methyl-phenoxy}-acetic acid,
{4-[3,3-Bis-(3'-trifluoromethyl-biphenyl-4-yl)-2-ethyl-allyloxy]-2-methyl-phenoxy}-acetic acid,
{4-[3,3-Bis-(3'-chloro-biphenyl-4-yl)-2-ethyl-allyloxy]-2-methyl-phenoxy}-acetic acid,
{4-[3,3-Bis-(3'-chloro-biphenyl-4-yl)-2-ethyl-allylsulfanyl]-2-methyl-phenoxy}-acetic acid,
{4-[3,3-Bis-(3'-chloro-biphenyl-4-yl)-2-ethyl-allyloxy]-2-methyl-phenoxy}-acetic acid,
{4-[3,3-Bis-(3'-tert-butyl-biphenyl-4-yl)-2-ethyl-allyloxy]-2-methyl-phenoxy}-acetic acid,
{4-[3,3-Bis-(3'-acetyl-biphenyl-4-yl)-2-ethyl-allylsulfanyl]-2-methyl-phenoxy}-acetic acid, {4-[3,3-Bis-(3'-acetyl-biphenyl-4-yl)-2-ethyl-allyloxy]-2-methyl-phenoxy}-acetic acid,
{4-[3,3-Bis-(3'-phenoxy-biphenyl-4-yl)-2-ethyl-allyloxy]-2-methyl-phenoxy}-acetic acid,
{4-[3,3-Bis-(3'-phenoxy-biphenyl-4-yl)-2-ethyl-allylsulfanyl]-2-methyl-phenoxy}-acetic acid,
{4-[3,3-Bis-(3'-isopropyl-biphenyl-4-yl)-2-ethyl-allylsulfanyl]-2-methyl-phenoxy}-acetic acid,
{4-[3,3-Bis-(3'-isopropyl-biphenyl-4-yl)-2-ethyl-allyloxy]-2-methyl-phenoxy}-acetic acid,
{4-[3,3-Bis-(2',4'-difluoro-biphenyl-4-yl)-2-ethyl-allyloxy]-2-methyl-phenoxy}-acetic acid,
{4-[3,3-Bis-(2',4'-difluoro-biphenyl-4-yl)-2-ethyl-allylsulfanyl]-2-methyl-phenoxy}-acetic acid,
{4-[3,3-Bis-(2',5'-dichloro-biphenyl-4-yl)-2-ethyl-allylsulfanyl]-2-methyl-phenoxy}-acetic acid,
{4-[3,3-Bis-(2',5'-dichloro-biphenyl-4-yl)-2-ethyl-allyloxy]-2-methyl-phenoxy}-acetic acid,
{4-[3,3-Bis-(2'-chloro-4'-fluoro-biphenyl-4-yl)-2-ethyl-allyloxy]-2-methyl-phenoxy}-acetic acid,
{4-[3,3-Bis-(2'-chloro-4'-fluoro-biphenyl-4-yl)-2-ethyl-allylsulfanyl]-2-methyl-phenoxy}-acetic acid,
[4-(3,3-Bis-biphenyl-4-yl-2-ethoxy-allylsulfanyl)-2-methyl-phenoxy]-acetic acid,
[4-(3,3-Bis-biphenyl-4-yl-2-ethoxy-allyloxy)-2-methyl-phenoxy]-acetic acid,
(4-{3,3-Bis-[4-(5-methyl-furan-2-yl)-phenyl]-2-ethoxy-allyloxy}-2-methyl-phenoxy)-acetic acid,
(4-{3,3-Bis-[4-(furan-2-yl)-phenyl]-2-ethoxy-allyloxy}-2-methyl-phenoxy)-acetic acid,
(4-{3,3-Bis-[4-(5-methyl-furan-2-yl)-phenyl]-2-ethoxy-allylsulfanyl}-2-methyl-phenoxy)-acetic acid,
(4-{3,3-Bis-[4-(furan-2-yl)-phenyl]-2-ethoxy-allylsulfanyl}-2-methyl-phenoxy)-acetic acid(4-{3,3-Bis-[4-(5-chloro-thiophen-2-yl)-phenyl]-2-ethoxy-allylsulfanyl}-2-methyl-phenoxy)-acetic acid,
(4-{3,3-Bis-[4-(5-chloro-thiophen-2-yl)-phenyl]-2-ethoxy-allyloxy}-2-methyl-phenoxy)-acetic acid,
{4-[3,3-Bis-(4-thiophen-2-yl-phenyl)-2-ethoxy-allyloxy]-2-methyl-phenoxy}-acetic acid,
{4-[3,3-Bis-(4-thiophen-2-yl-phenyl)-2-ethoxy-allylsulfanyl]-2-methyl-phenoxy}-acetic acid,
(4-{3,3-Bis-[4-(5-acetyl-thiophen-2-yl)-phenyl]-2-ethoxy-allylsulfanyl}-2-methyl-phenoxy)-acetic acid,
(4-{3,3-Bis-[4-(5-acetyl-thiophen-2-yl)-phenyl]-2-ethoxy-allyloxy}-2-methyl-phenoxy)-acetic acid,
(4-{3,3-Bis-[4-(5-acetyl-thiophen-2-yl)-phenyl]-2-ethoxy-allyloxy}-2-methyl-phenoxy)-acetic acid,
(4-{3,3-Bis-[4-(5-acetyl-thiophen-2-yl)-phenyl]-2-ethoxy-allylsulfanyl}-2-methyl-phenoxy)-acetic acid,
{4-[3,3-Bis-(3'-methylsulfanyl-biphenyl-4-yl)-2-ethoxy-allylsulfanyl]-2-methyl-phenoxy}-acetic acid,
{4-[3,3-Bis-(3'-methylsulfanyl-biphenyl-4-yl)-2-ethoxy-allyloxy]-2-methyl-phenoxy}-acetic acid,
{4-[3,3-Bis-(3'-amino-biphenyl-4-yl)-2-ethoxy-allyloxy]-2-methyl-phenoxy}-acetic acid,
{4-[3,3-Bis-(3'-amino-biphenyl-4-yl)-2-ethoxy-allylsulfanyl]-2-methyl-phenoxy}-acetic acid,
{4-[3,3-Bis-(4'-amino-biphenyl-4-yl)-2-ethoxy-allylsulfanyl]-2-methyl-phenoxy}-acetic acid,
{4-[3,3-Bis-(4'-amino-biphenyl-4-yl)-2-ethoxy-allyloxy]-2-methyl-phenoxy}-acetic acid,
{4-[3,3-Bis-(4-pyridin-2-yl-phenyl)-2-ethoxy-allyloxy]-2-methyl-phenoxy}-acetic acid,
{4-[3,3-Bis-(4-pyridin-2-yl-phenyl)-2-ethoxy-allylsulfanyl]-2-methyl-phenoxy}-acetic acid, {4-[3,3-Bis-(4'-methanesulfonyl-biphenyl-4-yl)-2-ethoxy-allylsulfanyl]-2-methyl-phenoxy}-acetic acid,
{4-[3,3-Bis-(4'-methanesulfonyl-biphenyl-4-yl)-2-ethoxy-allyloxy]-2-methyl-phenoxy}-acetic acid,
{4-[3,3-Bis-(3'-dimethylcarbamoyl-biphenyl-4-yl)-2-ethoxy-allylsulfanyl]-2-methyl-phenoxy}-acetic acid,
{4-[3,3-Bis-(3'-dimethylcarbamoyl-biphenyl-4-yl)-2-ethoxy-allyloxy]-2-methyl-phenoxy}-acetic acid,
{4-[3,3-Bis-(4'-methoxy-biphenyl-4-yl)-2-ethoxy-allyloxy]-2-methyl-phenoxy}-acetic acid,
{4-[3,3-Bis-(4'-methoxy-biphenyl-4-yl)-2-ethoxy-allylsulfanyl]-2-methyl-phenoxy}-acetic acid,
{4-[3,3-Bis-(4'-trifluoromethoxy-biphenyl-4-yl)-2-ethoxy-allylsulfanyl]-2-methyl-phenoxy}-acetic acid,
{4-[3,3-Bis-(4'-trifluoromethoxy-biphenyl-4-yl)-2-ethoxy-allyloxy]-2-methyl-phenoxy}-acetic acid,
{4-[3,3-Bis-(4'-methyl-biphenyl-4-yl)-2-ethoxy-allyloxy]-2-methyl-phenoxy}-acetic acid,
{4-[3,3-Bis-(4'-methyl-biphenyl-4-yl)-2-ethoxy-allylsulfanyl]-2-methyl-phenoxy}-acetic acid,
{4-[3,3-Bis-(4'-trifluoromethyl-biphenyl-4-yl)-2-ethoxy-allylsulfanyl]-2-methyl-phenoxy}-acetic acid,
{4-[3,3-Bis-(4'-trifluoromethyl-biphenyl-4-yl)-2-ethoxy-allyloxy]-2-methyl-phenoxy}-acetic acid,
{4-[3,3-Bis-(4'-chloro-biphenyl-4-yl)-2-ethoxy-allyloxy]-2-methyl-phenoxy}-acetic acid,
{4-[3,3-Bis-(4'-chloro-biphenyl-4-yl)-2-ethoxy-allylsulfanyl]-2-methyl-phenoxy}-acetic acid,
{4-[3,3-Bis-(4'-chloro-biphenyl-4-yl)-2-ethoxy-allyloxy]-2-methyl-phenoxy}-acetic acid,
{4-[3,3-Bis-(4'-tert-butyl-biphenyl-4-yl)-2-ethoxy-allyloxy]-2-methyl-phenoxy}-acetic acid,
[4-(3,3-Bis-[1,1';4',1'']terphenyl-4-yl-2-ethoxy-allylsulfanyl)-2-methyl-phenoxy]-acetic acid,
[4-(3,3-Bis-[1,1';4',1'']terphenyl-4-yl-2-ethoxy-allylsulfanyl)-2-methyl-phenoxy]-acetic acid,
{4-[3,3-Bis-(4'-acetyl-biphenyl-4-yl)-2-ethoxy-allylsulfanyl]-2-methyl-phenoxy}-acetic acid,
{4-[3,3-Bis-(4'-acetyl-biphenyl-4-yl)-2-ethoxy-allyloxy]-2-methyl-phenoxy}-acetic acid,
{4-[3,3-Bis-(4'-phenoxy-biphenyl-4-yl)-2-ethoxy-allyloxy]-2-methyl-phenoxy}-acetic acid,
{4-[3,3-Bis-(4'-phenoxy-biphenyl-4-yl)-2-ethoxy-allylsulfanyl]-2-methyl-phenoxy}-acetic acid,
{4-[3,3-Bis-(4'-isopropyl-biphenyl-4-yl)-2-ethoxy-allylsulfanyl]-2-methyl-phenoxy}-acetic acid,
{4-[3,3-Bis-(4'-isopropyl-biphenyl-4-yl)-2-ethoxy-allyloxy]-2-methyl-phenoxy}-acetic acid,
{4-[3,3-Bis-(3',4'-difluoro-biphenyl-4-yl)-2-ethoxy-allyloxy]-2-methyl-phenoxy}-acetic acid,
{4-[3,3-Bis-(3',4'-difluoro-biphenyl-4-yl)-2-ethoxy-allylsulfanyl]-2-methyl-phenoxy}-acetic acid,
{4-[3,3-Bis-(3',5'-dichloro-biphenyl-4-yl)-2-ethoxy-allylsulfanyl]-2-methyl-phenoxy}-acetic acid,
{4-[3,3-Bis-(3',5'-dichloro-biphenyl-4-yl)-2-ethoxy-allyloxy]-2-methyl-phenoxy}-acetic acid,
{4-[3,3-Bis-(3'-chloro-4'-fluoro-biphenyl-4-yl)-2-ethoxy-allyloxy]-2-methyl-phenoxy}-acetic acid,
{4-[3,3-Bis-(3'-chloro-4'-fluoro-biphenyl-4-yl)-2-ethoxy-allylsulfanyl]-2-methyl-phenoxy}-acetic acid,
(4-{3,3-Bis-[4-(4-methyl-furan-2-yl)-phenyl]-2-ethoxy-allyloxy}-2-methyl-phenoxy)-acetic acid,
(4-{3,3-Bis-[4-(4-methyl-furan-2-yl)-phenyl]-2-ethoxy-allylsulfanyl}-2-methyl-phenoxy)-acetic acid,
(4-{3,3-Bis-[4-(4-chloro-thiophen-2-yl)-phenyl]-2-ethoxy-allylsulfanyl}-2-methyl-phenoxy)-acetic acid, (4-{3,3-Bis-[4-(4-chloro-thiophen-2-yl)-phenyl]-2-ethoxy-allyloxy}-2-methyl-phenoxy)-acetic acid,
(4-{3,3-Bis-[4-(4-acetyl-thiophen-2-yl)-phenyl]-2-ethoxy-allylsulfanyl}-2-methyl-phenoxy)-acetic acid,
(4-{3,3-Bis-[4-(4-acetyl-thiophen-2-yl)-phenyl]-2-ethoxy-allyloxy}-2-methyl-phenoxy)-acetic acid,
(4-{3,3-Bis-[4-(4-acetyl-thiophen-2-yl)-phenyl] 2-ethoxy-allyloxy}-2-methyl-phenoxy)-acetic acid,
(4-{3,3-Bis-[4-(4-acetyl-thiophen-2-yl)-phenyl]-2-ethoxy-allylsulfanyl}-2-methyl-phenoxy)-acetic acid,
{4-[3,3-Bis-(4-pyridin-3-yl-phenyl)-2-ethoxy-allyloxy]-2-methyl-phenoxy}-acetic acid,
{4-[3,3-Bis-(4-pyridin-3-yl-phenyl)-2-ethoxy-allylsulfanyl]-2-methyl-phenoxy}-acetic acid,
{4-[3,3-Bis-(3'-methoxy-biphenyl-4-yl)-2-ethoxy-allyloxy]-2-methyl-phenoxy}-acetic acid,
{4-[3,3-Bis-(3'-methoxy-biphenyl-4-yl)-2-ethoxy-allylsulfanyl]-2-methyl-phenoxy}-acetic acid,
{4-[3,3-Bis-(3'-trifluoromethoxy-biphenyl-4-yl)-2-ethoxy-allylsulfanyl]-2-methyl-phenoxy}-acetic acid,
{4-[3,3-Bis-(3'-trifluoromethoxy-biphenyl-4-yl)-2-ethoxy-allyloxy]-2-methyl-phenoxy}-acetic acid,
{4-[3,3-Bis-(3'-methyl-biphenyl-4-yl)-2-ethoxy-allyloxy]-2-methyl-phenoxy}-acetic acid,
{4-[3,3-Bis-(3'-methyl-biphenyl-4-yl)-2-ethoxy-allylsulfanyl]-2-methyl-phenoxy}-acetic acid,
{4-[3,3-Bis-(3'-trifluoromethyl-biphenyl-4-yl)-2-ethoxy-allylsulfanyl]-2-methyl-phenoxy}-acetic acid,
{4-[3,3-Bis-(3'-trifluoromethyl-biphenyl-4-yl)-2-ethoxy-allyloxy]-2-methyl-phenoxy}-acetic acid,
{4-[3,3-Bis-(3'-chloro-biphenyl-4-yl)-2-ethoxy-allyloxy]-2-methyl-phenoxy}-acetic acid,
{4-[3,3-Bis-(3'-chloro-biphenyl-4-yl)-2-ethoxy-allylsulfanyl]-2-methyl-phenoxy}-acetic acid,
{4-[3,3-Bis-(3'-chloro-biphenyl-4-yl)-2-ethoxy-allyloxy]-2-methyl-phenoxy}-acetic acid,
{4-[3,3-Bis-(3'-tert-butyl-biphenyl-4-yl)-2-ethoxy-allyloxy]-2-methyl-phenoxy}-acetic acid,
{4-[3,3-Bis-(3'-acetyl-biphenyl-4-yl)-2-ethoxy-allylsulfanyl]-2-methyl-phenoxy}-acetic acid,
{4-[3,3-Bis-(3'-acetyl-biphenyl-4-yl)-2-ethoxy-allyloxy]-2-methyl-phenoxy}-acetic acid,
{4-[3,3-Bis-(3'-phenoxy-biphenyl-4-yl)-2-ethoxy-allyloxy]-2-methyl-phenoxy}-acetic acid,
{4-[3,3-Bis-(3'-phenoxy-biphenyl-4-yl)-2-ethoxy-allylsulfanyl]-2-methyl-phenoxy}-acetic acid,
{4-[3,3-Bis-(3'-isopropyl-biphenyl-4-yl)-2-ethoxy-allylsulfanyl]-2-methyl-phenoxy}-acetic acid,
{4-[3,3-Bis-(3'-isopropyl-biphenyl-4-yl)-2-ethoxy-allyloxy]-2-methyl-phenoxy}-acetic acid,
{4-[3,3-Bis-(2',4'-difluoro-biphenyl-4-yl)-2-ethoxy-allyloxy]-2-methyl-phenoxy}-acetic acid,
{4-[3,3-Bis-(2',4'-difluoro-biphenyl-4-yl)-2-ethoxy-allylsulfanyl]-2-methyl-phenoxy}-acetic acid,
{4-[3,3-Bis-(2',5'-dichloro-biphenyl-4-yl)-2-ethoxy-allylsulfanyl]-2-methyl-phenoxy}-acetic acid,
{4-[3,3-Bis-(2',5'-dichloro-biphenyl-4-yl)-2-ethoxy-allyloxy]-2-methyl-phenoxy}-acetic acid,
{4-[3,3-Bis-(2'-chloro-4'-fluoro-biphenyl-4-yl)-2-ethoxy-allyloxy]-2-methyl-phenoxy}-acetic acid,
{4-[3,3-Bis-(2'-chloro-4'-fluoro-biphenyl-4-yl)-2-ethoxy-allylsulfanyl]-2-methyl-phenoxy}-acetic acid,
[4-(3,3-Bis-biphenyl-4-yl-allylsulfanyl)-2-chloro-phenoxy]-acetic acid,
[4-(3,3-Bis-biphenyl-4-yl-allyloxy)-2-chloro-phenoxy]-acetic acid,
(4-{3,3-Bis-[4-(5-methyl-furan-2-yl)-phenyl]-allyloxy}-2-chloro-phenoxy)-acetic acid,
(4-{3,3-Bis-[4-(-furan-2-yl)-phenyl]-allyloxy}-2-chloro-phenoxy)-acetic acid,
(4-{3,3-Bis-[4-(5-methyl-furan-2-yl)-phenyl]-allylsulfanyl}-2-chloro-phenoxy)-acetic acid,
(4-{3,3-Bis-[4-(furan-2-yl)-phenyl]-allylsulfanyl}-2-chloro-phenoxy)-acetic acid,
(4-{3,3-Bis-[4-(5-chloro-thiophen-2-yl)-phenyl]-allylsulfanyl}-2-chloro-phenoxy)-acetic acid,
(4-{3,3-Bis-[4-(5-chloro-thiophen-2-yl)-phenyl]-allyloxy}-2-chloro-phenoxy)-acetic acid,
{4-[3,3-Bis-(4-thiophen-2-yl-phenyl)-allyloxy]-2-chloro-phenoxy}-acetic acid,
{4-[3,3-Bis-(4-thiophen-2-yl-phenyl)-allylsulfanyl]-2-chloro-phenoxy}-acetic acid,
(4-{3,3-Bis-[4-(5-acetyl-thiophen-2-yl)-phenyl]-allylsulfanyl}-2-chloro-phenoxy)-acetic acid,
(4-{3,3-Bis-[4-(5-acetyl-thiophen-2-yl)-phenyl]-allyloxy}-2-chloro-phenoxy)-acetic acid,
(4-{3,3-Bis-[4-(5-acetyl-thiophen-2-yl)-phenyl]-2-ethyl-allyloxy}-2-chloro-phenoxy)-acetic acid,
(4-{3,3-Bis-[4-(5-acetyl-thiophen-2-yl)-phenyl]-2-ethyl-allylsulfanyl}-2-chloro-phenoxy)-acetic acid,
{4-[3,3-Bis-(3'-methylsulfanyl-biphenyl-4-yl)-allylsulfanyl]-2-chloro-phenoxy}-acetic acid,
{4-[3,3-Bis-(3'-methylsulfanyl-biphenyl-4-yl)-allyloxy]-2-chloro-phenoxy}-acetic acid,
{4-[3,3-Bis-(3'-amino-biphenyl-4-yl)-allyloxy]-2-chloro-phenoxy}-acetic acid,
{4-[3,3-Bis-(3'-amino-biphenyl-4-yl)-allylsulfanyl]-2-chloro-phenoxy}-acetic acid,
{4-[3,3-Bis-(4'-amino-biphenyl-4-yl)-allylsulfanyl]-2-chloro-phenoxy}-acetic acid,
{4-[3,3-Bis-(4'-amino-biphenyl-4-yl)-allyloxy]-2-chloro-phenoxy}-acetic acid,
{4-[3,3-Bis-(4-pyridin-2-yl-phenyl)-allyloxy]-2-chloro-phenoxy}-acetic acid,
{4-[3,3-Bis-(4-pyridin-2-yl-phenyl)-allylsulfanyl]-2-chloro-phenoxy}-acetic acid,
{4-[3,3-Bis-(4'-methanesulfonyl-biphenyl-4-yl)-allylsulfanyl]-2-chloro-phenoxy}-acetic acid,
{4-[3,3-Bis-(4'-methanesulfonyl-biphenyl-4-yl)-allyloxy]-2-chloro-phenoxy}-acetic acid,
{4-[3,3-Bis-(4'-methoxy-biphenyl-4-yl)-allyloxy]-2-chloro-phenoxy}-acetic acid,
{4-[3,3-Bis-(4'-methoxy-biphenyl-4-yl)-allylsulfanyl]-2-chloro-phenoxy}-acetic acid,
{4-[3,3-Bis-(4'-trifluoromethoxy-biphenyl-4-yl)-allylsulfanyl]-2-chloro-phenoxy}-acetic acid,
{4-[3,3-Bis-(4'-trifluoromethoxy-biphenyl-4-yl)-allyloxy]-2-chloro-phenoxy}-acetic acid,
{4-[3,3-Bis-(4'-methyl-biphenyl-4-yl)-allyloxy]-2-methyl-phenoxy}-acetic acid,
{4-[3,3-Bis-(4'-methyl-biphenyl-4-yl)-allylsulfanyl]-2-chloro-phenoxy}-acetic acid,
{4-[3,3-Bis-(4'-trifluoromethyl-biphenyl-4-yl)-allylsulfanyl]-2-chloro-phenoxy}-acetic acid,
{4-[3,3-Bis-(4'-trifluoromethyl-biphenyl-4-yl)-allyloxy]-2-chloro-phenoxy}-acetic acid,
{4-[3,3-Bis-(4'-chloro-biphenyl-4-yl)-allyloxy]-2-chloro-phenoxy}-acetic acid,
{4-[3,3-Bis-(4'-chloro-biphenyl-4-yl)-allylsulfanyl]-2-chloro-phenoxy}-acetic acid,
{4-[3,3-Bis-(4'-chloro-biphenyl-4-yl)-allyloxy]-2-chloro-phenoxy}-acetic acid, {4-[3,3-Bis-(4'-tert-butyl-biphenyl-4-yl)-allyloxy]-2-chloro-phenoxy}-acetic acid,
[4-(3,3-Bis-[1,1';4',1"]terphenyl-4-yl-allylsulfanyl)-2-chloro-phenoxy]-acetic acid,
[4-(3,3-Bis-[1,1';4',1"]terphenyl-4-yl-allylsulfanyl)-2-chloro-phenoxy]-acetic acid,
{4-[3,3-Bis-(4'-acetyl-biphenyl-4-yl)-allylsulfanyl]-2-chloro-phenoxy}-acetic acid,
{4-[3,3-Bis-(4'-acetyl-biphenyl-4-yl)-allyloxy]-2-methyl-phenoxy}-acetic acid,
{4-[3,3-Bis-(4'-phenoxy-biphenyl-4-yl)-allyloxy]-2-chloro-phenoxy}-acetic acid,
{4-[3,3-Bis-(4'-phenoxy-biphenyl-4-yl)-allylsulfanyl]-2-chloro-phenoxy}-acetic acid,
{4-[3,3-Bis-(4'-isopropyl-biphenyl-4-yl)-allylsulfanyl]-2-chloro-phenoxy}-acetic acid,
{4-[3,3-Bis-(4'-isopropyl-biphenyl-4-yl)-allyloxy]-2-chloro-phenoxy}-acetic acid,
{4-[3,3-Bis-(3',4'-difluoro-biphenyl-4-yl)-allyloxy]-2-chloro-phenoxy}-acetic acid,
{4-[3,3-Bis-(3',4'-difluoro-biphenyl-4-yl)-allylsulfanyl]-2-chloro-phenoxy}-acetic acid,
{4-[3,3-Bis-(3',5'-dichloro-biphenyl-4-yl)-allylsulfanyl]-2-chloro-phenoxy}-acetic acid,
{4-[3,3-Bis-(3',5'-dichloro-biphenyl-4-yl)-allyloxy]-2-chloro-phenoxy}-acetic acid,
{4-[3,3-Bis-(3'-chloro-4'-fluoro-biphenyl-4-yl)-allyloxy]-2-chloro-phenoxy}-acetic acid, and
{4-[3,3-Bis-(3'-chloro-4'-fluoro-biphenyl-4-yl)-allylsulfanyl]-2-chloro-phenoxy}-acetic acid, or
a salt thereof with a pharmaceutically acceptable acid or base, optical isomer or mixture of optical isomers, racemic mixture, or tautomeric forms thereof.

43. A compound according to claim 1, which is a PPARδ agonist.

44. A compound according to claim 43, which is a selective PPARδ agonist.

45. A pharmaceutical composition comprising, as an active ingredient, at least one compound according to claim 1 together with one or more pharmaceutically acceptable carriers or excipients.

46. A pharmaceutical composition according to claim 45 in unit dosage form, comprising from about 0.05 mg to about 1000 mg per day of the compound.

47. A pharmaceutical composition according to claim 46 for oral, nasal, transdermal, pulmonal, or parenteral administration.

48. A method for the treatment of conditions mediated by the Peroxisome Proliferator-Activated Receptors (PPAR), wherein the condition is selected from type I diabetes, type II diabetes, impaired glucose tolerance (IGT), insulin resistance, dyslipidemin, Syndrome X, hypertension, obesity, hyperglyccmia, atherloselerosis, hyperlipidemia, coronary artery disease, myocardial ischemia, glomerulonephritis, glomeruloselerosis, nephritic syndrome, hypertensive nephrosclerosis, diabetic complications, loss of cognative function in dementia, psoriasis, Polycystic Ovarian Syndrome (PCOS), osteoporosis, progression from IGT to type II diabetes, and progression from non insulin-requiring type II diabetes to insulin-requiring type II diabetes, the method comprising administering to a subject in need thereof an effective amount of a compound according to claim 1 or a pharmaceutical composition comprising the same.

49. A method for the treatment of type I diabetes, type II diabetes, impaired glucose tolerance, insulin resistance or obesity, the method comprising administering to a subject in need thereof an effective amount of a compound according to claim 1 or of a pharmaceutical composition comprising the same.

50. The method according to claim 48 wherein the effective amount of the compound is in the range of from about 0.05 mg to about 1000 mg per day.

51. The method according to claim 49 wherein the effective amount of the compound is in the range of from about 0.05 mg to about 1000 mg per day.

52. A pharmaceutical composition according to claim 45 in unit dosage form, comprising from about 0.05 mg to about 1000 mg per day of the compound.

53. A pharmaceutical composition according to claim 45 in unit dosage form, comprising from about 0.5 mg to about 200 mg per day of the compound.

54. The method according to claim 48 wherein the effective amount of the compound is in the range of from about 0.1 to about 500 mg per day.

55. The method according to claim 48 wherein the effective amount of the compound is in the range of from about 0.5 mg to about 200 mg per day.

56. The method according to claim 49 wherein the effective amount of the compound is in the range of from about 0.1 to about 500 mg per day.

57. The method according to claim 49 wherein the effective amount of the compound is in the range of from about 0.5 mg to about 200 mg per day.

* * * * *